(12) United States Patent
Chugh

(10) Patent No.: US 10,023,620 B2
(45) Date of Patent: Jul. 17, 2018

(54) METHODS FOR TREATMENT OF NEPHROTIC SYNDROME AND RELATED CONDITIONS

(71) Applicant: THE UAB RESEARCH FOUNDATION, Birmingham, AL (US)

(72) Inventor: Sumant S Chugh, Mountain Brook, AL (US)

(*) Notice: Subject to any disclaimer, the term of this patent is extended or adjusted under 35 U.S.C. 154(b) by 0 days.

(21) Appl. No.: 14/855,060

(22) Filed: Sep. 15, 2015

(65) Prior Publication Data

US 2016/0355558 A1 Dec. 8, 2016

Related U.S. Application Data

(60) Division of application No. 13/841,240, filed on Mar. 15, 2013, now Pat. No. 9,139,629, which is a continuation-in-part of application No. 13/364,962, filed on Feb. 2, 2012, now Pat. No. 9,475,850, and a continuation of application No. PCT/US2011/039255, filed on Jun. 6, 2011.

(60) Provisional application No. 61/438,854, filed on Feb. 2, 2011, provisional application No. 61/351,866, filed on Jun. 5, 2010.

(51) Int. Cl.

| | |
|---|---|
| *A61K 38/16* | (2006.01) |
| *C07K 1/00* | (2006.01) |
| *C07K 14/00* | (2006.01) |
| *C07K 17/00* | (2006.01) |
| *C07K 16/00* | (2006.01) |
| *C12N 15/00* | (2006.01) |
| *A01N 63/00* | (2006.01) |
| *C07K 14/47* | (2006.01) |
| *A61K 38/12* | (2006.01) |
| *C07K 14/765* | (2006.01) |
| *A61K 38/42* | (2006.01) |
| *A61K 35/16* | (2015.01) |
| *A61K 38/04* | (2006.01) |
| *C07K 14/76* | (2006.01) |
| *A61K 38/38* | (2006.01) |
| *A61K 38/00* | (2006.01) |
| *C07K 14/515* | (2006.01) |
| *C07K 14/775* | (2006.01) |
| *A61K 9/127* | (2006.01) |

(52) U.S. Cl.
CPC ............ *C07K 14/47* (2013.01); *A61K 35/16* (2013.01); *A61K 38/00* (2013.01); *A61K 38/04* (2013.01); *A61K 38/12* (2013.01); *A61K 38/16* (2013.01); *A61K 38/38* (2013.01); *A61K 38/42* (2013.01); *C07K 14/515* (2013.01); *C07K 14/76* (2013.01); *C07K 14/765* (2013.01); *C12N 15/00* (2013.01); *A61K 9/1275* (2013.01); *C07K 14/775* (2013.01)

(58) Field of Classification Search
None
See application file for complete search history.

(56) References Cited

U.S. PATENT DOCUMENTS

| | | |
|---|---|---|
| 2003/0054517 A1 | 3/2003 | Goddard et al. |
| 2003/0228659 A1 | 12/2003 | Ballinger et al. |
| 2005/0054570 A1 | 3/2005 | Rosen et al. |
| 2007/0026002 A1 | 2/2007 | Gerber et al. |
| 2011/0305663 A1 | 12/2011 | Gosselin et al. |
| 2013/0261054 A1 | 10/2013 | Chugh |

FOREIGN PATENT DOCUMENTS

| | | |
|---|---|---|
| WO | 2006014678 | 9/2006 |
| WO | 2011153525 | 12/2011 |

OTHER PUBLICATIONS

Kita-Aoyama "Notice of Rejection—Japanese patent application No. 2013-513408" Japanese International Patent Bureau; Apr. 28, 2015; pp. 1-6.
Sun, H., et al. "Shenzangbing Yu Touxi Shenyizhi Zazhi" 2005, vol. 14, No. 6, pp. 531-535.
Sun, H., et al. "Enhanced Expression of ANGPTL2 in the Microvascular Lesions of Diabetic Glomerulopathy" Nephron Experimental Nephrology; 2007, vol. 105, pp. E117-E123.
Japanese Patent Gazette Laid-open Publication No. 2008-507531 pp. 1-107.
Lee, E.C., et al. "Identification of a New Functional Domain in Angiopoietin-like 3 (ANGPTL3) and Angiopoietin-like 4 (ANGPTL4) Involved in Binding and Inhibition of Lipoprotein Lipase (LPL)" J. Biol. Chem., 2009, vol. 284, No. 20, pp. 13735-13745.
Le Jan, et al. "Angiopoietin-Like 4 is a Proangiogenic Factor Produced during Ischemia and in Conventional Renal Cell Carcinoma" American Journal of Pathlogoy, vol. 162, No. 5, May 2003; pp. 1521-1528.
Segen's Medical Dictionary, available online at http://medical-dictionary.thefreedictionary.com/p/administration, 3 pages at p. 1, lines 3-7, (2012).
GenBank Database, NCBI Acession No. NP_647475, version GI:21536398 (first available 2002).
Matthews, "Structural and Genetic Analysis of Protein Stability," Annu. Rev. Biochem. 62:139-160 (1993).

(Continued)

*Primary Examiner* — James H Alstrum Acevedo
*Assistant Examiner* — Thea D'Ambrosio
(74) *Attorney, Agent, or Firm* — Nicholas J. Landau; Bradley Arant Boult Cummings LLP

(57) ABSTRACT

The present disclosure provides a polypeptide and method for treating and/or preventing nephrotic syndrome, such as but not limited to those associated with minimal change disease and membranous nephropathy, and conditions related to nephrotic syndrome, such as but not limited to, proteinuria and edema, as well as diabetic nephropathy, diabetes mellitus, lupus nephritis or primary glomerular disease. The present disclosure further provides methods for reducing proteinuria and other disease states as discussed herein. Such methods comprise the therapeutic delivery of an Angptl4 polypeptide or Angptl4 polypeptide derivative to a subject.

35 Claims, 27 Drawing Sheets

(56) References Cited

OTHER PUBLICATIONS

Raju, et al. "Glycoengineering of Therapeutic Glycoproteins: In Vitro Galactosylation and Sialylation of Glycoproteins with Terminal N-Acetylglucosamine and Galactose Residues," Biochem. 40:8868-8876 (2001).
Yuan, et al. "Hypertriglyceridemia: its etiology, effects and treatment," Canadian Med. Assoc. J. 176:1113-1120(2007).
Choi Sung Hee "Written Opinion of the International Searching Authority" Feb. 14, 2012; PCT/US2011/039255; pp. 1-4.
Clement, et al. "Podocyte-secreted angiopoietin-like-4 mediates proteinuria in glucocorticoid-sensitive nephrotic syndrome" Nature Medicine: vol. 17; No. 1; Jan. 2011; pp. 117-145.
Aich, et al. "Development of delivery methods for carbohydrate-based drugs: controlled release of biologically-active short chain fatty acid-hexosamine analogs" Glycoconj J.: May 11, 2010; pp. 1-14.
Galeano, et al. "Mutation in the key enzyme of sialic acid biosynthesis causes severe glomerular proteinuria and is rescued by N-acetylmannosamine" The Journal of Clinical Investigation: vol. 17; No. 6; Jun. 2007; pp. 1585-1594.
Yin, et al. "Genetic Variation in ANGPTL4 Provides Insights into Protein Processing and Function" Journal of Biological Chemistry; vol. 284; No. 19; May 8, 2009; pp. 13213-13222.
Romeo, et al. "Population-based resequencing of ANGPTL4 uncovers variations that reduce triglycerides and increase HDL" Nature Genetics; vol. 39; No. 4; Apr. 2007; pp. 513-514.
Jackson, et al. "The codependence of angiogenesis and chronic inflammation" The FASEB Journal; vol. 11; May 1997; pp. 457-465.
Brenner, Barry M. "Brenner & Rector's The Kidney" Saunders Elsevier; 8th Edition; vol. 1; pp. 987-994.
"Notice of Rejection—Japanese patent application No. 2016-503307" Japanese patent office; dated Mar. 27, 2018; pp. 1-4.
Lee Su Jeong "Notice of Decision of Final Rejection—Korean patent application No. 10-2013-7000446" Korean Intellectual Property Office; dated Mar. 13, 2018; pp. 1-3.
Rishu Bharti "Examination Report—India patent application No. 5/DELNP/2013" dated Mar. 21, 2018; pp.
Zellner, Eveline "Extended European Search Report: EP application No. 17206254.9" European Patent Office; dated Mar. 15, 2018; pp. 1-9.

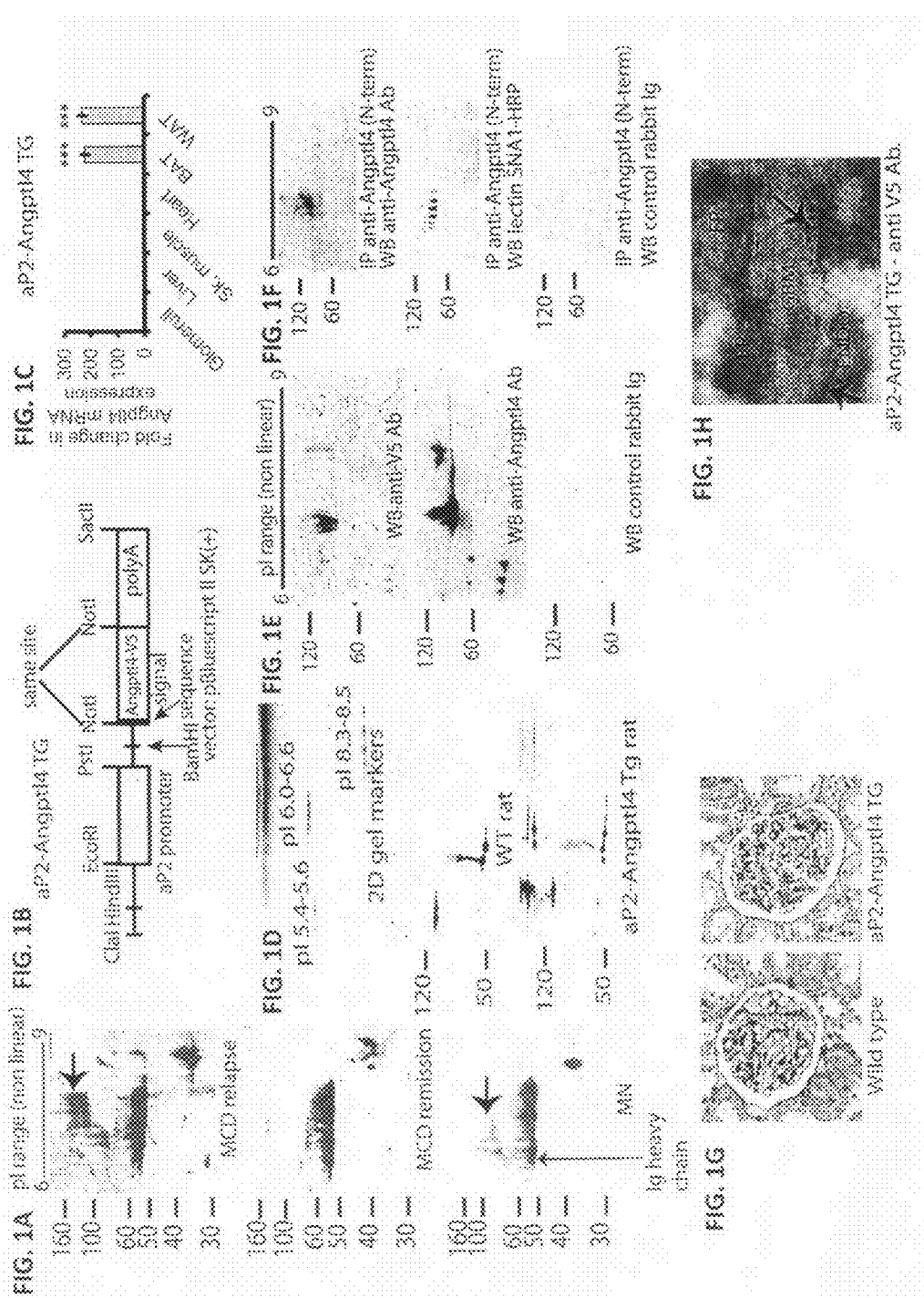

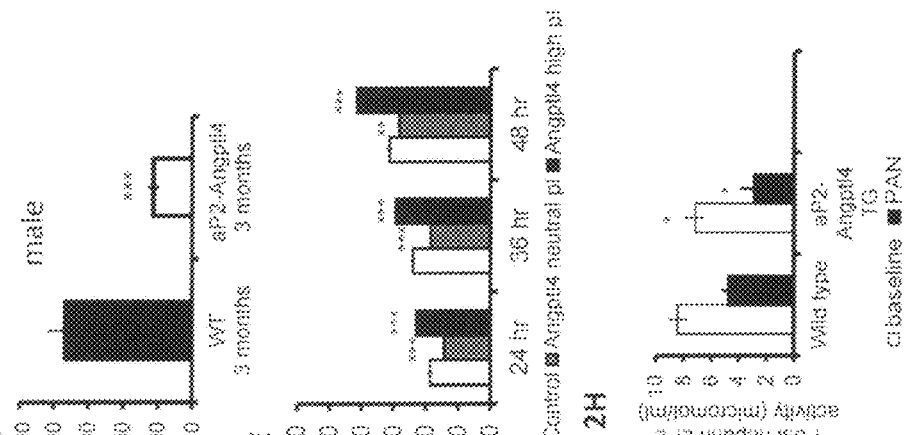

| Gene / transgene | Species | Forward primer | Reverse primer | Taqman probe |
|---|---|---|---|---|
| Angptl4 | rat | tctgggatctccaccattttg | tcaccgtccagcctccat | caactgtgagatgacttc |
| Angptl4 | rat | cgccaccgcttacaca | cagaggctgatctgaaaagt | tgccaggaactcttt |
| aP2-Angptl4 construct | rat | tgttgatccagcccatgga | agggataggcttaccttcgaatg | cagcagcctccc |
| Prolactin (genomic) | rat | cttgaagggattgaaaagataattagc | ccatgagtcagaaaagcattgaac | aggtgagcattcctg |

FIG. 3

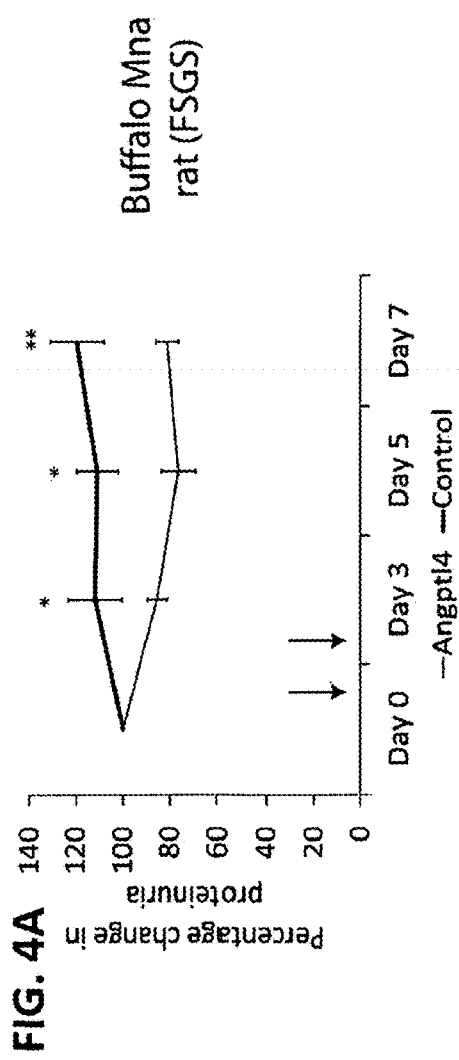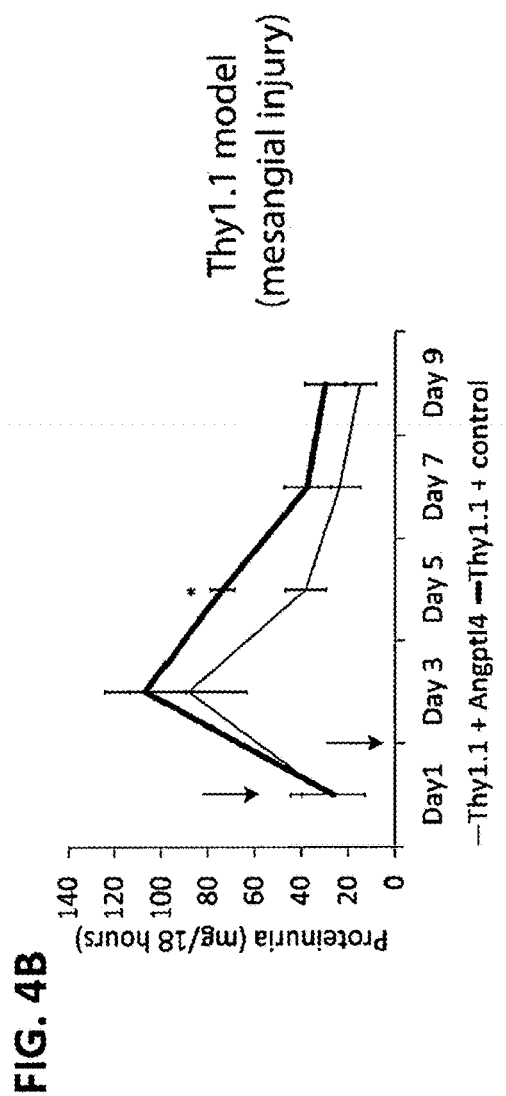
FIG. 4A
FIG. 4B

FIG. 5

SEQ ID NO: 1
MSGAPTAGAALMLCAATAVLLSAQGGPVQSKSPRFASWDEMNVLAHGLLQLGQGLREHAERTRSQLSALER
RLSACGSACQGTEGSTDLPLAPESRVDPEVLHSLQTQLKAQNSRIQQLFHKVAQQQRHLEKQHLRIQHLQSQFGLLD
HKHLDHEVAKPARRKRLPEMAQPVDPAHNVSRLHRLPRDCQELFQVGERQSGLFEIQPQGSPPFLVNCKMTSDGGWT
VIQRRHDGSVDFNRPWEAYKAGFGDPHGEFWLGLEKVHSITGDRNSRLAVQLRDWDGNAELLQFSVHLGGEDTAYSL
QLTAPVAGQLGATTVPPSGLSVPFSTWDQDHDLRRDKNCAKSLSGGWWFGTCSHSNLNGQYFRSIPQQRQKLKKGIF
WKTWRGRYYPLQATTMLIQPMAAEAAS
406 amino acids SEQ ID NO: 2
```
   1    ataaaaaccg tcctcgggcg cggcggggag aagccgagct gagcggatcc tcacacgact
  61    gtgatccgat tctttccagc ggcttctgca accaagcggg tcttacccc  ggtcctccgc
 121    gtctccagtc ctcgcacctg aaccccaac  gtccccgaga gtccccgaat ccccgctccc
 181    aggctaccta agaggatgag cggtgctccg acggccgggg cagccctgat gctctgcgcc
 241    gccaccgccg tgctactgag cgctcagggc ggacccgtgc agtccaagtc gccgcgcttt
 301    gcgtcctggg acgagatgaa tgtcctggcg cacggactcc tgcagctcgg ccaggggctg
 361    cgcgaacacg cggagcgcac ccgcagtcag ctgagcgcgc tggagcggcg cctgagcgcg
 421    tgcgggtccg cctgtcaggg aaccgagggg tccaccgacc tcccgttagc ccctgagagc
 481    cgggtggacc ctgaggtcct tcacagcctg cagacacaac tcaaggctca gaacagcagg
 541    atccagcaac tcttccacaa ggtggcccag cagcagcggc acctggagaa gcagcacctg
 601    cgaattcagc atctgcaaag ccagtttggc ctcctggacc acaagcacct agaccatgag
 661    gtggccaagc ctgcccgaag aaagaggctg cccgagatgg cccagccagt tgacccggct
 721    cacaatgtca gccgcctgca ccggctgccc agggattgcc aggagctgtt ccaggttggg
 781    gagaggcaga gtggactatt tgaaatccag cctcaggggt ctccgccatt tttggtgaac
 841    tgcaagatga cctcagatgg aggctggaca gtaattcaga ggcgccacga tggctcagtg
 901    gacttcaacc ggccctggga agcctacaag gcggggtttg gggatcccca cggcgagttc
 961    tggctgggtc tggagaaggt gcatagcatc acggggggacc gcaacagccg cctggccgtg
1021    cagctgcggg actgggatgg caacgccgag ttgctgcagt tctccgtgca cctgggtggc
1081    gaggacacgg cctatagcct gcagctcact gcacccgtgg ccggccagct gggcgccacc
1141    accgtcccac ccagcggcct ctccgtaccc ttctccactt gggaccagga tcacgacctc
1201    cgcagggaca agaactgcgc caagagcctc tctggaggct ggtggtttgg cacctgcagc
1261    cattccaacc tcaacggcca gtacttccgc tccatcccac agcagcggca gaagcttaag
1321    aagggaatct tctggaagac ctggcggggc cgctactacc cgctgcaggc caccaccatg
1381    ttgatccagc ccatggcagc agaggcagcc tcctagcgtc ctggctgggc ctggtcccag
1441    gcccacgaaa gacggtgact cttggctctg cccgaggatg tggccgttcc ctgcctgggc
1501    aggggctcca aggaggggcc atctgaaac  ttgtggacag agaagaagac cacgactgga
1561    gaagccccct ttctgagtgc aggggggctg catgcgttgc ctcctgagat cgaggctgca
1621    ggatatgctc agactctaga ggcgtggacc aaggggcatg gagcttcact ccttgctggc
1681    cagggagttg gggactcaga gggaccactt ggggccagcc agactggcct caatggcgga
1741    ctcagtcaca ttgactgacg gggaccaggg cttgtgtggg tcgagagcgc cctcatggtg
1801    ctggtgctgt tgtgtgtagg tcccctgggg acacaagcag gcgccaatgg tatctgggcg
1861    gagctcacag agttcttgga ataaaagcaa cctcagaaca cttaaaaaaa aaaaaaaaaa
1921    aaaaaaaaaa aaaaaaaaaa aaaaaaaaaa aaaaaaaaaa aaaaaaa
```

SEQ ID NO: 3
MSGAPTAGAALMLCAATAVLLSAQGGPVQSKSPRFASWDEMNVLAHGLLQLGQGLREHAERTRSQLSALERRLSACG
SACQGTEGSTDLPLAPESRVDPEVLHSLQTQLKAQNSRIQQLFHKVAQQQRHLEKQHLRIQHLQSQFGLLDHKHLDH
EVAKPARRKRLPEMAQPVDPAHNVSRLHHGGWTVIQRRHDGSVDFNRPWEAYKAGFGDPHGEFWLGLEKVHSITGDR
NSRLAVQLRDWDGNAELLQFSVHLGGEDTAYSLQLTAPVAGQLGATTVPPSGLSVPFSTWDQDHDLRRDKNCAKSLS
GGWWFGTCSHSNLNGQYFRSIPQQRQKLKKGIFWKTWRGRYYPLQATTMLIQPMAAEAAS
368 amino acids

FIG. 5 (continued)

SEQ ID NO: 4
```
1     ataaaaaccg tcctcgggcg cggcggggag aagccgagct gagcggatcc tcacacgact
61    gtgatccgat tctttccagc ggcttctgca accaagcggg tcttaccccc ggtcctccgc
121   gtctccagtc ctcgcacctg gaacccaac gtccccgaga gtccccgaat cccgctccc
181   aggctaccta agaggatgag cggtgctccg acggccgggg cagccctgat gtctgcgcc
241   gccaccgccg tgctactgag cgctcagggc ggaccgtgc agtccaagtc gccgcgcttt
301   gcgtcctggg acgagatgaa tgtcctggcg cacggactcc tgcagctcgg ccaggggctg
361   cgcgaacacg cggagcgcac ccgcagtcag ctgagcgcgc tggagcggcg cctgagcgcg
421   tgcgggtccg cctgtcaggg aaccgagggg tccaccgacc tcccgttagc ccctgagagc
481   cgggtggacc ctgaggtcct tcacagcctg cagacacaac tcaaggctca gaacagcagg
541   atccagcaac tcttccacaa ggtggcccag cagcagcggc acctggagaa gcagcacctg
601   cgaattcagc atctgcaaag ccagtttggc ctcctggacc acaagcacct agaccatgag
661   gtggccaagc ctgcccgaag aaagaggctg cccgagatgg cccagccagt tgacccggct
721   cacaatgtca gccgcctgca ccatggaggc tggacagtaa ttcagaggcg ccacgatggc
781   tcagtggact tcaaccggcc ctgggaagcc tacaaggcgg ggtttgggga tccccacggc
841   gagttctggc tgggtctgga gaaggtgcat agcatcacgg gggaccgcaa cagccgcctg
901   gccgtgcagc tgcgggactg ggatggcaac gccgagttgc tgcagttctc cgtgcacctg
961   ggtggcgagg acacggccta tagcctgcag ctcactgcac ccgtggccgg ccagctgggc
1021  gccaccaccg tcccacccag cggcctctcc gtaccttct ccacttggga ccaggatcac
1081  gacctccgca gggacaagaa ctgcgccaag agcctctctg gaggctggtg gtttggcacc
1141  tgcagccatt ccaacctcaa cggccagtac ttccgctcca tcccacagca gcggcagaag
1201  cttaagaagg gaatcttctg gaagacctgg cggggccgct actaccgct gcaggccacc
1261  accatgttga tccagcccat ggcagcagag gcagcctcct agcgtcctgg ctgggcctgg
1321  tcccaggccc acgaaagacg gtgactcttg gctctgcccg aggatgtggc cgttccctgc
1381  ctgggcaggg gctccaagga ggggccatct ggaaacttgt ggacagagaa gaagaccacg
1441  actggagaag cccccttct gagtgcaggg gggctgcatg cgttgcctcc tgagatcgag
1501  gctgcaggat atgctcagac tctagaggcg tggaccaagg ggcatggagc ttcactcctt
1561  gctggccagg gagttgggga ctcagaggga ccacttgggg ccagccagac tggcctcaat
1621  ggcggactca gtcacattga ctgacgggga ccagggcttg tgtgggtcga gagcgccctc
1681  atggtgctgg tgctgttgtg tgtaggtccc ctgggacac aagcaggcgc caatggtatc
1741  tgggcggagc tcacagagtt cttggaataa agcaacctc agaacactta aaaaaaaaaa
1801  aaaaaaaaaa aaaaaaaaaa aaaaaaaaaa aaaaaaaaaa aaaaaaaaaa aaa
```

SEQ ID NO: 5
MRCAPTAGAALVLCAATAGLLSAQGRPAQPEPPRFASWDEMNLLAHGLLQLGHGLREHVERTRGQLGALERRMAACG
NACQGPKGTDPKDRVPEGQAPETLQSLQTQLKAQNSKIQQLFQKVAQQQRYLSKQNLRIQNLQSQIDLLTPTHLDNG
VDKTSRGKRLPKMAQLIGLTPNATRLHRPPRDCQELFQEGERHSGLFQIQPLGSPPFLVNCEMTSDGGWTVIQRRLN
GSVDFNQSWEAYKDGFGDPQGEFWLGLEKMHSITGDRGSQLAVQLQDWDGNAKLLQFPIHLGGEDTAYSLQLTEPTA
NELGATNVSPNGLSLPFSTWDQDHDLRGDLNCAKSLSGGWWFGTCSHSNLNGQYFHSIPRQRQQRKKGIFWKTWKGR
YYPLQATTLLIQPMEATAAS
405 amino acids

FIG. 5 (continued)

SEQ ID NO: 6

```
1     atgcgctgcg ctccgaccgc aggcgctgct ctagtgctat gcgcagctactgcggggctg
61    ctgagcgcgc aagggcgccc tgcacagccg gagccgccgc gcttcgcatcctgggatgaa
121   atgaacttgc tggctcacgg gctgctgcag ctcggtcacg ggctgcgggaacacgtggag
181   cgcacccgtg gacagctggg cgcgctggaa cgccgcatgg ctgcctgcggtaacgcttgt
241   cagggccca  aggggacaga cccgaaggat agagtccccg aaggccaggctcctgagact
301   ctgcagagtt tacagactca actcaaggct cagaacagca agatccagcaactgttccag
361   aaggtagccc agcagcagag ataccctatca aagcagaatc tgagaatacagaatcttcag
421   agccagattg acctcttgac ccccacacac ctagacaatg gggtagacaagacttcgagg
481   ggaaagaggc ttcccaagat ggcccagctc attggcttga ctcccaacgccacccgctta
541   cacaggcctc cccgggactg ccaggaactc tttcaagaag gggagcggcacagtggactt
601   ttccagatcc agcctctggg atctccacca tttttggtca actgtgagatgacttcagat
661   ggaggctgga cggtgattca gagacgcctg aacggctctg tggacttcaatcagtcttgg
721   gaagcctaca aagatggctt cggagatccc caaggcgagt tctggctggcctagagaag
781   atgcacagca tcacagggga ccgaggaagc cagttggctg tgcagctccaggactgggat
841   ggcaatgcca aattgctcca atttcctatc catttggggg gtgaggacacagcctacagc
901   ctgcagctca ccgagcccac ggccaatgag ctgggtgcca ccaatgtttcccccaatggc
961   ctttccctgc cttctctac  ctgggaccaa gaccacgacc tccgaggggaccttaactgt
1021  gccaagagcc tctctggtgg ctggtggttt ggcacctgca gccattccaatctaaatgga
1081  caatacttcc actctattcc acggcaacag cagcagcgta aaaaggggatcttctggaaa
1141  acatgtaagg gccgctacta tccactacag gctaccaccc tgttgatccagcccatggag
1201  gctacagcag cctcttag
```

SEQ ID NO: 7

MRCAPTAGAALVLCAATAGLLSAQGRPAQPEPPRFASWDEMNLLAHGLLQLGHGLREHVERTRGQLGALERRMAACG
NACQGPKGKDAPFKDSEDRVPEGQTPETLQSLQTQLKAQNSKIQQLFQKVAQQQRYLSKQNLRIQNLQSQIDLLAPT
HLDNGVDKTSRGKRLPKMTQLIGLTPNATHLHRPPRDCQELFQEGERHSGLFQIQPLGSPPFLVNCEMTSDGGWTVI
QRRLNGSVDFNQSWEAYKDGFGDPQGEFWLGLEKMHSITGNRGSQLAVQLQDWDGNAKLLQFPIHLGGEDTAYSLQL
TEPTANELGATNVSPNGLSLPFSTWDQDHDLRGDLNCAKSLSGGWWFGTCSHSNLNGQYFHSIPRQRQERKKGIFWK
TWKGRYYPLQATTLLIQPMEATAAS
410 amino acids

FIG. 5 (continued)

SEQ ID NO: 8

```
   1    acgggctcca gatcttcttc tgcaccagag caagtctaag tctgagccggctccccaga
  61    actccagctg ctgggtcttg aactcctgcg ttccggagtc ctagcgttgctgcacccaag
 121    gccacccca  gaatcatgcg ctgcgctccg acagcaggcg ctgccctggtgctatgcgcg
 181    gctactgcgg ggcttttgag cgcgcaaggg cgccctgcac agccagagccaccgcgcttt
 241    gcatcctggg acgagatgaa cttgctggct cacgggctgc tacagctcggccatgggctg
 301    cgcgaacacg tggagcgcac ccgtgggcag ctgggcgcgc tggagcgccgcatggctgcc
 361    tgtggtaacg cttgtcaggg gcccaaggga aaagatgcac ccttcaaagactccgaggat
 421    agagtccctg aaggccagac tcctgagact ctgcagagtt tgcagactcagctcaaggct
 481    caaaacagca agatccagca attgttccag aaggtggccc agcagcagagatacctatca
 541    aagcagaatc tgagaataca gaatcttcag agccagatag acctcttggccccccacgcac
 601    ctagacaatg gagtagacaa gacttcgagg ggaaagaggc ttcccaagatgacccagctc
 661    attggcttga ctcccaacgc cacccactta cacaggccgc cccgggactgccaggaactc
 721    ttccaagaag gggagaggca cagtggactt ttccagatcc agcctctggggtctccacca
 781    tttttggtca actgtgagat gacttcagat ggaggctgga cagtgattcagagacgcctg
 841    aacggctctg tggacttcaa ccagtcctgg gaagcctaca aggatggcttcggagatccc
 901    caaggcgagt tctggctggg cctggaaaag atgcacagca tcacagggaaccgaggaagc
 961    caattggctg tgcagctcca ggactgggat ggcaatgcca aattgctccaatttcccatc
1021    catttggggg gtgaggacac agcctacagc ctgcagctca ctgagccacggccaatgag
1081    ctgggtgcca ccaatgtttc ccccaatggc ctttccctgc ccttctctacttgggaccaa
1141    gaccatgacc tccgtgggga ccttaactgt gccaagagcc tctctggtggctggtggttt
1201    ggtacctgta gccattccaa tctcaatgga caatacttcc actctatcccacggcaacgg
1261    caggagcgta aaaagggtat cttctggaaa acatggaagg gccgctactatcctctgcag
1321    gctaccaccc tgctgatcca gcccatgagg ctacagcag  cctcttagcctcctcactgg
1381    agcctggttc caggcctaag aagacagtga ctttggttgt ggcctgagatttggccatt
1441    ctctgctggg ggcaggagct ctaagtaggg ctatctgcgt cttgtggacaaagaagaagc
1501    ccgtaactgg agagactgga ggacccctt  tccgtgttgg ggtctgcaagcattgttgtc
1561    tgaaacagtc agagcaacag gaaacaaatg cccagatcc  agaaaacatgggctcgaggg
1621    gcactgaata tcacttctcg cctaccagag aagttgggga tgcagagggaccactacagt
1681    ccaactagct gggcccttaa tggcggactc agttatattg actgactggagacagggtgc
1741    caggagccct ggatacactc atggtgctgt tgtaggtgct gtggatgcacaggtgctaac
1801    tgtggttccc aggcacaact cacagcattc ttacaataaa acaacctcagaacaaaaaa
1861    aaaaaaaaa
```

SEQ ID NO: 9

MSGAPTAGAALMLCAATAVLLSAQGGPVQSKSPRFASWX$_{39}$X$_{40}$MNVLAHGLLQLGQGLREHAERTRSQLSALERRLSA
X$_{76}$GSAX$_{80}$QGTEGSTDLPLAPESRVDPEVLHSLQTQLKAQNSRIQQLFHKVAQQQRHLEKQHLRIQHLQSQFGLLDHK
HLDHEVAKPAX$_{161}$X$_{162}$X$_{163}$X$_{164}$LPEMAQPVDPAHNVSRLHRLPRDCQELFQVGERQSGLFEIQPQGSPPFLVNCKMTS
X$_{221}$GGWTVIQRRHDGSVDFNRPWEAYKAGFGDPHGEFWLGLEKVHSITGDRNSRLAVQLRDWDGNAELLQFSVHLGGE
DTAYSLQLTAPVAGQLGATTVPPSGLSVPFSTWDQDHDLRRDKNCAKSLSGGWWFGTCSHSNLNGQYFRSIPQQRQK
LKKGIFWKTWRGRYYPLQATTMLIQPMAAEAAS
406 amino acids

SEQ ID NO: 10

MSGAPTAGAALMLCAATAVLLSAQGGPVQSKSPRFASWX$_{39}$X$_{40}$MNVLAHGLLQLGQGLREHAERTRSQLSALERRLSA
X$_{76}$GSAX$_{80}$QGTEGSTDLPLAPESRVDPEVLHSLQTQLKAQNSRIQQLFHKVAQQQRHLEKQHLRIQHLQSQFGLLDHK
HLDHEVAKPAX$_{161}$X$_{162}$X$_{163}$X$_{164}$LPEMAQPVDPAHNVSRLHHGGWTVIQRRHDGSVDFNRPWEAYKAGFGDPHGEFWLG
LEKVHSITGDRNSRLAVQLRDWDGNAELLQFSVHLGGEDTAYSLQLTAPVAGQLGATTVPPSGLSVPFSTWDQDHDL
RRDKNCAKSLSGGWWFGTCSHSNLNGQYFRSIPQQRQKLKKGIFWKTWRGRYYPLQATTMLIQPMAAEAAS
368 amino acids

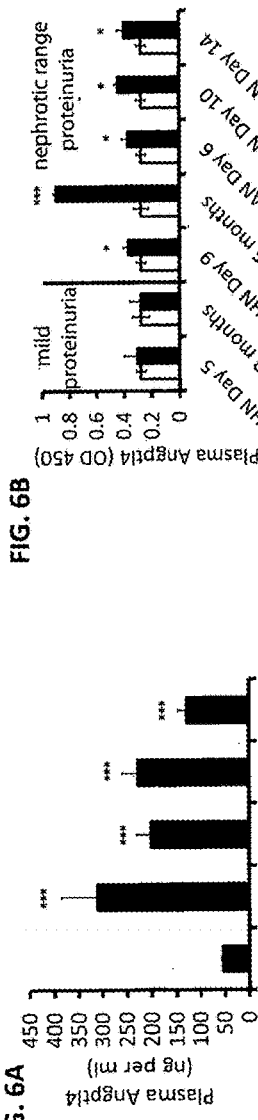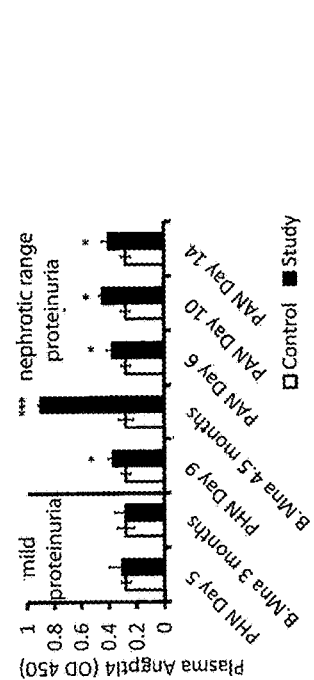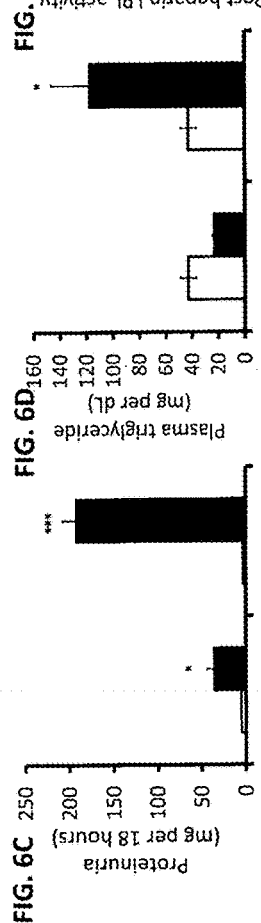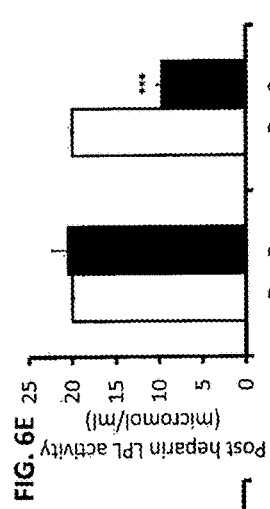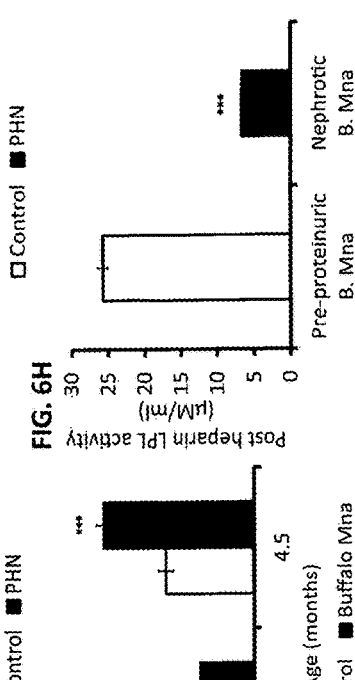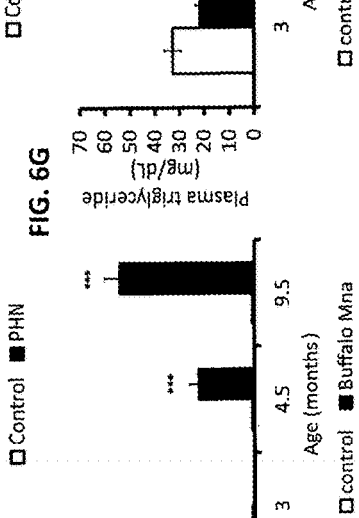
FIG. 6A, FIG. 6B, FIG. 6C, FIG. 6D, FIG. 6E, FIG. 6F, FIG. 6G, FIG. 6H

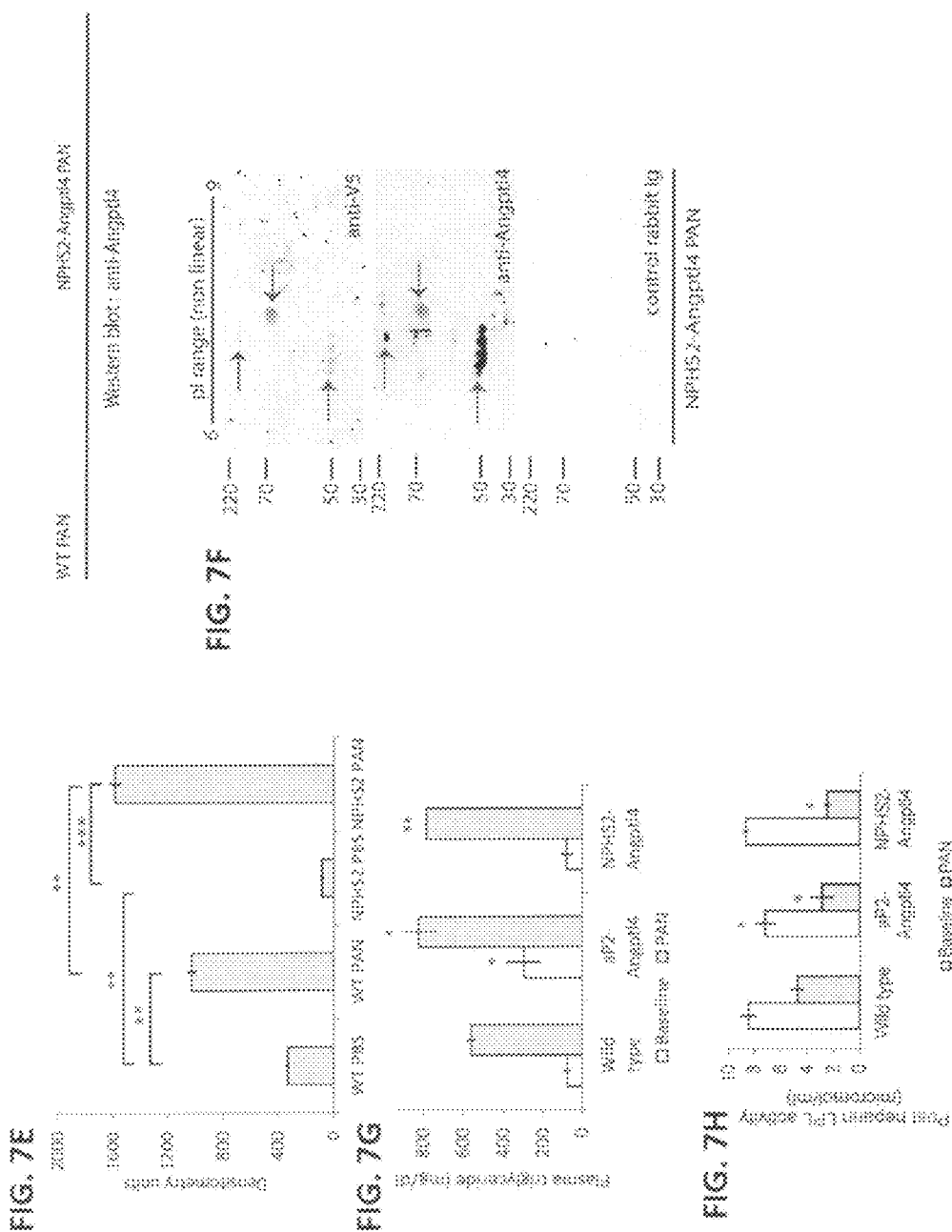

FIG. 10A
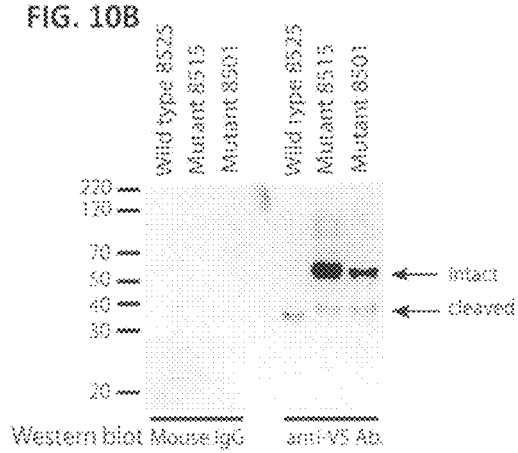
FIG. 10B
FIG. 10C
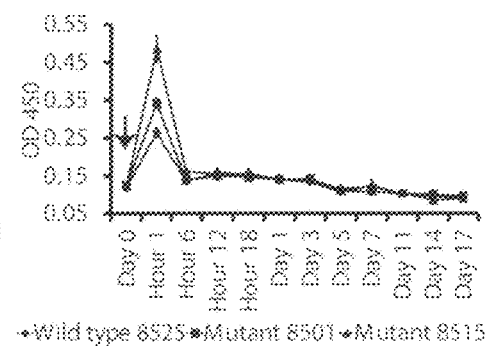
FIG. 10D
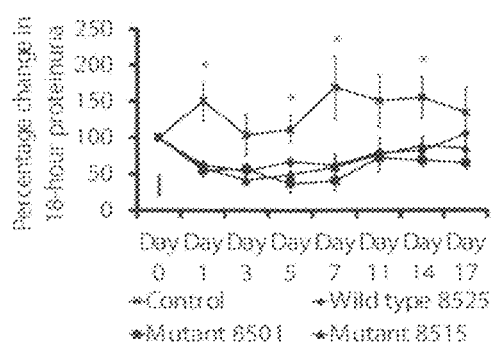
FIG. 10E
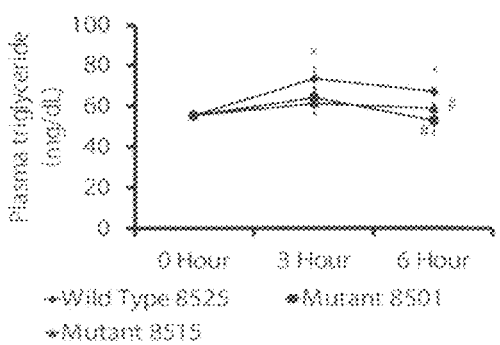

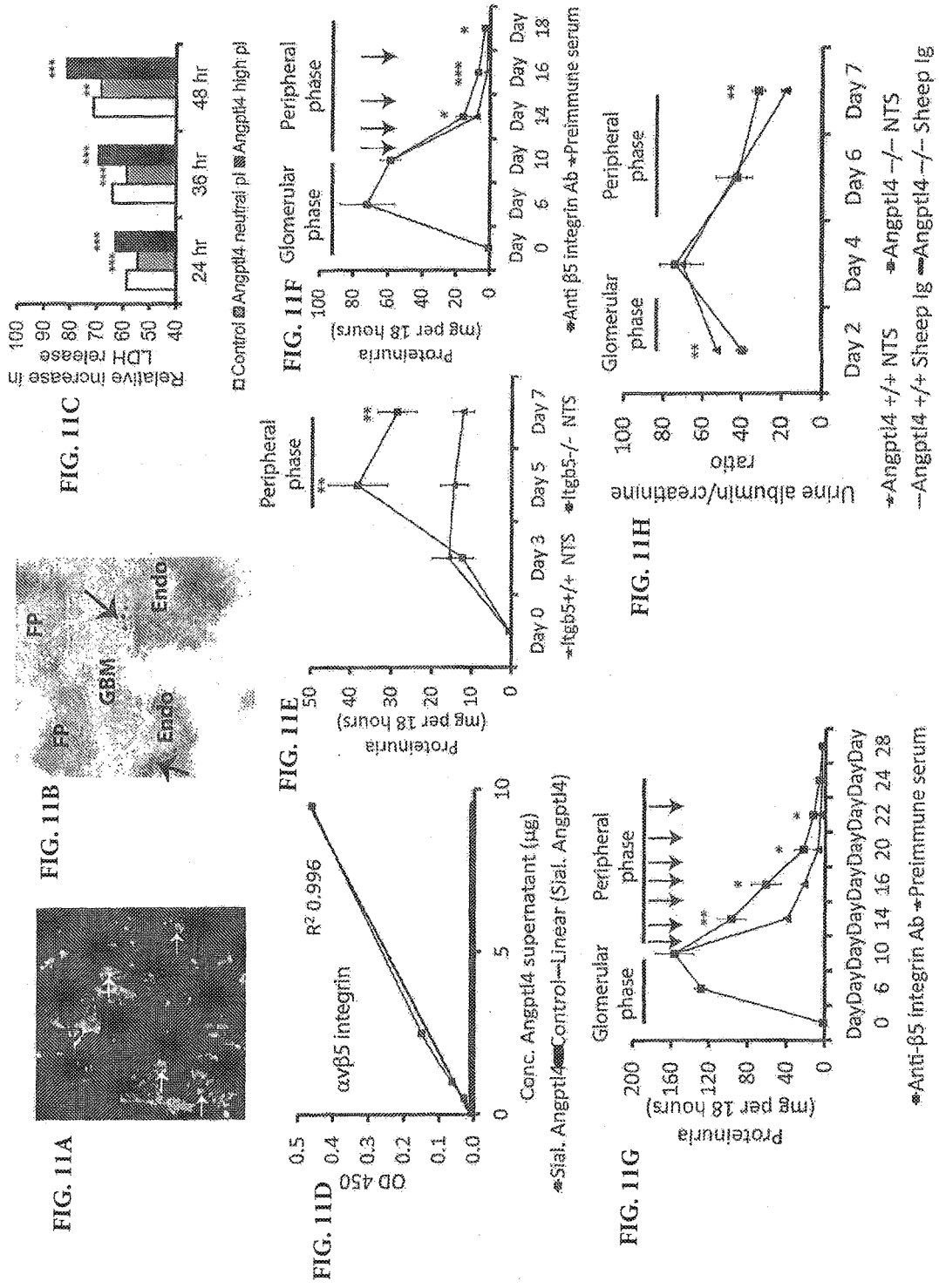

FIG. 17

| | Amino acid change | cDNA mutagenesis | |
|---|---|---|---|
| Wild type 8525 | 39 DE 40; 161 RRKR 164 | 115 GAC GAG 120   479 CC CGA AGA AAG AGG CT 494<br>　　　　D　E　　　　　　　　R　R　K　R | SEQ ID NO: 1 pos 161-164 |
| Mutant 8496 | 39 DK 40; 161 GAAG 164 | 115 GAC AAG 120   479 CC GGA GCA GCA GGA CT 494<br>　　　　D　K　　　　　　　　G　A　A　G | SEQ ID NO: 29 |
| Mutant 8501 | 39 DK 40; 161 GSGS 164 | 115 GAC AAG 120   479 CC GGA TCA GGA TCA CT 494<br>　　　　D　K　　　　　　　　G　S　G　S | SEQ ID NO: 80 |
| Mutant 8506 | 39 DK 40; 161 AAVV 164 | 115 GAC AAG 120   479 CC GCC GCC GTG GTG CT 494<br>　　　　D　K　　　　　　　　A　A　V　V | SEQ ID NO: 69 |
| Mutant 8511 | 39 DA 40; 161 GVVA 164 | 115 GAC GCA 120   479 CC GGC GTC GTC GCG CT 494<br>　　　　D　A　　　　　　　　G　V　V　A | SEQ ID NO: 49 |
| Mutant 8515 | 39 KE 40; 161 SGGG 164 | 115 AAG GAG 120   479 CC TCC GGC GGC GGC CT 494<br>　　　　K　E　　　　　　　　S　G　G　G | SEQ ID NO: 87 |
| Mutant 8520 | 39 AE 40; 161 VAVA 164 | 115 GCA GAG 120   479 CC GTC GCC GTG GCG CT 494<br>　　　　A　E　　　　　　　　V　A　V　A | SEQ ID NO: 90 |

SEQUENCE LISTING

<160> NUMBER OF SEQ ID NOS: 96

<210> SEQ ID NO 1
<211> LENGTH: 406
<212> TYPE: PRT
<213> ORGANISM: Homo sapiens

<400> SEQUENCE: 1

-continued

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
            115                 120                 125

His Leu Glu Lys Gln His Leu Arg Ile Gln His Leu Gln Ser Gln Phe
        130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365

Gln Gln Arg Gln Lys Leu Lys Lys Gly Ile Phe Trp Lys Thr Trp Arg
370                 375                 380

Gly Arg Tyr Tyr Pro Leu Gln Ala Thr Thr Met Leu Ile Gln Pro Met
385                 390                 395                 400

Ala Ala Glu Ala Ala Ser
                405
```

<210> SEQ ID NO 2
<211> LENGTH: 1967
<212> TYPE: DNA
<213> ORGANISM: Homo sapiens

<400> SEQUENCE: 2

| | | | | | |
|---|---|---|---|---|---|
| ataaaaaccg | tcctcgggcg | cggcggggag | aagccgagct | gagcggatcc | tcacacgact | 60 |
| gtgatccgat | tctttccagc | ggcttctgca | accaagcggg | tcttacccc | ggtcctccgc | 120 |
| gtctccagtc | ctcgcacctg | gaaccccaac | gtccccgaga | gtccccgaat | cccgctccc | 180 |
| aggctaccta | agaggatgag | cggtgctccg | acggccgggg | cagccctgat | gctctgcgcc | 240 |
| gccaccgccg | tgctactgag | cgctcagggc | ggacccgtgc | agtccaagtc | gccgcgcttt | 300 |
| gcgtcctggg | acgagatgaa | tgtcctggcg | cacggactcc | tgcagctcgg | ccaggggctg | 360 |
| cgcgaacacg | cggagcgcac | ccgcagtcag | ctgagcgcg | tggagcggcg | cctgagcgcg | 420 |
| tgcgggtccg | cctgtcaggg | aaccgagggg | tccaccgacc | tcccgttagc | ccctgagagc | 480 |
| cgggtggacc | ctgaggtcct | tcacagcctg | cagacacaac | tcaaggctca | gaacagcagg | 540 |
| atccagcaac | tcttccacaa | ggtggcccag | cagcagcggc | acctggagaa | gcagcacctg | 600 |
| cgaattcagc | atctgcaaag | ccagtttggc | ctcctggacc | acaagcacct | agaccatgag | 660 |
| gtggccaagc | ctgcccgaag | aaagaggctg | cccgagatgg | cccagccagt | tgacccggct | 720 |
| cacaatgtca | gccgcctgca | ccggctgccc | agggattgcc | aggagctgtt | ccaggttggg | 780 |
| gagaggcaga | gtggactatt | tgaaatccag | cctcaggggt | ctccgccatt | tttggtgaac | 840 |
| tgcaagatga | cctcagatgg | aggctggaca | gtaattcaga | ggcgccacga | tggctcagtg | 900 |
| gacttcaacc | ggccctggga | agcctacaag | gcggggtttg | gggatcccca | cggcgagttc | 960 |
| tggctgggtc | tggagaaggt | gcatagcatc | acggggacc | gcaacagccg | cctggccgtg | 1020 |
| cagctgcggg | actgggatgg | caacgccgag | ttgctgcagt | tctccgtgca | cctgggtggc | 1080 |
| gaggacacgg | cctatagcct | gcagctcact | gcacccgtgg | ccggccagct | gggcgccacc | 1140 |
| accgtcccac | ccagcggcct | ctccgtaccc | ttctccactt | gggaccagga | tcacgacctc | 1200 |
| cgcagggaca | agaactgcgc | caagagcctc | tctggaggct | ggtggtttgg | cacctgcagc | 1260 |
| cattccaacc | tcaacggcca | gtacttccgc | tccatcccac | agcagcggca | gaagcttaag | 1320 |
| aagggaatct | tctggaagac | ctggcggggc | cgctactacc | cgctgcaggc | caccaccatg | 1380 |
| ttgatccagc | ccatggcagc | agaggcagcc | tcctagcgtc | ctggctgggc | ctggtcccag | 1440 |
| gcccacgaaa | gacggtgact | cttggctctg | cccgaggatg | tggccgttcc | ctgcctgggc | 1500 |
| aggggctcca | aggaggggcc | atctggaaac | ttgtggacag | agaagaagac | cacgactgga | 1560 |
| gaagccccct | ttctgagtgc | aggggggctg | catgcgttgc | ctcctgagat | cgaggctgca | 1620 |
| ggatatgctc | agactctaga | ggcgtggacc | aaggggcatg | gagcttcact | ccttgctggc | 1680 |
| cagggagttg | gggactcaga | gggaccactt | ggggccagcc | agactggcct | caatggcgga | 1740 |
| ctcagtcaca | ttgactgacg | gggaccaggg | cttgtgtggg | tcgagagcgc | cctcatggtg | 1800 |
| ctggtgctgt | tgtgtgtagg | tcccctgggg | acacaagcag | gcgccaatgg | tatctgggcg | 1860 |
| gagctcacag | agttcttgga | ataaaagcaa | cctcagaaca | cttaaaaaaa | aaaaaaaaa | 1920 |
| aaaaaaaaaa | aaaaaaaaaa | aaaaaaaaa | aaaaaaaaaa | aaaaaaa | | 1967 |

<210> SEQ ID NO 3
<211> LENGTH: 368
<212> TYPE: PRT
<213> ORGANISM: Homo sapiens

<400> SEQUENCE: 3

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg His Gly Gly Trp Thr Val Ile Gln Arg Arg
            180                 185                 190

His Asp Gly Ser Val Asp Phe Asn Arg Pro Trp Glu Ala Tyr Lys Ala
        195                 200                 205

Gly Phe Gly Asp Pro His Gly Glu Phe Trp Leu Gly Leu Glu Lys Val
    210                 215                 220

His Ser Ile Thr Gly Asp Arg Asn Ser Arg Leu Ala Val Gln Leu Arg
225                 230                 235                 240

Asp Trp Asp Gly Asn Ala Glu Leu Leu Gln Phe Ser Val His Leu Gly
                245                 250                 255

Gly Glu Asp Thr Ala Tyr Ser Leu Gln Leu Thr Ala Pro Val Ala Gly
            260                 265                 270

Gln Leu Gly Ala Thr Thr Val Pro Pro Ser Gly Leu Ser Val Pro Phe
        275                 280                 285

Ser Thr Trp Asp Gln Asp His Asp Leu Arg Arg Asp Lys Asn Cys Ala
    290                 295                 300

Lys Ser Leu Ser Gly Gly Trp Trp Phe Gly Thr Cys Ser His Ser Asn
305                 310                 315                 320

Leu Asn Gly Gln Tyr Phe Arg Ser Ile Pro Gln Gln Arg Gln Lys Leu
                325                 330                 335

Lys Lys Gly Ile Phe Trp Lys Thr Trp Arg Gly Arg Tyr Tyr Pro Leu
            340                 345                 350

Gln Ala Thr Thr Met Leu Ile Gln Pro Met Ala Ala Glu Ala Ala Ser
        355                 360                 365
```

<210> SEQ ID NO 4
<211> LENGTH: 1853
<212> TYPE: DNA
<213> ORGANISM: Homo sapiens

<400> SEQUENCE: 4

-continued

```
ataaaaaccg tcctcgggcg cggcggggag aagccgagct gagcggatcc tcacacgact     60
gtgatccgat tctttccagc ggcttctgca accaagcggg tcttacccccc ggtcctccgc    120
gtctccagtc ctcgcacctg aaccccaac gtccccgaga gtccccgaat cccgctccc     180
aggctaccta agaggatgag cggtgctccg acggccgggg cagccctgat gctctgcgcc    240
gccaccgccg tgctactgag cgctcagggc ggacccgtgc agtccaagtc gccgcgcttt    300
gcgtcctggg acgagatgaa tgtcctggcg cacggactcc tgcagctcgg ccaggggctg    360
cgcgaacacg cggagcgcac ccgcagtcag ctgagcgcgc tggagcggcg cctgagcgcg    420
tgcgggtccg cctgtcaggg aaccgagggg tccaccgacc tcccgttagc ccctgagagc    480
cgggtggacc ctgaggtcct tcacagcctg cagacacaac tcaaggctca gaacagcagg    540
atccagcaac tcttccacaa ggtggcccag cagcagcggc acctggagaa gcagcacctg    600
cgaattcagc atctgcaaag ccagtttggc ctcctggacc acaagcacct agaccatgag    660
gtggccaagc tgcccgaag aaagaggctg cccgagatgg cccagccagt tgacccggct    720
cacaatgtca gccgcctgca ccatggaggc tggacagtaa ttcagaggcg ccacgatggc    780
tcagtggact caaccggcc ctgggaagcc tacaaggcgg ggtttgggga tccccacggc    840
gagttctggc tgggtctgga aaggtgcat agcatcacgg gggaccgcaa cagccgcctg    900
gccgtgcagc tgcgggactg ggatggcaac gccgagttgc tgcagttctc cgtgcacctg    960
ggtggcgagg acacggccta tagcctgcag ctcactgcac ccgtggccgg ccagctgggc   1020
gccaccaccg tcccacccag cggcctctcc gtacccttct ccacttggga ccaggatcac   1080
gacctccgca gggacaagaa ctgcgccaag agcctctctg gaggctggtg gtttggcacc   1140
tgcagccatt ccaacctcaa cggccagtac ttccgctcca tcccacagca gcggcagaag   1200
cttaagaagg gaatcttctg gaagacctgg cggggccgct actaccgct gcaggccacc   1260
accatgttga tccagcccat ggcagcagag gcagcctcct agcgtcctgg ctgggcctgg   1320
tcccaggccc acgaaagacg gtgactcttg gctctgcccg aggatgtggc cgttccctgc   1380
ctgggcaggg gctccaagga ggggccatct ggaaacttgt ggacagagaa gaagaccacg   1440
actggagaag ccccctttct gagtgcaggg gggctgcatg cgttgcctcc tgagatcgag   1500
gctgcaggat atgctcagac tctagaggcg tggaccaagg ggcatggagc ttcactcctt   1560
gctggccagg gagttgggga ctcagaggga ccacttgggg ccagccagac tggcctcaat   1620
ggcggactca gtcacattga ctgacgggga ccagggcttg tgtgggtcga gagcgccctc   1680
atggtgctgg tgctgttgtg tgtaggtccc ctggggacac aagcaggcgc caatggtatc   1740
tgggcggagc tcacagagtt cttggaataa agcaacctc agaacactta aaaaaaaaaa   1800
aaaaaaaaaa aaaaaaaaaa aaaaaaaaaa aaaaaaaaaa aaaaaaaaaa aaa          1853
```

<210> SEQ ID NO 5
<211> LENGTH: 405
<212> TYPE: PRT
<213> ORGANISM: Rattus norvegicus

<400> SEQUENCE: 5

```
Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45
```

Leu Gln Leu Gly His Gly Leu Arg Glu His Val Glu Arg Thr Arg Gly
 50                  55                  60

Gln Leu Gly Ala Leu Glu Arg Arg Met Ala Ala Cys Gly Asn Ala Cys
 65                  70                  75                  80

Gln Gly Pro Lys Gly Thr Asp Pro Lys Asp Arg Val Pro Glu Gly Gln
                 85                  90                  95

Ala Pro Glu Thr Leu Gln Ser Leu Gln Thr Gln Leu Lys Ala Gln Asn
                100                 105                 110

Ser Lys Ile Gln Gln Leu Phe Gln Lys Val Ala Gln Gln Gln Arg Tyr
            115                 120                 125

Leu Ser Lys Gln Asn Leu Arg Ile Gln Asn Leu Gln Ser Gln Ile Asp
130                 135                 140

Leu Leu Thr Pro Thr His Leu Asp Asn Gly Val Asp Lys Thr Ser Arg
145                 150                 155                 160

Gly Lys Arg Leu Pro Lys Met Ala Gln Leu Ile Gly Leu Thr Pro Asn
                165                 170                 175

Ala Thr Arg Leu His Arg Pro Pro Arg Asp Cys Gln Glu Leu Phe Gln
                180                 185                 190

Glu Gly Glu Arg His Ser Gly Leu Phe Gln Ile Gln Pro Leu Gly Ser
            195                 200                 205

Pro Pro Phe Leu Val Asn Cys Glu Met Thr Ser Asp Gly Gly Trp Thr
210                 215                 220

Val Ile Gln Arg Arg Leu Asn Gly Ser Val Asp Phe Asn Gln Ser Trp
225                 230                 235                 240

Glu Ala Tyr Lys Asp Gly Phe Gly Asp Pro Gln Gly Glu Phe Trp Leu
                245                 250                 255

Gly Leu Glu Lys Met His Ser Ile Thr Gly Asp Arg Gly Ser Gln Leu
                260                 265                 270

Ala Val Gln Leu Gln Asp Trp Asp Gly Asn Ala Lys Leu Leu Gln Phe
            275                 280                 285

Pro Ile His Leu Gly Gly Glu Asp Thr Ala Tyr Ser Leu Gln Leu Thr
290                 295                 300

Glu Pro Thr Ala Asn Glu Leu Gly Ala Thr Asn Val Ser Pro Asn Gly
305                 310                 315                 320

Leu Ser Leu Pro Phe Ser Thr Trp Asp Gln Asp His Asp Leu Arg Gly
                325                 330                 335

Asp Leu Asn Cys Ala Lys Ser Leu Ser Gly Gly Trp Trp Phe Gly Thr
                340                 345                 350

Cys Ser His Ser Asn Leu Asn Gly Gln Tyr Phe His Ser Ile Pro Arg
            355                 360                 365

Gln Arg Gln Gln Arg Lys Lys Gly Ile Phe Trp Lys Thr Trp Lys Gly
370                 375                 380

Arg Tyr Tyr Pro Leu Gln Ala Thr Thr Leu Leu Ile Gln Pro Met Glu
385                 390                 395                 400

Ala Thr Ala Ala Ser
            405

<210> SEQ ID NO 6
<211> LENGTH: 1218
<212> TYPE: DNA
<213> ORGANISM: Rattus norvegicus

<400> SEQUENCE: 6
atgcgctgcg ctccgaccgc aggcgctgct ctagtgctat gcgcagctac tgcggggctg      60

```
ctgagcgcgc aagggcgccc tgcacagccg gagccgccgc gcttcgcatc ctgggatgaa    120
atgaacttgc tggctcacgg gctgctgcag ctcggtcacg gctgcgggga acacgtggag    180
cgcacccgtg gacagctggg cgcgctggaa cgccgcatgg ctgcctgcgg taacgcttgt    240
caggggccca aggggacaga cccgaaggat agagtcccg aaggccaggc tcctgagact     300
ctgcagagtt tacagactca actcaaggct cagaacagca agatccagca actgttccag    360
aaggtagccc agcagcagag atacctatca aagcagaatc tgagaataca gaatcttcag    420
agccagattg acctcttgac ccccacacac ctagacaatg gggtagacaa gacttcgagg    480
ggaaagaggc ttcccaagat ggcccagctc attggcttga ctcccaacgc cacccgctta    540
cacaggcctc cccgggactg ccaggaactc tttcaagaag gggagcggca cagtggactt    600
ttccagatcc agcctctggg atctccacca tttttggtca actgtgagat gacttcagat    660
ggaggctgga cggtgattca gagacgcctg aacggctctg tggacttcaa tcagtcttgg    720
gaagcctaca agatggcttt cggagatccc caaggcgagt ctggctgggg cctagagaag    780
atgcacagca tcacagggga ccgaggaagc cagttggctg tgcagctcca ggactgggat    840
ggcaatgcca aattgctcca atttcctatc catttggggg gtgaggacac agcctacagc    900
ctgcagctca ccgagcccac ggccaatgag ctgggtgcca ccaatgtttc ccccaatggc    960
ctttccctgc ccttctctac ctgggaccaa gaccacgacc tccgagggga ccttaactgt    1020
gccaagagcc tctctggtgg ctggtggttt ggcacctgca gccattccaa tctaaatgga    1080
caatacttcc actctattcc acggcaacgg cagcagcgta aaaagggat cttctggaaa    1140 acatggaagg gccgctacta tccactacag gctaccaccc tgttgatcca gcccatggag    1200
gctacagcag cctcttag                                                 1218

<210> SEQ ID NO 7
<211> LENGTH: 410
<212> TYPE: PRT
<213> ORGANISM: Mus musculus

<400> SEQUENCE: 7

Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly Pro Lys Gly Lys Asp Ala Pro Phe Lys Asp Ser Glu Asp Arg
                85                  90                  95

Val Pro Glu Gly Gln Thr Pro Glu Thr Leu Gln Ser Leu Gln Thr Gln
            100                 105                 110

Leu Lys Ala Gln Asn Ser Lys Ile Gln Gln Leu Phe Gln Lys Val Ala
        115                 120                 125

Gln Gln Gln Arg Tyr Leu Ser Lys Gln Asn Leu Arg Ile Gln Asn Leu
    130                 135                 140

Gln Ser Gln Ile Asp Leu Leu Ala Pro Thr His Leu Asp Asn Gly Val
145                 150                 155                 160
```

Asp Lys Thr Ser Arg Gly Lys Arg Leu Pro Lys Met Thr Gln Leu Ile
            165                 170                 175

Gly Leu Thr Pro Asn Ala Thr His Leu His Arg Pro Pro Arg Asp Cys
            180                 185                 190

Gln Glu Leu Phe Gln Glu Gly Glu Arg His Ser Gly Leu Phe Gln Ile
            195                 200                 205

Gln Pro Leu Gly Ser Pro Pro Phe Leu Val Asn Cys Glu Met Thr Ser
            210                 215                 220

Asp Gly Gly Trp Thr Val Ile Gln Arg Arg Leu Asn Gly Ser Val Asp
225                 230                 235                 240

Phe Asn Gln Ser Trp Glu Ala Tyr Lys Asp Gly Phe Gly Asp Pro Gln
            245                 250                 255

Gly Glu Phe Trp Leu Gly Leu Glu Lys Met His Ser Ile Thr Gly Asn
            260                 265                 270

Arg Gly Ser Gln Leu Ala Val Gln Leu Gln Asp Trp Asp Gly Asn Ala
            275                 280                 285

Lys Leu Leu Gln Phe Pro Ile His Leu Gly Gly Glu Asp Thr Ala Tyr
            290                 295                 300

Ser Leu Gln Leu Thr Glu Pro Thr Ala Asn Glu Leu Gly Ala Thr Asn
305                 310                 315                 320

Val Ser Pro Asn Gly Leu Ser Leu Pro Phe Ser Thr Trp Asp Gln Asp
            325                 330                 335

His Asp Leu Arg Gly Asp Leu Asn Cys Ala Lys Ser Leu Ser Gly Gly
            340                 345                 350

Trp Trp Phe Gly Thr Cys Ser His Ser Asn Leu Asn Gly Gln Tyr Phe
            355                 360                 365

His Ser Ile Pro Arg Gln Arg Gln Glu Arg Lys Lys Gly Ile Phe Trp
            370                 375                 380

Lys Thr Trp Lys Gly Arg Tyr Tyr Pro Leu Gln Ala Thr Thr Leu Leu
385                 390                 395                 400

Ile Gln Pro Met Glu Ala Thr Ala Ala Ser
            405                 410

<210> SEQ ID NO 8
<211> LENGTH: 1869
<212> TYPE: DNA
<213> ORGANISM: Mus musculus

<400> SEQUENCE: 8
acgggctcca gatcttcttc tgcaccagag caagtctaag tctgagccgg ctcccccaga      60
actccagctg ctgggtcttg aactcctgcg ttccggagtc ctagcgttgc tgcacccaag     120
gccaccccca gaatcatgcg ctgcgctccg acagcaggcg ctgccctggt gctatgcgcg     180
gctactgcgg ggcttttgag cgcgcaaggg cgccctgcac agccagagcc accgcgcttt     240
gcatcctggg acgagatgaa cttgctggct cacgggctgc tacagctcgg ccatgggctg     300
cgcgaacacg tggagcgcac ccgtgggcag ctgggcgcgc tggagcgccg catggctgcc     360
tgtggtaacg cttgtcaggg gcccaaggga aaagatgcac ccttcaaaga ctccgaggat     420
agagtccctg aaggccagac tcctgagact ctgcagagtt tgcagactca gctcaaggct     480
caaaacagca gatccagca attgttccag aaggtggccc agcagcagag atacctatca     540
aagcagaatc tgagaataca gaatcttcag agccagatag acctcttggc ccccacgcac     600
ctagacaatg gagtagacaa gacttcgagg ggaaagaggc ttcccaagat gacccagctc     660
attggcttga ctcccaacgc cacccactta cacaggccgc ccgggactgc caggaactc      720

-continued

```
ttccaagaag gggagaggca cagtggactt ttccagatcc agcctctggg gtctccacca      780
tttttggtca actgtgagat gacttcagat ggaggctgga cagtgattca gagacgcctg      840
aacggctctg tggacttcaa ccagtcctgg gaagcctaca aggatggctt cggagatccc      900
caaggcgagt tctggctggg cctggaaaag atgcacagca tcacagggaa ccgaggaagc      960
caattggctg tgcagctcca ggactgggat ggcaatgcca aattgctcca atttcccatc     1020
catttggggg gtgaggacac agcctacagc ctgcagctca ctgagcccac ggccaatgag     1080
ctgggtgcca ccaatgtttc ccccaatggc ctttccctgc ccttctctac ttgggaccaa     1140
gaccatgacc tccgtgggga ccttaactgt gccaagagcc tctctggtgg ctggtggttt     1200
ggtacctgta gccattccaa tctcaatgga caatacttcc actctatccc acggcaacgg     1260
caggagcgta aaaagggtat cttctggaaa acatggaagg gccgctacta tcctctgcag     1320
gctaccaccc tgctgatcca gcccatggag gctacagcag cctcttagcc tcctcactgg     1380
agcctggttc caggcctaag aagacagtga ctttggttgt ggccctgaga tttggccatt     1440
ctctgctggg ggcaggagct ctaagtaggg ctatctgcgt cttgtggaca aagaagaagc     1500
ccgtaactgg agagactgga ggacccctttt tccgtgttgg ggtctgcaag cattgttgtc     1560
tgaaacagtc agagcaacag gaaacaaatg cccagatcc agaaacatg ggctcgaggg       1620 gcactgaata tcacttctcg cctaccagag aagttgggga tgcagaggga ccactacagt     1680
ccaactagct gggcccttaa tggcggactc agtcatattg actgactgga gacagggtgc     1740
caggagccct ggatacactc atggtgctgt tgtaggtgct gtggatgcac aggtgctaac     1800
tgtggttccc aggcacaact cacagcattc ttacaataaa aacaacctca gaacaaaaaa     1860
aaaaaaaaa                                                             1869
```

```
<210> SEQ ID NO 9
<211> LENGTH: 406
<212> TYPE: PRT
<213> ORGANISM: Homo sapiens
<220> FEATURE:
<221> NAME/KEY: MISC_FEATURE
<222> LOCATION: (39)..(39)
<223> OTHER INFORMATION: x = A, K, E or D
<220> FEATURE:
<221> NAME/KEY: MISC_FEATURE
<222> LOCATION: (40)..(40)
<223> OTHER INFORMATION: x = A, K, E or D
<220> FEATURE:
<221> NAME/KEY: MISC_FEATURE
<222> LOCATION: (76)..(76)
<223> OTHER INFORMATION: x = C, A or S
<220> FEATURE:
<221> NAME/KEY: MISC_FEATURE
<222> LOCATION: (80)..(80)
<223> OTHER INFORMATION: x = C, A or S
<220> FEATURE:
<221> NAME/KEY: MISC_FEATURE
<222> LOCATION: (161)..(161)
<223> OTHER INFORMATION: x = D, R, K, G, A, V or S
<220> FEATURE:
<221> NAME/KEY: MISC_FEATURE
<222> LOCATION: (162)..(162)
<223> OTHER INFORMATION: x = D, R, K, G, A, V or S
<220> FEATURE:
<221> NAME/KEY: MISC_FEATURE
<222> LOCATION: (163)..(163)
<223> OTHER INFORMATION: x = D, R, K, G, A, V or S
<220> FEATURE:
<221> NAME/KEY: MISC_FEATURE
<222> LOCATION: (164)..(164)
<223> OTHER INFORMATION: x = D, R, K, G, A, V or S
<220> FEATURE:
```

<221> NAME/KEY: misc_feature
<222> LOCATION: (221)..(221)
<223> OTHER INFORMATION: Xaa can be any naturally occurring amino acid

<400> SEQUENCE: 9

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Xaa Xaa Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Xaa Gly Ser Ala Xaa
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Xaa Xaa Xaa Xaa Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Xaa Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365

Gln Gln Arg Gln Lys Leu Lys Lys Gly Ile Phe Trp Lys Thr Trp Arg
    370                 375                 380

Gly Arg Tyr Tyr Pro Leu Gln Ala Thr Thr Met Leu Ile Gln Pro Met
```

```
                385                 390                 395                 400
Ala Ala Glu Ala Ala Ser
                405

<210> SEQ ID NO 10
<211> LENGTH: 368
<212> TYPE: PRT
<213> ORGANISM: Homo sapiens
<220> FEATURE:
<221> NAME/KEY: MISC_FEATURE
<222> LOCATION: (39)..(39)
<223> OTHER INFORMATION: x = A, K, D or E
<220> FEATURE:
<221> NAME/KEY: MISC_FEATURE
<222> LOCATION: (40)..(40)
<223> OTHER INFORMATION: x = A, K, D or E
<220> FEATURE:
<221> NAME/KEY: MISC_FEATURE
<222> LOCATION: (76)..(76)
<223> OTHER INFORMATION: x = C, A or S
<220> FEATURE:
<221> NAME/KEY: MISC_FEATURE
<222> LOCATION: (80)..(80)
<223> OTHER INFORMATION: x = S, A or C
<220> FEATURE:
<221> NAME/KEY: MISC_FEATURE
<222> LOCATION: (161)..(161)
<223> OTHER INFORMATION: x = D, R, K, G, A, V or S
<220> FEATURE:
<221> NAME/KEY: MISC_FEATURE
<222> LOCATION: (162)..(162)
<223> OTHER INFORMATION: x = D, R, K, G, A, V or S
<220> FEATURE:
<221> NAME/KEY: MISC_FEATURE
<222> LOCATION: (163)..(163)
<223> OTHER INFORMATION: x = D, R, K, G, A, V or S
<220> FEATURE:
<221> NAME/KEY: MISC_FEATURE
<222> LOCATION: (164)..(164)
<223> OTHER INFORMATION: x = D, R, K, G, A, V or S

<400> SEQUENCE: 10

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Xaa Xaa Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Xaa Gly Ser Ala Xaa
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Xaa Xaa Xaa Xaa Leu Pro Glu Met Ala Gln Pro Val Asp Pro Ala His
                165                 170                 175

Asn Val Ser Arg Leu His Arg Gly Gly Trp Thr Val Ile Gln Arg Arg
```

```
                    180                 185                 190
His Asp Gly Ser Val Asp Phe Asn Arg Pro Trp Glu Ala Tyr Lys Ala
            195                 200                 205

Gly Phe Gly Asp Pro His Gly Glu Phe Trp Leu Gly Leu Glu Lys Val
        210                 215                 220

His Ser Ile Thr Gly Asp Arg Asn Ser Arg Leu Ala Val Gln Leu Arg
225                 230                 235                 240

Asp Trp Asp Gly Asn Ala Glu Leu Leu Gln Phe Ser Val His Leu Gly
                245                 250                 255

Gly Glu Asp Thr Ala Tyr Ser Leu Gln Leu Thr Ala Pro Val Ala Gly
            260                 265                 270

Gln Leu Gly Ala Thr Thr Val Pro Pro Ser Gly Leu Ser Val Pro Phe
        275                 280                 285

Ser Thr Trp Asp Gln Asp His Asp Leu Arg Arg Asp Lys Asn Cys Ala
    290                 295                 300

Lys Ser Leu Ser Gly Gly Trp Trp Phe Gly Thr Cys Ser His Ser Asn
305                 310                 315                 320

Leu Asn Gly Gln Tyr Phe Arg Ser Ile Pro Gln Gln Arg Gln Lys Leu
                325                 330                 335

Lys Lys Gly Ile Phe Trp Lys Thr Trp Arg Gly Arg Tyr Tyr Pro Leu
            340                 345                 350

Gln Ala Thr Thr Met Leu Ile Gln Pro Met Ala Ala Glu Ala Ala Ser
        355                 360                 365

<210> SEQ ID NO 11
<211> LENGTH: 22
<212> TYPE: DNA
<213> ORGANISM: Artificial Sequence
<220> FEATURE:
<223> OTHER INFORMATION: PCR Primer

<400> SEQUENCE: 11
tctgggatct ccaccatttt tg                                          22

<210> SEQ ID NO 12
<211> LENGTH: 18
<212> TYPE: DNA
<213> ORGANISM: Artificial Sequence
<220> FEATURE:
<223> OTHER INFORMATION: PCR Primer

<400> SEQUENCE: 12
tcaccgtcca gcctccat                                               18

<210> SEQ ID NO 13
<211> LENGTH: 18
<212> TYPE: DNA
<213> ORGANISM: Artificial Sequence
<220> FEATURE:
<223> OTHER INFORMATION: Probe

<400> SEQUENCE: 13
caactgtgag atgacttc                                               18

<210> SEQ ID NO 14
<211> LENGTH: 17
<212> TYPE: DNA
<213> ORGANISM: Artificial Sequence
<220> FEATURE:
<223> OTHER INFORMATION: PCR Primer
```

<400> SEQUENCE: 14
cgccacccgc ttacaca                                                    17

<210> SEQ ID NO 15
<211> LENGTH: 22
<212> TYPE: DNA
<213> ORGANISM: Artificial Sequence
<220> FEATURE:
<223> OTHER INFORMATION: PCR Primer

<400> SEQUENCE: 15
cagaggctgg atctggaaaa gt                                              22

<210> SEQ ID NO 16
<211> LENGTH: 15
<212> TYPE: DNA
<213> ORGANISM: Artificial Sequence
<220> FEATURE:
<223> OTHER INFORMATION: Probe

<400> SEQUENCE: 16
tgccaggaac tcttt                                                      15

<210> SEQ ID NO 17
<211> LENGTH: 23
<212> TYPE: DNA
<213> ORGANISM: Artificial Sequence
<220> FEATURE:
<223> OTHER INFORMATION: PCR Primer

<400> SEQUENCE: 17
tacaggctac caccctgttg atc                                             23

<210> SEQ ID NO 18
<211> LENGTH: 17
<212> TYPE: DNA
<213> ORGANISM: Artificial Sequence
<220> FEATURE:
<223> OTHER INFORMATION: PCR Primer

<400> SEQUENCE: 18
aaccgcgggc cctctag                                                    17

<210> SEQ ID NO 19
<211> LENGTH: 17
<212> TYPE: DNA
<213> ORGANISM: Artificial Sequence
<220> FEATURE:
<223> OTHER INFORMATION: PCR Primer

<400> SEQUENCE: 19
ccatggaggc tacagca                                                    17

<210> SEQ ID NO 20
<211> LENGTH: 27
<212> TYPE: DNA
<213> ORGANISM: Artificial Sequence
<220> FEATURE:
<223> OTHER INFORMATION: PCR Primer

<400> SEQUENCE: 20
cttgaaggga ttgaaaagat aattagc                                         27

<210> SEQ ID NO 21
<211> LENGTH: 24

```
<212> TYPE: DNA
<213> ORGANISM: Artificial Sequence
<220> FEATURE:
<223> OTHER INFORMATION: PCR Primer

<400> SEQUENCE: 21
ccatgagtca gaaaagcatt gaac                                              24

<210> SEQ ID NO 22
<211> LENGTH: 17
<212> TYPE: DNA
<213> ORGANISM: Artificial Sequence
<220> FEATURE:
<223> OTHER INFORMATION: Probe

<400> SEQUENCE: 22
aggtgagcat tttcctg                                                      17

<210> SEQ ID NO 23
<211> LENGTH: 98
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(32)
<223> OTHER INFORMATION: Xaa can be any naturally occurring amino acid
<220> FEATURE:
<221> NAME/KEY: misc_feature
<222> LOCATION: (39)..(55)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(74)
<223> OTHER INFORMATION: Xaa can be any naturally occurring amino acid
<220> FEATURE:
<221> NAME/KEY: misc_feature
<222> LOCATION: (76)..(78)
<223> OTHER INFORMATION: Xaa can be any naturally occurring amino acid
<220> FEATURE:
```

```
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (86)..(98)
<223> OTHER INFORMATION: Xaa can be any naturally occurring amino acid

<400> SEQUENCE: 23

Met Xaa Xaa Ala Xaa Thr Ala Gly Ala Ala Leu Xaa Leu Cys Ala Ala
1               5                   10                  15

Thr Ala Xaa Leu Leu Ser Ala Gln Gly Xaa Pro Xaa Gln Xaa Xaa Xaa
            20                  25                  30

Pro Arg Phe Ala Ser Trp Xaa Xaa Xaa Xaa Xaa Xaa Xaa Xaa Xaa Xaa
        35                  40                  45

Xaa Xaa Xaa Xaa Xaa Xaa Xaa Arg Glu His Xaa Glu Arg Thr Arg Xaa
    50                  55                  60

Gln Leu Xaa Ala Leu Glu Arg Xaa Xaa Xaa Ala Xaa Xaa Xaa Ala Xaa
65                  70                  75                  80

Gln Gly Xaa Xaa Gly Xaa Xaa Xaa Xaa Xaa Xaa Xaa Xaa Xaa Xaa Xaa
                85                  90                  95

Xaa Xaa

<210> SEQ ID NO 24
<211> LENGTH: 85
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (46)..(47)
<223> OTHER INFORMATION: Xaa can be any naturally occurring amino acid
<220> FEATURE:
<221> NAME/KEY: misc_feature
<222> LOCATION: (50)..(52)
<223> OTHER INFORMATION: Xaa can be any naturally occurring amino acid
```

-continued

```
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(78)
<223> OTHER INFORMATION: Xaa can be any naturally occurring amino acid
<220> FEATURE:
<221> NAME/KEY: misc_feature
<222> LOCATION: (80)..(82)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid

<400> SEQUENCE: 24

Pro Glu Xaa Leu Xaa Ser Leu Gln Thr Gln Leu Lys Ala Gln Asn Ser
1               5                   10                  15

Xaa Ile Gln Gln Leu Phe Xaa Lys Val Ala Gln Gln Gln Arg Xaa Leu
            20                  25                  30

Xaa Lys Gln Xaa Leu Arg Ile Gln Xaa Leu Gln Ser Gln Xaa Xaa Leu
        35                  40                  45

Leu Xaa Xaa Xaa His Leu Asp Xaa Xaa Val Xaa Lys Xaa Xaa Xaa Xaa
    50                  55                  60

Xaa Xaa Leu Pro Xaa Met Xaa Gln Xaa Xaa Xaa Xaa Xaa Xaa Asn Xaa
65                  70                  75                  80

Xaa Xaa Leu His Xaa
            85

<210> SEQ ID NO 25
<211> LENGTH: 185
<212> TYPE: PRT
<213> ORGANISM: Homo sapiens
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
```

```
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (85)..(87)
<223> OTHER INFORMATION: Xaa can be any naturally occurring amino acid
<220> FEATURE:
<221> NAME/KEY: misc_feature
<222> LOCATION: (89)..(90)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (115)..(118)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
```

<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid

<400> SEQUENCE: 25

```
Gly Gly Trp Thr Val Ile Gln Arg Xaa Xaa Xaa Xaa Ser Val Asp Xaa
1               5                   10                  15

Asn Xaa Xaa Trp Glu Ala Tyr Lys Xaa Gly Phe Gly Asp Xaa Xaa Gly
            20                  25                  30

Glu Phe Trp Leu Gly Leu Glu Lys Xaa His Ser Ile Xaa Gly Xaa Arg
        35                  40                  45

Xaa Ser Xaa Leu Ala Val Gln Leu Xaa Asp Trp Asp Gly Asn Ala Xaa
    50                  55                  60

Leu Leu Gln Phe Xaa Xaa His Xaa Gly Gly Xaa Asp Thr Ala Tyr Ser
65                  70                  75                  80

Leu Gln Leu Thr Xaa Xaa Xaa Ala Xaa Xaa Leu Gly Ala Thr Xaa Val
                85                  90                  95

Xaa Pro Xaa Gly Leu Ser Xaa Pro Phe Ser Thr Trp Asp Gln Asp His
            100                 105                 110

Asp Leu Xaa Xaa Xaa Xaa Asn Cys Ala Lys Ser Leu Ser Gly Gly Xaa
        115                 120                 125

Trp Phe Gly Thr Cys Ser His Ser Asn Leu Asn Xaa Gln Tyr Phe Xaa
    130                 135                 140

Ser Ile Pro Xaa Gln Xaa Gln Xaa Xaa Lys Lys Gly Ile Phe Trp Lys
145                 150                 155                 160

Thr Trp Xaa Gly Arg Tyr Tyr Pro Leu Gln Ala Thr Thr Xaa Leu Ile
                165                 170                 175

Gln Pro Met Xaa Ala Xaa Ala Ala Ser
            180                 185
```

<210> SEQ ID NO 26
<211> LENGTH: 183
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (39)..(55)

```
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (161)..(164)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid

<400> SEQUENCE: 26

Met Ser Gly Ala Xaa Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Xaa Xaa Xaa Xaa Xaa Xaa Xaa Xaa Xaa Xaa
        35                  40                  45

Xaa Xaa Xaa Xaa Xaa Xaa Xaa Arg Glu His Ala Glu Arg Thr Arg Ser
    50                  55                  60

Gln Leu Xaa Ala Leu Glu Arg Xaa Leu Ser Ala Xaa Xaa Ser Ala Xaa
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Xaa Xaa Xaa Xaa Leu Pro Xaa Met Ala Gln Pro Val Asp Xaa Ala His
                165                 170                 175

Asn Val Ser Arg Leu His Xaa
            180

<210> SEQ ID NO 27
<211> LENGTH: 185
<212> TYPE: PRT
<213> ORGANISM: Homo sapiens
<220> FEATURE:
<221> NAME/KEY: misc_feature
```

```
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid

<400> SEQUENCE: 27

Gly Gly Trp Thr Val Ile Gln Arg Xaa His Asp Xaa Ser Val Asp Xaa
1               5                   10                  15

Asn Arg Pro Trp Glu Ala Tyr Lys Ala Gly Phe Gly Asp Xaa His Gly
            20                  25                  30

Glu Phe Trp Leu Gly Leu Glu Lys Val His Ser Ile Xaa Gly Asp Arg
        35                  40                  45

Asn Ser Arg Leu Ala Val Gln Leu Xaa Asp Trp Asp Gly Asn Ala Glu
    50                  55                  60

Leu Leu Gln Phe Ser Xaa His Xaa Gly Gly Xaa Asp Thr Ala Tyr Ser
65                  70                  75                  80
```

```
Leu Gln Leu Thr Ala Xaa Xaa Ala Gly Gln Leu Gly Ala Thr Thr Val
                 85                  90                  95

Pro Pro Ser Gly Leu Ser Val Pro Phe Ser Thr Trp Asp Gln Asp His
            100                 105                 110

Asp Leu Xaa Arg Xaa Lys Asn Cys Ala Lys Ser Leu Ser Gly Gly Xaa
        115                 120                 125

Trp Phe Gly Thr Cys Ser His Ser Asn Leu Asn Xaa Gln Tyr Phe Arg
130                 135                 140

Ser Ile Pro Gln Gln Xaa Gln Lys Leu Lys Lys Gly Ile Phe Trp Lys
145                 150                 155                 160

Thr Trp Xaa Gly Arg Tyr Tyr Pro Leu Gln Ala Thr Thr Met Leu Ile
            165                 170                 175

Gln Pro Met Ala Ala Glu Ala Ala Ser
            180                 185

<210> SEQ ID NO 28
<211> LENGTH: 17
<212> TYPE: PRT
<213> ORGANISM: Homo sapiens

<400> SEQUENCE: 28

Asp Lys Met Asn Val Leu Ala His Gly Leu Leu Gln Leu Gly Gln Gly
1               5                   10                  15

Leu

<210> SEQ ID NO 29
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 29

Gly Ala Ala Gly
1

<210> SEQ ID NO 30
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 30

Gly Ala Gly Ala
1

<210> SEQ ID NO 31
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 31

Gly Gly Ala Ala
1

<210> SEQ ID NO 32
<211> LENGTH: 4
<212> TYPE: PRT
<213> ORGANISM: Artificial Sequence
```

```
<220> FEATURE:
<223> OTHER INFORMATION: Mutations at postitions 161-164

<400> SEQUENCE: 32

Ala Gly Gly Ala
1

<210> SEQ ID NO 33
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 33

Ala Gly Ala Gly
1

<210> SEQ ID NO 34
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 34

Ala Ala Gly Gly
1

<210> SEQ ID NO 35
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 35

Val Gly Ala Ala
1

<210> SEQ ID NO 36
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 36

Val Ala Ala Gly
1

<210> SEQ ID NO 37
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 37

Val Ala Gly Ala
1

<210> SEQ ID NO 38
<211> LENGTH: 4
<212> TYPE: PRT
<213> ORGANISM: Artificial Sequence
<220> FEATURE:
```

<223> OTHER INFORMATION: Mutations at postitions 161-164

<400> SEQUENCE: 38

Gly Ala Ala Val
1

<210> SEQ ID NO 39
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 39

Gly Ala Val Ala
1

<210> SEQ ID NO 40
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 40

Gly Val Ala Ala
1

<210> SEQ ID NO 41
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 41

Ala Gly Val Ala
1

<210> SEQ ID NO 42
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 42

Ala Gly Ala Val
1

<210> SEQ ID NO 43
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 43

Ala Ala Val Gly
1

<210> SEQ ID NO 44
<211> LENGTH: 4
<212> TYPE: PRT
<213> ORGANISM: Artificial Sequence
<220> FEATURE:
<223> OTHER INFORMATION: Mutations at postitions 161-164

```
<400> SEQUENCE: 44

Ala Ala Gly Val
1

<210> SEQ ID NO 45
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 45

Ala Val Ala Gly
1

<210> SEQ ID NO 46
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 46

Ala Val Gly Ala
1

<210> SEQ ID NO 47
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 47

Gly Ala Val Val
1

<210> SEQ ID NO 48
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 48

Gly Val Ala Val
1

<210> SEQ ID NO 49
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 49

Gly Val Val Ala
1

<210> SEQ ID NO 50
<211> LENGTH: 4
<212> TYPE: PRT
<213> ORGANISM: Artificial Sequence
<220> FEATURE:
<223> OTHER INFORMATION: Mutations at postitions 161-164
```

```
<400> SEQUENCE: 50

Ala Gly Val Val
1

<210> SEQ ID NO 51
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 51

Ala Val Val Gly
1

<210> SEQ ID NO 52
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 52

Ala Val Gly Val
1

<210> SEQ ID NO 53
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 53

Val Gly Ala Val
1

<210> SEQ ID NO 54
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 54

Val Gly Val Ala
1

<210> SEQ ID NO 55
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 55

Val Ala Gly Val
1

<210> SEQ ID NO 56
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 56
```

Gly Val Val Val
1

<210> SEQ ID NO 57
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 57

Val Gly Val Val
1

<210> SEQ ID NO 58
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 58

Val Val Val Gly
1

<210> SEQ ID NO 59
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 59

Val Val Gly Val
1

<210> SEQ ID NO 60
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 60

Val Ala Val Gly
1

<210> SEQ ID NO 61
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 61

Val Val Gly Ala
1

<210> SEQ ID NO 62
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 62

Val Val Ala Gly
1

<210> SEQ ID NO 63
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 63

Val Val Val Ala
1

<210> SEQ ID NO 64
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 64

Val Val Ala Val
1

<210> SEQ ID NO 65
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 65

Gly Ala Ala Ala
1

<210> SEQ ID NO 66
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 66

Ala Gly Ala Ala
1

<210> SEQ ID NO 67
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 67

Ala Ala Ala Gly
1

<210> SEQ ID NO 68
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 68

Ala Ala Gly Ala

```
<210> SEQ ID NO 69
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 69

Ala Ala Val Val
1

<210> SEQ ID NO 70
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 70

Ala Ala Val Ala
1

<210> SEQ ID NO 71
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 71

Ala Ala Ala Val
1

<210> SEQ ID NO 72
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 72

Ala Val Ala Ala
1

<210> SEQ ID NO 73
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 73

Val Ala Ala Ala
1

<210> SEQ ID NO 74
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 74

Ala Val Val Val
1
```

```
<210> SEQ ID NO 75
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 75

Val Ala Val Val
1

<210> SEQ ID NO 76
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 76

Val Val Val Val
1

<210> SEQ ID NO 77
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 77

Ser Ser Ser Ser
1

<210> SEQ ID NO 78
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 78

Gly Gly Gly Gly
1

<210> SEQ ID NO 79
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 79

Ala Ala Ala Ala
1

<210> SEQ ID NO 80
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 80

Gly Ser Gly Ser
1
```

<210> SEQ ID NO 81
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 81

Gly Ser Ser Gly
1

<210> SEQ ID NO 82
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 82

Gly Gly Ser Ser
1

<210> SEQ ID NO 83
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 83

Ser Gly Ser Gly
1

<210> SEQ ID NO 84
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 84

Ser Gly Gly Ser
1

<210> SEQ ID NO 85
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 85

Ser Ser Gly Gly
1

<210> SEQ ID NO 86
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 86

Gly Ser Gly Gly
1

```
<210> SEQ ID NO 87
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 87

Ser Gly Gly Gly
1

<210> SEQ ID NO 88
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 88

Gly Gly Ser Gly
1

<210> SEQ ID NO 89
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 89

Gly Gly Gly Ser
1

<210> SEQ ID NO 90
<211> LENGTH: 4
<212> TYPE: PRT
<213> ORGANISM: Artificial Sequence
<220> FEATURE:
<223> OTHER INFORMATION: Mutations at postitions 161-164

<400> SEQUENCE: 90

Val Ala Val Ala
1

<210> SEQ ID NO 91
<211> LENGTH: 23
<212> TYPE: DNA
<213> ORGANISM: Artificial Sequence
<220> FEATURE:
<223> OTHER INFORMATION: PCR Primer

<400> SEQUENCE: 91
agggataggc ttaccttcga atg                                          23

<210> SEQ ID NO 92
<211> LENGTH: 12
<212> TYPE: DNA
<213> ORGANISM: Artificial Sequence
<220> FEATURE:
<223> OTHER INFORMATION: Probe

<400> SEQUENCE: 92
cagcagcctc cc                                                      12

<210> SEQ ID NO 93
<211> LENGTH: 16
<212> TYPE: DNA
```

```
<213> ORGANISM: Artificial Sequence
<220> FEATURE:
<223> OTHER INFORMATION: mutant Angptl4 8501 cDNA

<400> SEQUENCE: 93
ccggatcagg atcact                                                    16

<210> SEQ ID NO 94
<211> LENGTH: 16
<212> TYPE: DNA
<213> ORGANISM: Artificial Sequence
<220> FEATURE:
<223> OTHER INFORMATION: mutant Angptl4 8515 cDNA

<400> SEQUENCE: 94
cctccggcgg cggcct                                                    16

<210> SEQ ID NO 95
<211> LENGTH: 4
<212> TYPE: PRT
<213> ORGANISM: homo sapiens

<400> SEQUENCE: 95

Arg Arg Lys Arg
1

<210> SEQ ID NO 96
<211> LENGTH: 17
<212> TYPE: PRT
<213> ORGANISM: HOMO SAPIENS

<400> SEQUENCE: 96

Asp Glu Met Asn Val Leu Ala His Gly Leu Leu Gln Leu Gly Gln Gly
1               5                   10                  15

Leu
```

METHODS FOR TREATMENT OF NEPHROTIC SYNDROME AND RELATED CONDITIONS

CROSS-REFERENCE TO RELATED APPLICATIONS

This application is a divisional of U.S. application Ser. No. 13/841,240, filed Mar. 15, 2013 (pending). U.S. application Ser. No. 13/841,240 is a continuation-in-part of U.S. application Ser. No. 13/364,962, filed on Feb. 2, 2012 (pending). U.S. application Ser. No. 13/364,962 is a continuation of International Application PCT/US11/39255, filed on Jun. 6, 2011 (abandoned). International Application PCT/US11/39255 cites for priority U.S. Application 61/351,866, filed Jun. 5, 2010. U.S. application Ser. No. 13/364,962 cites for priority U.S. Application 61/438,854, filed on Feb. 2, 2011. U.S. application Ser. No. 13/841,240 is incorporated herein by reference in its entirety.

STATEMENT AS TO FEDERALLY SPONSORED RESEARCH

This invention was made with government support under grant numbers R01DK077073 and R01DK090035, awarded by the National Institutes of Health. The government has certain rights in the invention.

FIELD OF THE DISCLOSURE

The present disclosure is directed to methods for the treatment and prevention of nephrotic syndrome and conditions related thereto, such as, but not limited to, proteinuria and edema.

BACKGROUND

Nephrotic syndrome (NS) is a general term that refers to the loss of protein in the urine (proteinuria), hyperlipidemia (hypercholesterolemia and hypertriglyceridemia), and edema. Nephrotic syndrome involves changes in the pathology of cells in the kidney, such as podocytes. Proteinuria is defined as the presence of an excess of serum proteins in the urine. Albuminuria, a specific type of proteinuria, is a pathological condition wherein albumin is present in the urine.

Podocytes (or visceral epithelial cells) are cells in the outer layer of the glomerular capillary loop in the kidneys. The glomerulus filters blood, holding back large molecules such as proteins, and passing through small molecules such as water, salts, and sugar, as the first step in forming urine. The long projections, or "foot processes," of the podocytes wrap around the capillaries, and come to rest on the glomerular basement membrane. The foot processes are connected by a porous structure called the slit diaphragm. The innermost layer of the glomerular capillary loop is made of fenestrated endothelial cells. leakage of blood proteins, resulting in proteinuria.

When protein is lost in the urine, its plasma concentration decreases, allowing water to move into other areas of the body, which leads to swelling known as edema. Edema is commonly observed in the feet and legs, in the belly or abdomen (ascites), and around the eyes, but can occur anywhere, especially in response to gravity. Additionally, because of this extra fluid that stays in the body, people often gain weight, experience fatigue and may find that they urinate less often Many conditions are categorized as nephrotic syndromes, including minimal change disease (MCD), focal segmental glomerulosclerosis (FSGS), membranous nephropathy (MN) (also called membranous glomerulonephritis, MGN), and membranoproliferative glomerulonephritis (MPGN). For years pathologists found no changes in MCD tissue when viewing specimens under light microscopy, hence the name minimal change disease. With the advent of electron microscopy, the changes now known as the hallmarks for the disease include diffuse loss of podocyte foot processes, vacuolation of the podocyte foot processes, and growth of microvilli on the visceral epithelial cells. Diabetic nephropathy is the most common cause of nephrotic syndrome.

Hypertriglyceridemia may occur due to changes in the activity of enzymes that degrade triglycerides, such as lipoprotein lipase (LPL) (2-4). Certain proteins involved in the etiology of nephrotic syndrome and proteinuria, such angiopoietin-like 4 (Angptl4), inhibit the activity of LPL.

The molecular basis of nephrotic syndrome is not known. Increased levels of Angptl4 have been noted in nephrotic syndrome, such as MCD, MN/MGN, and MPGN, but increased circulating levels of Angptl4 have not been associated with causation of proteinuria in nephrotic syndrome. However, the role of Angptl4 in nephrotic syndrome, such as but not limited to, MCD, FSGS, MN/MGN, and MPGN, and related conditions, such as, but not limited to, proteinuria have not been previously reported. Furthermore, the association of proteinuria and glucocorticoid sensitivity in nephrotic syndrome and the link between proteinuria and hypertriglyceridemia, two key components of nephrotic syndrome, have yet to be established. Therapy designed to reduce proteinuria further complicates the study of disease mechanisms. For example, glucocorticoids used to treat proteinuria in MCD independently raise plasma triglyceride levels (5), and normalization of plasma triglyceride levels lags behind the response of proteinuria to glucocorticoids in certain forms of nephrotic syndrome, such as MCD (6).

The present disclosure show that increased circulating levels of Angptl4 reduce the severity of nephrotic syndrome and conditions associated therewith, such as but not limited to, proteinuria. As a result, the present disclosure provides method for treating and/or preventing nephrotic syndrome, such as but not limited to, MCD, FSGS, MN/MGN, MPGN and diabetic nephropathy as well as methods of alleviating symptoms associated with nephrotic syndrome, including, but not limited to, proteinuria and edema. The present disclosure further provides methods for reducing proteinuria and edema.

BRIEF DESCRIPTION OF THE FIGURES

FIGS. 1A-1H show the development and characterization of aP2-Angptl4 TG rats.

FIG. 1A shows a 2D gel analysis of 200 µg human plasma (n=4 patients/group, cropped representative blots shown) and demonstrates the presence of increased circulating levels of Angptl4 in patients with minimal change disease (MCD) in relapse and in patients with membranous nephropathy (MN) (indicated by arrows), compared to patients with MCD in remission (i. e. non proteinuric patients).

FIG. 1B shows a transgenic (TG) rat model for adipose tissue specific over expression of Angptl4 (aP2-Angplt4 TG).

FIG. 1C shows tissue specific over expression of Angptl4 mRNA (n=3 rats/group) in aP2-Angptl4 TG rats. WAT is white adipose tissue, BAT is brown adipose tissue. *** $P<0.001$.

FIG. 1D shows 2D gel electrophoresis of 200 µg plasma, followed by Western blot for Angptl4 and demonstrates that heterozygous aP2-Angptl4 TG rats had higher circulating Angptl4 levels than wild type rats (age 3 months, n=3 blots/group).

FIG. 1E shows 2D gel electrophoresis of 200 µg plasma, followed by Western blot with the anti-V5 and anti-Angptl4 antibodies and demonstrates the presence of adipose tissue secreted V5-tagged Angptl4 in the plasma of aP2-Angptl4 TG rats.

FIG. 1F shows 2D gel electrophoresis of anti-N-terminal Angptl4 immunoprecipitates from aP2-Angptl4 TG rat plasma followed by Western blotting using lectin SNA I and anti-Angptl4 antibodies and confirmed the presence of circulating sialylated Angptl4 in the aP2-Angptl4.

FIG. 1G shows PAS stained sections from 3 month old heterozygous aP2-Angptl4 TG rats (n=3 rats/group) and demonstrates normal glomerular morphology (magnification 400×).

FIG. 1H shows immunogold EM with anti-V5 antibody to specifically detect transgenic protein in 3 month heterozygous aP2-Angplt4 TG male rats and demonstrated gold particles selectively on the endothelial surface in aP2-Angptl4 TG rats (indicated by arrows).

FIGS. 2A-2H show the relationship of increased circulating levels of Angptl4 with proteinuria/albuminuria.

FIG. 2A shows assessment of urinary protein excretion (3 µg/lane, except MCD remission) in different human and experimental disease conditions by GelCode blue stained SDS PAGE and demonstrated the absence of significant proteinuria in aP2-Angptl4 TG rats (lane marked with *, arrow shows intact albumin at around 70 kDa).

FIG. 2B shows assessment of albuminuria by ELISA and revealed that heterozygous female aP2-Angptl4 TG rats had lower albuminuria than wild type littermates (n=6 rats/group).

FIG. 2C shows assessment of albuminuria by ELISA and revealed that heterozygous male aP2-Angptl4 TG rats had lower albuminuria than wild type littermates (n=6 rats/group).

FIG. 2D shows induction of puromycin nephrosis (PAN), a model of nephrotic syndrome, in wild type and aP2-Angptl4 TG rats and demonstrates less proteinuria in aP2-Angptl4 TG rats compared to wild type littermates (n=8 rats/group). * $P<0.05$,  $P<0.01$ compared to corresponding controls FIG. 2E shows recombinant Angptl4 had protective effects on cultured glomerular endothelial cells (GEnCs).  $P<0.01$, * $P<0.001$ compared to corresponding controls FIG. 2F shows upregulation of Angptl4 in wild type rats in disease models like PAN on Day 6 was exclusively glomerular, while upregulation of Angptl4 in adipose tissue was noted on Day 10 when proteinuria and glomerular Angptl4 expression are on the decline (n=3 rats/sample).  $P<0.01$, *** $P<0.001$ compared to corresponding controls FIG. 2G shows increased circulating levels of Angptl4 at baseline and after induction of PAN in aP2-Angptl4 TG rats results in increased plasma triglyceride levels compared to wild type rats. * $P<0.05$ compared to corresponding controls FIG. 2H shows increased circulating levels of Angptl4 at baseline and after induction of PAN in aP2-Angptl4 TG rats results in reduced post-heparin lipoprotein lipase (LPL) activity compared to wild type rats. * $P<0.05$ compared to corresponding controls FIG. 3 shows the primers and probes used for Taqman real time PCR (SEQ ID NOS. 11-22).

FIGS. 4A-4B show recombinant Angptl4 reduces proteinuria in animal models of human glomerular disease.

FIG. 4A shows reduction of proteinuria in Thy1.1 nephritis, a short term model of mesangial injury. Thy1.1 nephritis was induced in male Wistar rats (n=4 rats/group). After assessment of baseline proteinuria (Day 1), concentrated supernatant protein from Angptl4 stable or control cell lines were injected intra-peritoneally on two consecutive days (Days 1 & 2, arrows) into Buffalo Mna rats (n=4 rats/group) followed by assessment of proteinuria. Proteinuria was lower in Angptl4 treated rats throughout, and was statistically significant on Day 5. * $P<0.05$; ** $P<0.01$. all values are mean±SE.

FIG. 4B shows reduction of proteinuria in Thy1.1 nephritis, a short term model of mesangial injury. Thy1.1 nephritis was induced in male Wistar rats (n=4 rats/group, injected on Day 0). After confirming the induction of proteinuria (Day 1), concentrated supernatant protein from Angptl4 stable or control cell lines were injected intravenously on two consecutive days (Days 1 & 2, arrows) followed by assessment of proteinuria. Proteinuria was lower in Angptl4 treated rats throughout, and was statistically significant on Day 5. * $P<0.05$; ** $P<0.01$. all values are mean±SE FIG. 5 shows the amino acid and cDNA sequences of Angptl4 from various species. SEQ ID NOS. 1 and 2 show amino acid and cDNA sequence from human (Protein Variant 1 isoform a, long form; underlined amino acid sequences at a position 40 and 161-164); SEQ ID NOS. 3 and 4 show amino acid and cDNA sequence from human (Protein Variant 3 isoform b, short form; underlined amino acid sequences at a position 40 and 161-164); SEQ ID NOS. 5 and 6 show amino acid and cDNA sequence from rat; SEQ ID NOS: 7 and 8 show amino acid and cDNA from mouse; underlined are forward sequencing primers. Bold are reverse sequencing primers. SEQ ID NO. 9 shows human Protein Variant Derivative with the sequence of interest in generic form. SEQ ID NO.10 shows human Protein Variant 3 Derivative with the sequence of interest in generic form.

FIGS. 6A-6N show that elevated circulating Angptl4 levels are required for the development of hypertriglyceridemia in nephrotic syndrome.

FIG. 6A shows ELISA for plasma Angptl4 levels in patients with nephrotic syndrome due to primary glomerular disease. Number of patients analyzed are shown in brackets FIG. 6B shows ELISA for plasma Angptl4 levels at pre-nephrotic and nephrotic stages in passive Heymann nephritis (PHN, a model of membranous nephropathy), Buffalo Mna (B. Mna, spontaneously develop focal and segmental glomerulosclerosis) and single dose intravenous puromycin aminonucleoside nephrosis (PAN, a model of minimal change disease), all rat models of nephrotic syndrome.

FIGS. 6C-6E show Proteinuria, hypertriglyceridemia and LPL activity in PHN,

FIGS. 6F-6H show Buffalo Mna rats,

FIG. 6N shows plasma triglyceride levels in Angptl4−/− and +1+ mice 48 hours after induction of nephrotic syndrome using γ2-NTS. * $P<0.05$,  $P<0.01$, * $P<0.001$ FIGS. 7A-7H show the source of circulating Angptl4 in nephrotic syndrome.

FIG. 7A shows multi-organ Angptl4 mRNA expression relative to control in passive Heymann nephritis (PHN), FIG. 7B shows multi-organ Angptl4 mRNA expression relative to control in Buffalo Mna rats and FIG. 7C shows multi-organ Angptl4 mRNA expression relative to control in puromycin aminonucleoside nephrosis (PAN).

FIG. 7D shows a representative 2-dimensional gel electrophoresis and Western blot of plasma showing circulating Angptl4 levels in proteinuric NPHS2-Angptl4 transgenic rats before and after the induction of mild PAN.

FIG. 7E shows a densitometry analysis of 2-dimensional gels in d

FIG. 7F shows a 2-dimensional gel electrophoresis and Western blot of plasma from NPHS2-Angptl4 transgenic rats with PAN to demonstrate the presence of V5-tagged transgene expressed Angptl4 in the circulation.

FIGS. 7G and 7H show plasma triglyceride levels (FIG. 7G) and lipoprotein lipase (LPL) activity (FIG. 7H) six days after induction of PAN in wild type Sprague Dawley, aP2-Angptl4 and NPHS2-Angptl4 transgenic rats. Empty bars correspond to data from FIG. 6L and FIG. 6M included here for comparison. * $P<0.05$,  $P<0.01$, * $P<0.001$. In panels G and H, statistical significance is shown for difference between transgenic rats and corresponding wild type controls. $P<0.001$ for each rat type before and after induction of PAN. In panels A to C, 3-fold change in expression (horizontal line) was taken as significant.

FIG. 8A shows a representative reducing Western blots of urine from normal Sprague Dawley (SD), PAN, PHN, and Buffalo Mna rats. Black arrows point towards Angptl4 bands. Albumin blush is also noted in PAN, PHN and Buffalo Mna rats between 65 and 70 kDa.

FIG. 8B shows non-reducing Western blot of urine from nephrotic rats using goat anti LPL antibody to assess for urinary loss of LPL (arrow).

FIG. 8C shows non-reducing western blot of nephrotic rat urine using anti-LPL monoclonal antibody 5D2 to identify active LPL (arrow).

FIG. 8D shows a multi-organ mRNA expression profile for LPL in Sprague Dawley rats with PAN.

FIG. 8E shows an mRNA expression profile of major organs that express LPL in aP2-Angptl4 transgenic rats. In panels D and E, 3-fold change in expression (horizontal line) was taken as significant.

FIG. 9A shows proteinuria after induction of puromycin aminonucleoside nephrosis (PAN) in wild type Sprague Dawley and aP2-Angptl4 transgenic rats FIG. 9B shows the effect of depleting circulating Angptl4 using an anti-Angptl4 Ab. on proteinuria in Sprague Dawley rats with PAN.

FIG. 9C shows proteinuria in Buffalo Mna rats after injection of concentrated supernatant from recombinant rat Angptl4 secreting stable cell lines or control stable cell lines.

FIG. 9D shows the effect of injecting recombinant rat Angptl4 or control protein from the above cell lines on proteinuria in severe anti-Thy1.1 nephritis, a model of mesangial injury. * $P<0.05$, ** $P<0.01$ FIGS. 10A-10E show dissociation of effects of Angptl4 on triglycerides and proteinuria using mutant recombinant human Angptl4.

FIG. 10A shows a schematic representation of wild type and mutant human Angptl4 proteins showing mutations in areas important for LPL binding (amino acid 40, and adjacent amino acid 39) and protein cleavage (amino acids 161 to 164).

FIG. 10B shows a western blot of recombinant tagged proteins using mouse anti V5 antibody and control mouse IgG to demonstrate the expected size of the intact protein and reduced cleavage in the mutant proteins (arrows).

FIG. 10C shows plasma levels of wild type or mutant human Angptl4 after injecting 55 µg of recombinant human protein in Buffalo Mna rats, a model of focal and segmental glomerulosclerosis (FSGS) as assessed by OD 450 using reagents from the human Angptl4 ELISA kit.

FIG. 10D shows the effect of wild type and mutant Angptl4 on proteinuria in Buffalo Mna rats. * $P<0.05$, shown where all 3 study groups were individually different from control.

FIG. 10E shows the effect of wild type and mutant Angptl4 on plasma triglyceride levels in Buffalo Mna rats. * $P<0.05$ for wild type values compared to baseline. # $P<0.05$ for 6 hour mutant values compared to wild type.

FIGS. 11A-11H show that circulating Angptl4 reduces proteinuria via its interaction with glomerular endothelial αvβ5 integrin. Red arrows indicate time points when anti β5 integrin antibody or pre-immune serum were injected.

FIG. 11A shows a confocal image of a glomerulus from an aP2-Angptl4 transgenic rat demonstrates co-localization of Angptl4-V5 (anti-V5 antibody, red) secreted from adipose tissue with glomerular endothelium (anti Von Willebrand factor antibody, green)

FIG. 11B shows an immunogold electron micrograph of a glomerulus from aP2-Angptl4 transgenic rats using anti-V5 antibody to show glomerular endothelial cell surface binding of adipose tissue secreted Angptl4-V5.

FIG. 11C shows silaylated Angptl4 protein protected cultured rat glomerular endothelial cells (GEnCs) from oxidative injury, whereas hyposialylated Angptl4 increases the effects of oxidative injury.

FIG. 11D shows the interaction of purified αvβ5 integrin with sialylated Angptl4 or control in vitro. Linear regression slope (black) is superimposed.

FIG. 11E shows the development of proteinuria after induction of nephrotic syndrome using γ2-nephrotoxic serum (NTS) in β5 integrin −/− and +/+ mice to demonstrate the protective effects of the endothelial β5 integrin-circulating Angptl4 interaction on proteinuria during the peripheral phase of Angptl4 secretion.

FIG. 11F shows the effect of blocking the endothelial β5 integrin-Angptl4 interaction using anti β5 integrin antibodies on recovery from peak proteinuria (corresponds with the peripheral phase of Angptl4 secretion) in Sprague Dawley rats with PAN.

FIG. 11G shows the effect of blocking the endothelial β5 integrin-Angptl4 interaction using anti β5 integrin antibodies on recovery from peak proteinuria in aP2-Angptl4 transgenic rats with PAN.

FIG. 11H shows the induction of nephrotic syndrome using γ2-NTS in Angptl4−/− and +/+ mice to determine whether the lack of Angptl4 affects recovery from peak proteinuria during the peripheral phase of Angptl4 expression. The findings of the glomerular phase are consistent with our previously published study (ref. 6 from working example 4). * $P<0.05$,  $P<0.01$, *$P<0.001$

FIG. 12A shows a cropped image of representative Western blots with anti-Angptl4 antibody to show elevated circulating Angptl4 levels in membranous nephropathy (MN), focal and segmental glomerulosclerosis (FSGS) and minimal change disease (MCD). Angptl4 spots are enclosed in green circles/ovals.

FIG. 12B shows ponceau red stained images of nitrocellulose membranes corresponding to Western blots.

FIG. 17 shows amino acid and nucleic acid substitutions for four mutant forms of human Angptl4.

SUMMARY OF THE DISCLOSURE

Figure 6I:
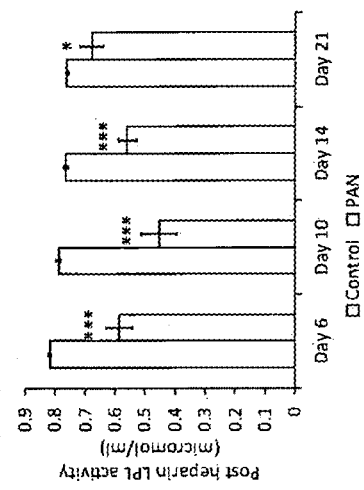
FIGS. 6I-6K show PAN rats.

In a first aspect, the present disclosure provides methods of treatment and/or prevention of nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a further embodiment, the nephrotic syndrome is characterized as MSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4 or an Angptl4 polypeptide derivative. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats nephrotic syndrome by providing Angptl4 function. In an alternate embodiment, such administration treats nephrotic syndrome by providing a modified Angptl4 function, such as, but not limited to, an Angptl4 function that display reduced LPL inhibition or is resistant to cleavage.

In a second aspect, the present disclosure provides methods of treatment and/or prevention of MCD. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats MCD by providing Angptl4 function. In an alternate embodiment, such administration treats MCD by providing a modified Angptl4 function, such as, but not limited to, an Angptl4 function that display reduced LPL inhibition or is resistant to cleavage.

In a third aspect, the present disclosure provides methods of alleviating one or more symptoms of nephrotic syndrome, such as, but not limited to, proteinuria, hypercholesterolemia, hypertriglyceridemia and edema. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration alleviates one or more symptoms of nephrotic syndrome by providing Angptl4 function. In an alternate embodiment, such administration alleviates one or more symptoms of nephrotic syndrome by providing a modified Angptl4 function, such as, but not limited to, an Angptl4 function that display reduced LPL inhibition or is resistant to cleavage.

In a fourth aspect, the present disclosure provides methods for reducing proteinuria in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In another embodiment, the subject is suffering from a disorder characterized by proteinuria. In another embodiment, the subject is suffering from a diabetic condition. In a further embodiment, the proteinuria is caused by FSGS. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces proteinuria by providing Angptl4 function. In an alternate embodiment, such administration reduces proteinuria by providing a modified Angptl4 function, such as, but not limited to, an Angptl4 function that display reduced LPL inhibition or is resistant to cleavage.

In a fifth aspect, the present disclosure provides methods of reducing edema in a subject. In one embodiment, the subject is suffering from nephrotic syndrome. In one embodiment, the nephrotic syndrome is characterized as MCD, FSGS, MN/MGN, MPGN, and diabetic nephropathy. In another embodiment, the nephrotic syndrome is characterized as MCD. In a further embodiment, the nephrotic syndrome is caused by FSGS. In a specific embodiment, the edema is caused by decreased circulating levels of plasma proteins such as albumin. In a further embodiment, the nephrotic syndrome is caused by a diabetic condition In one embodiment, the diabetic condition is diabetic nephropathy, diabetes mellitus, lupus nephritis or primary glomerular disease. Reduction of proteinuria through the administration of an Angptl4 polypeptide of Angptl4 polypeptide derivative will reduce proteinuria, raise plasma protein levels and thereby reduce edema. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces edema by providing Angptl4 function. In an alternate embodiment, such administration reduces edema by providing a modified Angptl4 function, such as, but not limited to, an Angptl4 function that display reduced LPL inhibition or is resistant to cleavage.

In a sixth aspect, the present disclosure provides methods of reducing hypercholesterolemia and/or hypertriglyceridemia in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by a diabetic condition In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces hypercholesterolemia and/or hypertriglyceridemia by providing Angptl4 function. In an alternate embodiment, such administration reduces hypercholesterolemia and/or hypertriglyceridemia by providing a modified Angptl4 function, such as, but not limited to, an Angptl4 function that display reduced LPL inhibition or is resistant to cleavage.

In a seventh aspect, the present disclosure provides methods of treatment and/or prevention of a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats the foregoing conditions by providing Angptl4 function. In an alternate embodiment, such administration treats the foregoing conditions by providing a modified Angptl4 function, such as, but not limited to, an Angptl4 function that display reduced LPL inhibition or is resistant to cleavage.

In an eighth aspect, the present disclosure provides a pharmaceutical composition for use in the methods of the first through sixth aspects. The composition comprises one or more Anptl4 polypeptides or polypeptide derivatives. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein.

DETAILED DESCRIPTION

In the following discussion certain articles and methods will be described for background and introductory purposes.

Nothing contained herein is to be construed as an "admission" of prior art. Applicant expressly reserves the right to demonstrate, where appropriate, that the articles and methods referenced herein do not constitute prior art under the applicable statutory provisions.

While investigating nephrotic syndrome, it was noted that Angptl4 secreted from podocytes induced proteinuria. More importantly, as described herein, circulating Angptl4 reduced the proteinuria in a transgenic animal model. Increased levels of Angptl4 have been noted in nephrotic syndrome, such as MCD and MN, but increased circulating levels of Angptl4 have not been associated with causation of nephrotic syndrome.

While increased Angptl4 levels are shown to treat nephrotic syndrome and reduce associated proteinuria, increased Angptl4 in the circulation has been observed to induce hyperlipidemia (hypertriglyceridemia), such as, but not limited to, through inhibition of LPL. It would be advantageous to provide the benefits of increased circulating Angptl4 levels without the negative consequences of hyperlipidemia. Such an approach is possible using the Angptl4 polypeptide derivatives as disclosed herein.

Angiopoietin-like proteins have been implicated in the development of hypertriglyceridemia and tumor metastasis, and are functionally distinct from the angiopoietins. Angptl4 is a PPAR□ (8) and PPAR□ (9) target gene highly expressed in the liver and adipose tissue, strongly induced by fasting in white adipose tissue and liver, and is an apoptosis survival factor for vascular endothelial cells under normoxic conditions (10). Angptl4 is a potent inhibitor of LPL (11), inducing significant hypertriglyceridemia following intravenous injection or adenovirus-mediated expression (12, 13). Other studies showed lesser expression of Angptl4 in cardiomyocytes and skeletal muscle, and low level expression in whole kidney on Northern blot analysis (8). Recent population based studies of the ANGPTL4 gene reveals variants that affect triglyceride levels in humans (14, 15).

The present disclosure shows a conclusive role for circulating Angptl4 in the reduction of proteinuria observed in nephrotic syndrome, such as, but not limited to, MCD, FSGS, MN, MPGN and diabetic nephropathy.

DEFINITIONS

The terms "prevention", "prevent", "preventing", "suppression", "suppress" and "suppressing" as used herein refer to a course of action (such as administering a compound or pharmaceutical composition) initiated prior to the onset of a symptom, aspect, or characteristics of a disease or condition so as to prevent or reduce such symptom, aspect, or characteristics. Such preventing and suppressing need not be absolute to be useful.

The terms "treatment", "treat" and "treating" as used herein refers a course of action (such as administering a compound or pharmaceutical composition) initiated after the onset of a symptom, aspect, or characteristics of a disease or condition so as to eliminate or reduce such symptom, aspect, or characteristics. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease or condition. Such effect need not be absolute to be beneficial. When referring to an Angptl4 polypeptide or Angptl4 polypeptide derivative, the term "therapeutically effective amount" refers to an amount of such polypeptide sufficient to reduce proteinuria in a subject.

The term "pharmaceutically acceptable derivative" means any pharmaceutically acceptable salt, ester, salt of an ester, solvate or other derivative of an Angptl4 polypeptide or polypeptide derivative of the present disclosure that, upon administration to a subject, is capable of providing (directly or indirectly) the function of wild type Angptl4; in certain embodiment, the Angptl4 polypeptide or polypeptide derivative shows decreased LPL inhibitory activity of a resistance to cleavage. Particularly favored derivatives are those that increase the bioavailability of an Angptl4 polypeptide or polypeptide derivative of the disclosure when such polypeptides are administered to a subject (e.g., by allowing an orally administered compound to be more readily absorbed into the blood), enhance delivery of such polypeptides to a given biological compartment, increase solubility to allow administration by injection, alter metabolism or alter rate of excretion. In one embodiment, the derivative is a prodrug.

The term "pharmaceutically acceptable salt(s)", unless otherwise indicated, includes salts of acidic or basic groups that may be present in the Angptl4 polypeptide or polypeptide derivative of the present disclosure.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

Methods of Treatment and Prevention

The present disclosure provides methods of treatment and/or prevention of nephrotic syndrome. The present disclosure further provides methods of treatment and/or prevention of MCD, FSGS, and/or conditions with mesangial injury (such as diabetes mellitus). The present disclosure further provides methods of treatment and/or prevention of a diabetic condition. In one embodiment, the diabetic condition is diabetic nephropathy, diabetes mellitus, lupus nephritis or primary glomerular disease. The present disclosure additionally provides methods of alleviating one or more symptoms of nephritic syndrome, such as, but not limited to, proteinuria, hypercholesterolemia, hypertriglyceridemia and edema. Still further, the present disclosure provides for methods of reducing proteinuria. Further still, the present disclosure provides methods of reducing edema. The present disclosure additionally provides for pharmaceutical compositions comprising one or more Angptl4 polypeptides of Angptl4 polypeptide derivatives. The nature of the Angptl4 polypeptide derivatives is described in further detail below.

In one embodiment, the teachings of the present disclosure provide for the treatment and/or prevention of nephrotic syndrome in a subject in need of such treatment or prevention. In one embodiment, the nephrotic syndrome is characterized as MCD, FSGS, MN/MGN, and MPGN. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats nephrotic syndrome by providing Angptl4 function. In an alternate embodiment, such administration treats nephrotic syndrome by providing a modified Angptl4 function, such as, but not limited to, an Angptl4 function that display reduced LPL inhibition or is resistant to cleavage. Such method may further comprise identifying a subject in need of such treatment and/or prevention.

In an alternate embodiment, the teachings of the present disclosure provide for the treatment and/or prevention of MCD in a subject in need of such treatment or prevention. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats MCD by providing Angptl4 function. In an alternate embodiment, such administration treats MCD by providing a modified Angptl4 function, such as, but not limited to, an Angptl4 function that display reduced LPL inhibition or is resistant to cleavage. Such method may further comprise identifying a subject in need of such treatment and/or prevention.

In further embodiment, the teachings of the present disclosure provide for methods of alleviating one or more symptoms of nephrotic syndrome, such as, but not limited to, proteinuria, hypercholesterolemia, hypertriglyceridemia and edema. In one embodiment, the nephrotic syndrome is characterized as MCD, FSGS, MN/MGN, MPGN, and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration alleviates one or more symptoms of nephrotic syndrome by providing Angptl4 function. In an alternate embodiment, such administration alleviates one or more symptoms of nephrotic syndrome by providing a modified Angptl4 function, such as, but not limited to, an Angptl4 function that display reduced LPL inhibition or is resistant to cleavage. Such method may further comprise identifying a subject in need of such treatment and/or prevention.

In still a further embodiment, the teachings of the present disclosure provide methods for reducing proteinuria in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces proteinuria by providing Angptl4 function. In an alternate embodiment, such administration reduces proteinuria by providing a modified Angptl4 function, such as, but not limited to, an Angptl4 function that display reduced LPL inhibition or is resistant to cleavage. Such method may further comprise identifying a subject in need of such treatment and/or prevention.

In yet a further embodiment, the teachings of the present disclosure provide methods for reducing edema in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. In a specific embodiment, the edema is caused by decreased circulating levels of plasma proteins such as albumin. Reduction of proteinuria through the administration of an Angptl4 polypeptide or a Angptl4 polypeptide derivative will raise reduce proteinuria, raise plasma protein levels and thereby reduce edema. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces edema by providing Angptl4 function. In an alternate embodiment, such administration reduces edema by providing a modified Angptl4 function, such as, but not limited to, an Angptl4 function that display reduced LPL inhibition or is resistant to cleavage. Such method may further comprise identifying a subject in need of such treatment and/or prevention.

In still a further embodiment, the teachings of the present disclosure provide methods for reducing hypercholesterolemia and/or hypertriglyceridemia in a subject. In one embodiment, the subject is suffering from nephrotic syndrome. In one embodiment, the nephrotic syndrome is characterized as MCD, FSGS, MN/MGN, and MPGN. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces proteinuria by providing Angptl4 function. In an alternate embodiment, such administration reduces proteinuria by providing a modified Angptl4 function, such as, but not limited to, an Angptl4 function that display reduced LPL inhibition or is resistant to cleavage. Such method may further comprise identifying a subject in need of such treatment and/or prevention.

In still a further embodiment, the teachings of the present disclosure provide methods for treatment and/or prevention of a nephrotic syndrome that is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats the foregoing conditions by providing Angptl4 function. In an alternate embodiment, such administration treats the foregoing conditions by providing a modified Angptl4 function, such as, but not limited to, an Angptl4 function that display reduced LPL inhibition or is resistant to cleavage.

Some embodiments of administering the Angptl4 polypeptide or derivative involve a form of administration that delivers the polypeptide to the blood. In one example the polypeptide is administered intravenously. Given the appropriate dosage form, such administration may be performed orally, subcutaneously, or by other means as is known in the art. The Angptl4 polypeptide or derivative may be administered in a therapeutically effective amount; this amount will generally be within a certain range of ratios of mass of compound to mass of subject. In some embodiments of the method the polypeptide is administered at a dosage of about 0.005-150,000 µg/kg, 0.5-15,000 µg/kg, 5-1500 µg/kg, or 50-150 µg/kg. Thus, for a typical 70 kg human adult, the dosage may be 0.0035-11,000 mg, 0.035-1100 mg, 0.35-110 mg, or 15-11 mg. Administration may occur on a regular schedule. In some embodiments of the method the polypeptide is administered about once per 14 days. In other embodiments the polypeptide is administered about twice per month. In still other embodiments the polypeptide is administered from about once per month to about twice per month. In further embodiments, the polypeptide is administered once per a given time period selected from the group consisting of: a day, two days, three days, a week, ten days, two weeks, three weeks, four weeks, and a month.

Methods of Screening

The present disclosure also relates to a method for identifying a compound effective for treating or preventing nephrotic syndrome or a condition associated therewith, such as, but not limited to, proteinuria, hypercholesterolemia, hypertriglyceridemia or edema. In one embodiment, the nephrotic syndrome is characterized as MCD or MN. In another embodiment, the nephrotic syndrome is characterized as MCD. In another embodiment, the nephrotic syndrome is characterized by FSGS. In a further embodiment, the nephrotic syndrome is caused by a diabetic condition. In one embodiment, the diabetic condition is diabetic nephropathy, diabetes mellitus, lupus nephritis or primary glomerular disease. Such compounds may be useful as active ingredients included in pharmaceutical compositions or for administration alone. In one embodiment, the methods include determining the level a polypeptide involved in the etiology of nephrotic syndrome, such as, but not limited to, Angptl4.

In general, such screening methods comprises the steps of providing an assay system (as described in more detail below) that expresses a polypeptide involved in the etiology of nephrotic syndrome, such as, but not limited to, Angptl4, introducing into the assay system a test compound to be tested and determining whether the effect of the test compound on the level the polypeptide. The methods involve the identification of candidate or test compounds or agents (polypeptides, functional nucleic acids, carbohydrates, antibodies, small molecules or other molecules) which effect the level of sialylation of the polypeptide. Such compounds may then be further tested in appropriate systems (such as, but not limited to, the animal models systems described herein) to determine the activity of the identified compounds.

Candidate compounds are identified using a variety of assays, such as, but not limited to, assays that employ cells which express a polypeptide involved in the etiology of nephrotic syndrome, such as, but not limited to, Angptl4 or in assays with isolated polypeptides. The various assays can employ a variety of variants of such polypeptides (e. g., full-length, a biologically active fragment, or a fusion protein which includes all or a portion of the desired polypeptide). Moreover, such polypeptides can be derived from any suitable mammalian species (e. g., human, rat or murine); in a specific embodiment, the polypeptide is derived from a human.

Where the assay involves the use of a whole cell, the cell may either naturally express a polypeptide involved in the etiology of nephrotic syndrome, such as, but not limited to, Angptl4, or may be modified to express the same. In the latter case, cells can be modified to express a desired polypeptide through conventional molecular biology techniques, such as by infecting the cell with a virus comprising such polypeptide. The cell can also be a prokaryotic or an eukaryotic cell that has been transfected with a nucleotide sequence encoding such polypeptide. In the foregoing, full length polypeptides, fragments or fusion proteins containing at least a part of such polypeptide may be used. Exemplary assay systems are described in the current specification.

The various screening assays may be combined with an in vivo assay entailing measuring the effect of the test compound on the symptoms the disease states and conditions discussed herein. In such an embodiment, the compounds may be evaluated to determine if they impact a parameter associated with nephrotic syndrome or a condition related thereto, such as, but not limited to, proteinuria or edema. Such parameters include, but are not limited to, determining 1) the level of a polypeptide involved in the etiology of nephrotic syndrome and related conditions, such as, but not limited to Angptl4 and 2) determining the level of protein excretion, either total or with regard to specific components.

In one embodiment, such a screening assay can be performed, for example, by determining the level of a polypeptide, such as, but not limited to, Angptl4 and detecting a difference in the level of such polypeptide in the presence of as compared to the absence of a test compound. Such screening assay may be in vitro, in vivo or ex vivo and may be cell culture based (either with whole cells or lysates) or may be based on an animal model. Any assay of the present disclosure may be used in the foregoing method.

Suitable test compounds for use in the screening methods can be obtained from any suitable source, such as conventional compound libraries. The test compounds can also be obtained using any of the numerous approaches in combinatorial library methods known in the art, including: biological libraries, spatially addressable parallel solid phase or solution phase libraries, synthetic library methods requiring deconvolution, the "one-bead one-compound" library method and synthetic library methods using affinity chromatography selection. The biological library approach is limited to peptide libraries, while the other four approaches are applicable to peptide, non-peptide oligomer or small molecule libraries of compounds. Examples of methods for the synthesis of molecular libraries can be found in the art. Libraries of compounds may be presented in solution or on beads, bacteria, spores, plasmids or phage.

The present disclosure also provides kits for carrying out any method of the present disclosure, which can contain any of the compounds and/or compositions disclosed herein or otherwise useful for practicing a method of the disclosure.

Creation and Selection of Angptl4 Polypeptide Derivatives

Angiopoietin-related protein 4 is a polypeptide that in humans is encoded by the ANGPTL4 gene. This gene is a member of the angiopoietin/angiopoietin-like gene family and encodes a glycosylated, secreted protein with a N-terminal signal sequence (amino acid residues 1-22 of SEQ ID NO:1), a coiled-coil domain (amino acid residues 23-170 of SEQ ID NO:1), a linker region (amino acid residues 171-185 of SEQ ID NO:1) and a fibrinogen C-terminal domain (amino acid residues 186-406 of SEQ ID NO:1). This gene is induced under hypoxic conditions in endothelial cells and is the target of peroxisome proliferation activators. The encoded protein is a serum hormone directly involved in regulating glucose homeostasis, lipid metabolism, and insulin sensitivity and also acts as an apoptosis survival factor for vascular endothelial cells. Alternatively spliced transcript variants encoding different isoforms have been described. This gene was previously referred to as ANGPTL2 but has been renamed ANGPTL4.

Angptl4 inhibits LPL by breaking the LPL dimer molecule. Angptl4 has been unambiguously established as potent inhibitors of blood plasma triglyceride (TG) clearance, causing elevation of plasma TG levels. Recent evidence indicates that variations in the sequence of the Angptl4 polypeptide impact the effect on triglycerides, with certain mutations conferring reduced triglyceride levels implying a decreased inhibition of LPL (33 and 34, each of which are incorporated by reference for the teaching of Angptl4 variants). Furthermore, it has been reported that Angptl4 polypeptides exist in oligomeric forms and that oligomerization is required for inhibition of LPL activity. Once secreted from the cell, the oligomeric form is cleaved at a cleavage site ($R_{161}RKR_{164}$ of SEQ ID NOS: 1 and 3) to provide monomeric C-terminal forms and oligomeric N-terminal forms (34). The N-terminal residues 1-187 of the Angptl4 peptide were found to be sufficient to inhibit LPL (33).

The amino acid and cDNA sequences of the human, rat and mouse are provided in FIG. 5 and designated SEQ ID NOS: 1-8. The present disclosure contemplates the use of Angptl4 polypeptides and polypeptide derivatives in the methods disclosed herein, such as but not limited to, methods of treatment and prevention. As defined herein an Angptl4 polypeptide derivative refers to an Angptl4 polypeptide that includes one or more insertions, deletions and/or substitutions as determined from the amino acid sequence of the human polypeptides shown in SEQ ID NOS: 1 or 3 or the polypeptides shown in SEQ ID NOS: 5 or 7.

Some embodiments of the Angptl14 derivative comprise a core structure that is a consensus sequence between any two or more of SEQ ID NOS: 1, 3, 5, or 7, with one or more substitutions as described herein. One embodiment of the Angptl14 derivative comprises the consensus sequence between SEQ ID NOS: 1 and 3 (both version of human Angptl14); the consensus sequence comprising:

A-B-C in which A is at least 80% homologous to SEQ ID NO: 26, B is an oligopeptide of 0-38 residues (an optional linking region), and C is at least 80% homologous to SEQ ID NO: 27. The level of homology of A to SEQ ID NO: 26 and of C to SEQ ID NO: 27 may of course be higher than 80%. These levels of homology may be independently selected from 80-100%, for example 85%, 90%, 95%, 99%, 99.5%, and 100%. The sequence of oligopeptide B may be any sequence. Some embodiments of oligopeptide B are at least 50% homologous to positions 184-222 of SEQ ID NO: 1. In such embodiments the level of homology may be selected from any point in the range of 50-100%, including for exemplary purposes 60%, 70%, 80%, 85%, 90%, 95%, 99%, 99.5%, and 100%.

Another embodiment of the Angptl14 derivative comprises a consensus sequence between all of SEQ ID NOS: 1, 3, 5, AND 7 (human variant, rat and mouse); the consensus sequence comprising:

V-W-X-Y-Z in which V has at least 80% homology to SEQ ID NO: 23, W is an oligopeptide of 0-5 residues, X has at least 80% homology to SEQ ID NO: 24, Y is an oligopeptide of 0-38 residues (an optional linking region), and Z has at least 80% homology to SEQ ID NO: 25. The levels of homology of V to SEQ ID NO: 23, X to SEQ ID NO 24, and Z to SEQ ID NO: 25 may be higher than 80%. These levels of homology may be independently selected from 80-100%, for example 85%, 90%, 95%, 99%, 99.5%, and 100%. The sequence of oligopeptide Y may be any sequence. Some embodiments of oligopeptide B are at least 50% homologous to positions 184-222 of SEQ ID NO: 1. In such embodiments the level of homology may be selected from any point in the range of 50-100%, including for exemplary purposes 60%, 70%, 80%, 85%, 90%, 95%, 99%, 99.5%, and 100%.

These consensus sequences allow for substitutions at positions corresponding to positions 39, 40, 46, 50, and 53 of SEQ ID NO: 1, which as taught in this disclosure may serve to reduce LPL inhibitory activity. They also allow for substitutions at positions corresponding to positions 63-66 of SEQ ID NO: 1, which as taught in this disclosure may serve to increase the protein's resistance to cleavage. They also allow for substitutions at positions corresponding to SEQ ID NO: 1 positions 5, 67, 72, 77, 167, 174, 190, 230, 233, 237, 251, 266, 278, 291, 293, 296, 307, 308, 336, 338, 349, 361, 371, and 384, as these were revealed to be sites of known natural human variants by a search on UniProt (www.uniprot.org). Specific embodiments of the Angptl4 derivative comprise one or more of the following substitutions at these positions: P5L, S67R, R72L, G77R, E167K, P174S, E190Q, E196K, R230C, G233R, F237V, P251T, T266M, R278Q, V291M, L293M, E296V, P307S, V308M, R336C, D338E, W349C, G361R, G361S, R371Q, and R384W. Such naturally occurring substitutions would be expected to preserve the function of the protein.

In one embodiment, amino acid residues of the Angptl4 polypeptide are removed and replaced with different amino acid residues. The variants may be constructed as described herein or as known in the art. The variants so constructed may be evaluated using the methods and assays described herein to screen for activity.

When used herein, single letters when used to refer to amino acids have the following meanings:

| G | Glycine | P | Proline | W | Tryptophan | H | Histidine |
|---|---|---|---|---|---|---|---|
| A | Alanine | V | Valine | K | Lysine | R | Arginine |
| L | Leucine | I | Isoleucine | Q | Glutamine | N | Asparagine |
| M | Methionine | C | Cysteine | E | Glutamic Acid | D | Aspartic Acid |
| F | Phenylalanine | Y | Tyrosine | S | Serine | T | Threonine |

In one embodiment, the variant comprises a change in the amino acid sequence of an Angptl4 polypeptide that decreases the ability of Angptl4 to inhibit LPL or to or to be resistant to cleavage. The change may be a replacement, deletion and/or substitution of one or more residues in this region. Such changes have been described in the art (see references 33 and 34 which are herein incorporated by reference for such teaching). In one embodiment, such change occurs in residues 1-187 with respect to SEQ ID NO: 1, residues 1-182 of SEQ ID NO: 3, residues 1-182 of SEQ ID NO: 26, any residues in SEQ ID NO: 23, and residues 1-79 in SEQ ID NO: 24.

Some embodiments of the derivative of the Angptl4 polypeptide derivative differ from the human wild-type sequence at positions 39-55 of SEQ ID NO: 1 (DEMNVLAHGLLQLGQGL); this region corresponds to positions 39-55 of SEQ ID NOS: 1, 3, 5, 7, 23, and 26. Additional embodiments of the derivative comprise a sequence at positions 39-55 that is neither DEMNVLAHGLLQLGQGL (positions 39-55 of SEQ ID NO: 1) nor DKMNVLAHGLLQLGQGL (SEQ ID NO: 28). Further embodiments of the Angptl4 polypeptide derivative have at least one substitution at positions 39, 40, 46, 50, and 53, such that positions 39-40 of V is not DE, position 46 of V is not H, position 50 of V is not Q, and position 53 of V is not Q.

In some embodiments, such change occurs at position 40 with respect to SEQ ID NOS: 1, 3, 5, 7, 23, or 26. In one embodiment, the amino acid at position 40 (a negatively charged glutamic acid residue in wild-type Angptl4) is replaced with a neutral amino acid or a positively charged amino acid. In a particular embodiment, the change is an E40K substitution. In another particular embodiment, the change is an E40A substitution. The E40K and E40A substitutions have been shown to reduce LPL inhibition by Angptl4, but not interfere with expression, secretion, processing and other functions of the polypeptide. In a further particular embodiment, the change at position 40 is selected from those shown in Table 1 below. In yet a further embodiment, the amino acid at position 39 of SEQ ID NOS: 1, 3, 5, 7, 23, or 26 (a negatively charged aspartic acid residue in wild-type Angptl4) is replaced with a neutral or positively charged amino acid. In one embodiment, the substitution is a D39K substitution of a D39A substitution. In a further particular embodiment, the change at position 39 of SEQ ID NOS: 1, 3, 5, 7, 23, or 26 is selected from those shown in Table 1 below. In certain embodiments, a polypeptide variant may contain one of the aforementioned changes at position 40, one of the aforementioned changes at position 39 or a combination of the foregoing. In a particular embodiment, the polypeptide contains a D39K substitution and a E40K substitution, a D39A substitution and a E40K substitution or a D39K substitution and an E40A substitution. In a further specific embodiment the polypeptide derivative the sequence at positions 39-40 is selected from the group consisting of: DK, KE, DA, and AE. In yet another embodiment the polypeptide derivative the sequence at positions 39-40 is not DE.

TABLE 1

Modifications of $D_{39}$ and $E_{40}$ in the human Angptl4 protein

| G | P | V | L | I | M | C | F | Y |
|---|---|---|---|---|---|---|---|---|
| W | H | R | Q | N | S | T | | |

In another embodiment, the derivative comprises one or more changes in a region of the Angptl4 polypeptide responsible for cleavage of the polypeptide. In one embodiment, this region is the $R_{161}RKR_{164}$ region of Angptl4 (corresponding to positions 161-164 of SEQ ID NOS: 1, 3, 5, 7, and 26; and positions 63-66 of SEQ ID NO: 24). The change may be a replacement, deletion and/or substitution of one or more residues in this region. The $R_{161}RKR_{164}$ region has been shown to be responsible for cleavage of the oligomeric forms of Angptl4, releasing oligomers of the N-terminal sequences and monomers of the C-terminal sequence. Forms of Angptl4 with a mutated cleavage site were shown to accumulate at higher levels in the circulation than wild-type polypeptide. Furthermore, preventing cleavage of the Angptl4 polypeptide stabilizes the oligomeric forms of Angptl4 observed to be efficacious in the present disclosure. In one embodiment, all 4 amino acid residues of the $R_{161}RKR_{164}$ region are changed, such that the sequence, is not RRKR; in an alternate embodiment, any 1, 2 or 3 amino acid residues of the $R_{161}RKR_{164}$ region are changed. In a further embodiment, the arginine residues at positions 161, 162 or 164 are independently substituted with glycine, alanine, valine or serine and the lysine residue at position 163 is substituted with glycine, alanine, valine or serine. In a specific embodiment the $R_{161}RKR_{164}$ sequence is replaced with a sequence selected from the group consisting of: GAAG (SEQ ID NO: 29), GSGS (SEQ ID NO: 80), GVVA (SEQ ID NO: 49), SGGG (SEQ ID NO: 87), and VAVA (SEQ ID NO: 90). In a further specific embodiment the $R_{161}RKR_{164}$ sequence is replaced with AAVV. Exemplary amino acid sequences for replacement of the entire $R_{161}RKR_{164}$ region of SEQ ID NOS: 1 or 3 is provided in Table 2 below.

TABLE 2

| Modifications of $_{161}RRKR_{164}$ in the Angptl4 protein or derivatives | |
|---|---|
| SEQ ID | |
| 29 | GAAG |
| 30 | GAGA |
| 31 | GGAA |
| 32 | AGGA |
| 33 | AGAG |
| 34 | AAGG |
| 35 | VGAA |
| 36 | VAAG |
| 37 | VAGA |
| 38 | GAAV |
| 39 | GAVA |
| 40 | GVAA |
| 41 | AGVA |
| 42 | AGAV |
| 43 | AAVG |
| 44 | AAGV |
| 45 | AVAG |
| 46 | AVGA |
| 47 | GAVV |
| 48 | GVAV |
| 49 | GVVA |
| 50 | AGVV |
| 51 | AVVG |
| 52 | AVGV |
| 53 | VGAV |
| 54 | VGVA |
| 55 | VAGV |
| 56 | GVVV |
| 57 | VGVV |
| 58 | VVVG |
| 59 | VVGV |
| 60 | VAVG |
| 61 | VVGA |
| 62 | VVAG |
| 63 | VVVA |
| 64 | VVAV |
| 65 | GAAA |
| 66 | AGAA |

TABLE 2-continued

Modifications of $_{161}$RRKR$_{164}$ in the Angptl4 protein or derivatives

| SEQ ID | |
|---|---|
| 67 | AAAG |
| 68 | AAGA |
| 69 | AAVV |
| 70 | AAVA |
| 71 | AAAV |
| 72 | AVAA |
| 73 | VAAA |
| 74 | AVVV |
| 75 | VAVV |
| 76 | VVVV |
| 77 | SSSS |
| 78 | GGGG |
| 79 | AAAA |
| 80 | GSGS |
| 81 | GSSG |
| 82 | GGSS |
| 83 | SGSG |
| 84 | SGGS |
| 85 | SSGG |
| 86 | GSGG |
| 87 | SGGG |
| 88 | GGSG |
| 89 | GGGS |
| 90 | VAVA |

In a further embodiment, one or more of the amino acids in the $R_{161}RKR_{164}$ sequence is altered to remove a consensus binding site of an enzyme capable of cleaving Angplt4, such that Angptl4 is resistant to cleavage. In one embodiment, the enzyme is a proprotein convertase and the consensus binding site is RXKR, RXRR, RR or KR, where X is any amino acid. In making such alternations, one or more amino acids may be deleted or substituted with glycine, alanine, valine or serine or with any of the other substitutions discussed herein.

In still a further embodiment, the variant comprises one or more changes in a region of the Angptl4 polypeptide responsible for oligomerization of the polypeptide. In one embodiment, this region is the $C_{76}$ and/or $C_{80}$ region of Angptl4. The $C_{76}$ and/or $C_{80}$ region has been shown to be involved in oligomerization of the Angptl4 polypeptide (34, which reference is incorporated herein for such teaching). The change may be a replacement, deletion and/or substitution of one or more residues in this region. In a particular embodiment, only one of the cysteine residues at positions 76 and 80 is substituted; in an alternate embodiment, both cysteine residues at positions 76 and 80 are both substituted. In one embodiment, at least one of the cysteine residues at position 76 and 80 are substituted independently with alanine or serine; in another embodiment, both cysteine residues are substituted with alanine or serine.

In a further embodiment, the variant comprises one or more changes in the $R_{161}RKR_{164}$ region of Angplt4 that inhibits the cleavage of the Angptl4 polypeptide oligomer and a change at position 40 that reduces inhibition of LPL activity by Angptl4. Any of the changes discussed herein are included.

In one embodiment, the present disclosure provides for Angptl4 polypeptide variants having the amino acid sequence of SEQ ID NOS: 9 or 10. SEQ ID NO: 9 is shown in FIG. 4 and includes the wild type sequence of Angptl4 from SEQ ID NO: 1, with the exception of substitutions at positions 39, 40, 76, 80 and 161-164 indicated by $X_{39}$, $X_{40}$, $X_{76}$, $X_{80}$, $X_{161}$, $X_{162}$, $X_{163}$ and $X_{164}$, respectively. SEQ ID NO: 10 is shown in FIG. 4 and includes the wild type sequence of Angptl4 from SEQ ID NO: 3, with the exception of substitutions at positions 39, 40, 76, 80 and 161-164 indicated by $X_{39}$, $X_{40}$, $X_{76}$, $X_{80}$, $X_{161}$, $X_{162}$, $X_{163}$ and $X_{164}$, respectively.

In SEQ ID NOS: 9 and 10, $X_{39}$ may be A, G, P, V, L, I, M, C, F, Y, W, H, R, Q, N, S, T or K. In one embodiment, $X_{39}$ is a neutral or positively charged amino acid. In a further embodiment, $X_{39}$ may be A or K. In still a further embodiment, $X_{39}$ may be D.

In SEQ ID NOS: 9 and 10, $X_{40}$ may be A, G, P, V, L, I, M, C, F, Y, W, H, R, Q, N, S, T or K. In one embodiment, $X_{40}$ is a neutral or positively charged amino acid. In a further embodiment, $X_{40}$ may be A or K. In still a further embodiment, $X_{40}$ may be E. In yet a further embodiment, $X_{40}$ may be E when $X_{39}$ is not D and $X_{39}$ may be D when $X_{40}$ is not E.

In SEQ ID NOS: 9 and 10, at least one of $X_{76}$ and $X_{80}$ may be substituted. In one embodiment, $X_{76}$ and $X_{80}$ are independently A or S or C. In one embodiment, one of $X_{76}$ and $X_{80}$ may be A or S and the other of $X_{76}$ and $X_{80}$ is C. In a further embodiment, both of $X_{76}$ and $X_{80}$ may be independently A or S. In still a further embodiment, both of $X_{76}$ and $X_{80}$ may C.

In SEQ ID NOS: 9 and 10, at least one of $X_{161}$, $X_{162}$, $X_{163}$ and $X_{164}$ may be substituted. In one embodiment, all 4 of $X_{161}$, $X_{162}$, $X_{163}$ and $X_{164}$ are substituted; in an alternate embodiment, 1, 2 or 3 of $X_{161}$, $X_{162}$, $X_{163}$ and $X_{164}$ are substituted. In a further embodiment, $X_{161}$, $X_{162}$, $X_{163}$ and $X_{164}$ are independently D, R, K, G, A, V or S. In still a further embodiment, all 4 of are substituted with the combinations recited in Table 2.

The present disclosure contemplates combinations of the foregoing in any form. Furthermore, the designated residues in SEQ ID NOS: 9 and 10 may be substituted with conservative amino acid substitutions as designated in Table 3, or with residues having a difference in hydropathic index of +/−1 or less or with residues having a difference in hydrophilicity values of +/−1 or less.

In a one embodiment, $X_{39}$ is D, $X_{40}$ is A or K, $X_{76}$ and $X_{80}$ are C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is D, $X_{40}$ is A or K, $X_{76}$ and $X_{80}$ are C and $X_{161}$, $X_{162}$, $X_{163}$ and $X_{164}$ are selected from the combinations shown in Table 2. In still another embodiment, $X_{39}$ is D, $X_{40}$ is A or K, $X_{76}$ and $X_{80}$ are C and $X_{161}$, $X_{162}$, $X_{163}$ and $X_{164}$ are GSGS or GAAG.

In an additional embodiment, $X_{39}$ is D, $X_{40}$ is A or K, one of $X_{76}$ and $X_{80}$ is A or S and the other of $X_{76}$ and $X_{80}$ is C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In a further embodiment, $X_{39}$ is D, $X_{40}$ is A or K, one of $X_{76}$ and $X_{80}$ is A or S and the other of $X_{76}$ and $X_{80}$ is C and $X_{161}$, $X_{162}$, $X_{163}$ and $X_{164}$ are selected from the combinations shown in Table 2. In still a further embodiment, $X_{39}$ is D, $X_{40}$ is A or K, one of $X_{76}$ and $X_{80}$ is A or S and the other of $X_{76}$ and $X_{80}$ is C and $X_{161}$, $X_{162}$, $X_{163}$ and $X_{164}$ are GSGS or GAAG.

In one embodiment, $X_{39}$ is A or K, $X_{40}$ is E, $X_{76}$ and $X_{80}$ are C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is A or K, $X_{40}$ is E, $X_{76}$ and $X_{80}$ are C and $X_{161}$, $X_{162}$, $X_{163}$ and $X_{164}$ are selected from the combinations shown in Table 2. In still another embodiment, $X_{39}$ is A or K, $X_{40}$ is E, $X_{76}$ and $X_{80}$ are C and $X_{161}$, $X_{162}$, $X_{163}$ and $X_{164}$ are GSGS or GAAG.

In one embodiment, $X_{39}$ is D, $X_{40}$ is K, $X_{76}$ and $X_{80}$ are C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is D, $X_{40}$ is K, $X_{76}$ and $X_{80}$ are C and $X_{161}$, $X_{162}$, $X_{163}$ and $X_{164}$ are selected from the combinations shown in Table 2. In still another embodiment, $X_{39}$ is D, $X_{40}$ is K, $X_{76}$ and $X_{80}$ are C and $X_{161}$, $X_{162}$, $X_{163}$ and $X_{164}$ are GSGS or GAAG.

In one embodiment, $X_{39}$ is D, $X_{40}$ is K, one of $X_{76}$ and $X_{80}$ is A or S and the other of $X_{76}$ and $X_{80}$ is C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is D, $X_{40}$ is K, one of $X_{76}$ and $X_{80}$ is A or S and the other of $X_{76}$ and $X_{80}$ is C and $X_{161}$, $X_{162}$, $X_{163}$ and $X_{164}$ are selected from the combinations shown in Table 2. In still another embodiment, $X_{39}$ is D, $X_{40}$ is K, one of $X_{76}$ and $X_{80}$ is A or S and the other of $X_{76}$ and $X_{80}$ is C and $X_{161}$, $X_{162}$, $X_{163}$ and $X_{164}$ are GSGS or GAAG.

In one embodiment, the Angplt4 derivative is based on a fragment of Angplt4. Suitable fragments include any fragment that retains the activity of wild type Angplt4 or any fragment of 100 or more consecutive amino acids. In one embodiment, such fragment is based on amino acids 1-187 SEQ ID NO: 1 or amino acids 1-182 of SEQ ID NO: 3. Such fragments may have the amino acid substitutions described in the preceding paragraphs.

The Angptl4 polypeptide derivative may have an activity that is comparable to or increased (in one embodiment, 50% or more) as compared to the wild-type Angptl4 polypeptide activity; alternatively, the Angptl4 polypeptide derivative may have an activity that is decreased (in one embodiment, less than 50%) as compared to the wild-type Angptl4 polypeptide activity. In a specific embodiment, the Angptl4 polypeptide derivative has a decreased ability to inhibit LPL and shows an increased resistance to cleavage.

The deletions, additions and substitutions can be selected, as would be known to one of ordinary skill in the art, to generate a desired Angptl4 polypeptide derivative. For example, conservative substitutions or substitutions of amino acids with similar properties are expected to be tolerated. In addition, specific deletions, insertions and substitutions may impact, positively or negatively, a certain Angptl4 polypeptide activity but not impact a different Angptl4 polypeptide activity.

Conservative modifications to the amino acid sequence of any of SEQ ID NOS: 1 or 3 or 5 or 7, including combinations thereof (and the corresponding modifications to the encoding nucleotides) will produce Angptl4 polypeptide derivatives having functional and chemical characteristics similar to those of naturally occurring Angptl4 polypeptides while minimizing undesirable properties such as LPL inhibitory activity. In contrast, substantial modifications in the functional and/or chemical characteristics of Angptl4 polypeptides may be accomplished by selecting substitutions in the amino acid sequence of any of SEQ ID NOS: 1 or 3 or 5 or 7, including combinations thereof, that differ significantly in their effect on maintaining (a) the structure of the molecular backbone in the area of the substitution.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine.

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

For example, non-conservative substitutions may involve the exchange of a member of one of these classes for a member from another class. Such substituted residues may be introduced into regions of the Angptl4 polypeptide derivatives that are homologous with non-human Angptl4 polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (Kyte et al., J. Mol. Biol., 157:105-131, 1982). It is known that certain amino acids may be substituted for other amino acids having a similar hydropathic index or score and still retain a similar biological activity.

In making changes based upon the hydropathic index, the substitution of amino acids whose hydropathic indices are within +/−2 may be used; in an alternate embodiment, the hydropathic indices are with +/−1; in yet another alternate embodiment, the hydropathic indices are within +/−0.5.

It is also understood in the art that the substitution of like amino acids can be made effectively on the basis of hydrophilicity. The greatest local average hydrophilicity of a polypeptide as governed by the hydrophilicity of its adjacent amino acids, correlates with a biological property of the protein.

The following hydrophilicity values have been assigned to amino acid residues: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +/−2 may be used; in an alternate embodiment, the hydrophilicity values are with +/−1; in yet another alternate embodiment, the hydrophilicity values are within +/−0.5.

Desired amino acid substitutions (whether conservative or non-conservative) can be determined by those skilled in the art at the time such substitutions are desired. For example, amino acid substitutions can be used to identify important residues of the Angptl4 polypeptide, or to increase or decrease the affinity of the Angptl4 polypeptide with a particular binding target in order to increase or decrease an Angptl4 polypeptide activity.

Exemplary amino acid substitutions are set forth in Table 3.

TABLE 3

Amino Acid Substitutions

| Original Amino Acid | Exemplary substitution | Preferred substitution |
|---|---|---|
| Ala | Val, Leu, Ile | Val |
| Arg | Lys, Gln, Asn | Lys |
| Asn | Glu | Glu |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Ile, Val, Met, Ala, Phe, Norleucine | Ile |
| Lys | Arg, 1,4-diaminobutyric acid, Gln, Asn | Arg |
| Met | Leu, Phe, Ile | Leu |
| Phe | Leu, Val, Ile, Ala, Tyr | Leu |
| Pro | Ala, Gly | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NOS: 1, 3, 5, 7, 9, 10, and 23-27, including combinations thereof, using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an Angptl4 polypeptide to such similar polypeptides. With such a comparison, one can identify residues and portions of the molecules that are conserved among similar polypeptides. It will be appreciated that changes in areas of an Angptl4 polypeptide that are not conserved relative to such similar polypeptides would be less likely to adversely affect the biological activity and/or structure of the Angptl4 polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an Angptl4 polypeptide that correspond to amino acid residues that are important for activity or structure in similar polypeptides. One skilled in the art may opt for chemically similar amino acid substitutions for such predicted important amino acid residues of an Angptl4 polypeptide.

One skilled in the art can also analyze the three-dimensional structure and amino acid sequence in relation to that structure in similar polypeptides. In view of that information, one skilled in the art may predict the alignment of amino acid residues of an Angptl4 polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test Angptl4 polypeptide derivatives containing a single amino acid substitution at each desired amino acid residue. The derivatives can then be screened using activity assays know to those skilled in the art and as disclosed herein. Such derivatives could be used to gather information about suitable substitution. For example, if one discovered that a change to a particular amino acid residue resulted in destroyed, undesirably reduced, or unsuitable activity, derivatives with such a change would be avoided. In other words, based on information gathered from such routine experiments, one skilled in the art can readily determine the amino acids where further substitutions should be avoided either alone or in combination with other mutations.

Numerous scientific publications have been devoted to the prediction of secondary structure from analyses of amino acid sequences (see Chou et al., Biochemistry, 13(2):222-245, 1974; Chou et al., Biochemistry, 113(2):211-222, 1974; Chou et al., Adv. Enzymol. Relat. Areas Mol. Biol., 47:45-148, 1978; Chou et al., Ann. Rev. Biochem., 47:251-276, 1979; and Chou et al., Biophys. J., 26:367-384, 1979). Moreover, computer programs are currently available to assist with predicting secondary structure of polypeptides. Examples include those programs based upon the Jameson-Wolf analysis (Jameson et al., Comput. Appl. Biosci., 4(1): 181-186, 1998; and Wolf et al., Comput. Appl. Biosci., 4(1):187-191; 1988), the program PepPlot® (Brutlag et al., CABS, 6:237-245, 1990; and Weinberger et al., Science, 228:740-742, 1985), and other new programs for protein tertiary structure prediction (Fetrow. et al., Biotechnology, 11:479-483, 1993).

Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure (see Holm et al., Nucl. Acid. Res., 27(1):244-247, 1999).

Additional methods of predicting secondary structure include "threading" (Jones, D., Curr. Opin. Struct. Biol., 7(3):377-87, 1997; Suppl et al., Structure, 4(1):15-9, 1996), "profile analysis" (Bowie et al., Science, 253:164-170, 1991; Gribskov et al., Meth. Enzym., 183:146-159, 1990; and Gribskov et al., Proc. Nat. Acad. Sci., 84(13): 4355-4358, 1987), and. "evolutionary linkage" (See Home, supra, and Brenner, supra).

Any of the polypeptide forms discussed herein may also contain a sequence useful in the identification or purification of the polypeptide; an example of such a sequence is the C-terminal V5 tag. The foregoing also includes nucleic acid sequences (such as, but not limited to cDNA sequences) coding for such polypeptides, including polypeptide derivatives as described herein.

Compositions

Useful compositions of the present disclosure may comprise one or more polypeptides of the present disclosure useful in the treatment and prevention methods of the present disclosure; useful compositions also include one or more nucleic acids coding for one or more polypeptides of the present disclosure useful in the treatment and prevention methods of the present disclosure. The compositions disclosed may comprise one or more of such compounds, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). To form a pharmaceutically acceptable composition suitable for administration, such compositions will contain an therapeutically effective amount of compound.

The pharmaceutical compositions of the disclosure may be used in the treatment and prevention methods of the present disclosure. Such compositions are administered to a subject in amounts sufficient to deliver a therapeutically effective amount of the compound(s) so as to be effective in the treatment and prevention methods disclosed herein. The therapeutically effective amount may vary according to a variety of factors such as, but not limited to, the subject's condition, weight, sex and age. Other factors include the mode and site of administration. The pharmaceutical compositions may be provided to the subject in any method known in the art. Exemplary routes of administration include, but are not limited to, subcutaneous, intravenous, topical, epicutaneous, oral, intraosseous, and intramuscular. The compositions of the present disclosure may be administered only one time to the subject or more than one time to the subject. Furthermore, when the compositions are administered to the subject more than once, a variety of regimens may be used, such as, but not limited to, one per day, once per week or once per month. The compositions may also be administered to the subject more than one time per day. The therapeutically effective amount and appropriate dosing regimens may be identified by routine testing in order to obtain optimal activity, while minimizing any potential side effects. In addition, co-administration or sequential administration of other agents may be desirable.

The therapeutically effective amount may be a range of ratios between the mass of the compound and the mass of the subject. In some embodiments of the compositions the therapeutically effective amount is about 0.005-150,000 µg/kg, 0.5-15,000 µg/kg, 5-1500 µg/kg, or 50-150 µg/kg. Thus, for a typical 70 kg human adult, the therapeutically effective amount may be 0.0035-11,000 mg, 0.035-1100 mg, 0.35-110 mg, or 3.5-11 mg. Administration may occur on a regular schedule.

The compositions of the present disclosure may be administered systemically, such as by intravenous administration, or locally such as by subcutaneous injection or by application of a paste or cream. In some embodiments of the composition containing an Angptl4 polypeptide or derivative, the pharmaceutical will be suitable for delivery of the polypeptide to the blood. Such suitable types of pharmaceuticals include intravenous formulations, intramuscular formulations, transdermal pastes or creams, transdermal patches, suppositories, and oral dosages forms that protect the polypeptide from digestion.

In one embodiment, a nucleic acid, which may be in the form of a suitable plasmid or vector, is provided that codes for an Angptl4 polypeptide or Angptl4 polypeptide variant of the present disclosure. Such nucleic acid is introduced into a cell, which may be obtained from the subject, by suitable methods known in the art (for example, electroporation). In one embodiment, the cell is an adipose cell. The cells may be assayed for expression of the Angptl4 polypeptide or polypeptide derivative (in one embodiment, expression of the polypeptide can be determined by the presence of a tag on the polypeptide as discussed herein). The cells expressing an Angptl4 polypeptide of polypeptide derivative may then be introduced into the subject. In one embodiment, the cells are administered to the subject by subcutaneous injection; other methods of administration may also be used, including those discussed herein. The cells then express Angptl4 polypeptide or an Angptl4 polypeptide derivative, which is taken up into the circulation.

The compositions of the present disclosure may further comprise agents which improve the solubility, half-life, absorption, etc. of the compound(s). Furthermore, the compositions of the present disclosure may further comprise agents that attenuate undesirable side effects and/or or decrease the toxicity of the compounds(s). Examples of such agents are described in a variety of texts, such a, but not limited to, Remington: The Science and Practice of Pharmacy (20$^{th}$ Ed., Lippincott, Williams & Wilkins, Daniel Limmer, editor).

The compositions of the present disclosure can be administered in a wide variety of dosage forms for administration. For example, the compositions can be administered in forms, such as, but not limited to, tablets, capsules, sachets, lozenges, troches, pills, powders, granules, elixirs, tinctures, solutions, suspensions, elixirs, syrups, ointments, creams, pastes, emulsions, or solutions for intravenous administration or injection. Other dosage forms include administration transdermally, via patch mechanism or ointment. Any of the foregoing may be modified to provide for timed release and/or sustained release formulations.

In the present disclosure, the pharmaceutical compositions may further comprise a pharmaceutically acceptable carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the compound(s) may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For oral liquid forms, such as but not limited to, tinctures, solutions, suspensions, elixirs, syrups, the nucleic acid molecules of the present disclosure can be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing for delivery directly to the site of a wound or cutaneous injury.

The compound(s) of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The compound(s) of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

WORKING EXAMPLES

In the following results, the methods used were those methods specified in the Methods section of the present disclosure and the references cited therein. Some of the following results are described in Clement L C et. al., "Podocyte secreted Angiopoietin-like 4 mediates proteinuria in glucocorticoid-sensitive nephrotic syndrome," *Nature Medicine*, January 2011 (this reference is hereby incorporated by reference for the disclosure contained therein regarding the use of Angptl4 polypeptides).

1. Patients with Nephrotic Syndrome have Increased Levels of Circulating Angptl4

Patients with Nephrotic syndrome have increased circulating levels of Angptl4 polypeptide. 200 µg human plasma from patients (n=4 patients/group) with diagnosed with MCD and MN and patients in MCD relapse were analyzed by 2D gel electrophoresis and Western blots were prepared using anti-Angptl4 antibodies (FIG. 1A). FIG. 1A shows that only patients with MCD relapse and MN had increased levels of Angptl4 (indicated by arrows). This form of Angptl4 exists as a neutral pI form and is present as monomers and oligomers.

2. aP2-Angptl4 TG Rats have Increased Circulating Levels of Angptl4

A transgenic rat models for adipocyte specific Angptl4 overexpression was developed and is shown in FIG. 1B (aP2-Angptl4 TG). Analysis of mRNA expression in organs that normally express Angptl4 confirmed specificity of expression, with Angplt4 being detected in brown adipose tissue (BAT) and white adipose tissue (WAT) (FIG. 1C).

2D gel electrophoresis of 200 µg plasma, followed by Western blotting using an anti-Angptl4 antibody revealed that heterozygous aP2-Angptl4 TG rats had higher circulating Angptl4 levels than wild type rats (FIG. 10) (age 3 months, n=3 blots/group). FIG. 1E shows 2D gel electrophoresis of 200 µg plasma, followed by Western blotting using anti-Angptl4 and anti-V5 antibodies show the presence of adipose tissue secreted V5-tagged Angptl4 in the plasma of aP2-Angptl4 TG rats. 2D gel electrophoresis of immunoprecipitated Angptl4 from aP2-Angptl4 TG rat plasma (using an antibody specific for the N-terminus of Angptl4), followed by Western blotting using anti-Angptl4 or anti-lectin. SNA I antibodies revealed the presence of sialylated Angptl4 polypeptide in the circulation.

The aP2-Angptl4 TG rats had morphologically normal glomeruli by light (FIG. 1G) and electron microscopy (not shown), and glomerular Angptl4 expression was unchanged. This is in contrast to podocyte specific expression of Angptl4, where such expression resulted in glomerular defects, including progressive development of foot process effacement between age one to five months (see U.S. Provisional application No. 61/351,865 (filed 5 Jun. 2010), which is hereby incorporated by reference for such teaching).

Immunogold EM using anti-V5 antibody to specifically detect transgene expressed protein in 3 month old heterozygous aP2-Angptl4 TG male rats demonstrated detection selectively on the endothelial surface, indicating that circulating Angptl4 middle and high order oligomers do not enter the GBM and have receptors on the endothelial surface. The effects of circulating Angptl4 is relevant to both human and experimental nephrotic syndrome, since adipose tissue upregulation of Angptl4 is noted in later stages of nephrotic syndrome, when proteinuria is on the decline.

3. Relationship of Increased Circulating Levels of Angptl4 with Proteinuria and Albuminuria To examine the relationship between circulating levels of Angptl4 proteinuria, including albuminuria, proteinuria was analyzed in aP2-Angptl4 TG rats. FIG. 2A shows that that aP2-Angptl4 TG do not exhibit proteinuria as determined by analysis of urinary proteins. In FIG. 2A urinary proteins were analyzed by GelCode blue stained SDS PAGE (3 µg/lane, except MCD remission) (densitometry readings are provided under each lane). The intact albumin band is observed at 70 kDa (indicated by arrow). As can be seen, WT rats, aP2-Angptl4 TG rats and MCD patients in remission showed little or no intact albumin in the analysed urinary samples, wherein NPHS2-Angplt4 TG rats (a rat transgenic model having podocytes specific Angptl4 expression and shown to develop MCD with proteinuria; see U.S. Provisional application No. 61/351,865 (filed 5 Jun. 2010), which is hereby incorporated by reference for such teaching), MCD relapse, MN relapse and PAN rats (a rat model of nephrotic syndrome) showed strong albumin staining indicative of albuminuria. FIG. 2B shows that female heterozygous aP2-Angptl4 female TG rats had decreased albuminuria as compared to WT littermate controls. FIG. 2C shows the same results for aP2-Angptl4 heterozygous male TG rats. FIG. 2D shows that aP2-Angptl4 TG rats exhibited reduced proteinuria in the puromycin nephrosis (PAN model; a rat model of nephrotic syndrome) as compared to WT littermates. As demonstrated above, aP2-Angptl4 TG rats have higher circulating Angptl4 levels that migrate at or around neutral isoelectric point, and is sialylated. These results show a role for circulating Angptl4 in reducing proteinuria and nephrotic syndrome.

Since endothelial binding of adipose tissue secreted Angptl4 bound to glomerular endothelium, experiments were conducted to determine the effect of recombinant Angptl4 on glomerular epithelial cells (GEnCs) to investigate whether lower baseline albuminuria and less PAN induced proteinuria in this rat model were mediated by glomerular endothelial protection. GEnCs were subject to oxidative injury by addition of hydrogen peroxide and into the culture media and incubated with concentrated supernatant (600 µg/well) from the control stable cell line, Angptl4-HEK293 cell line (secreting high isoelectric point (pI), hyposialylated Angptl4) or Angptl4-HEK293 cell line incubated with ManNAc (neutral pI, normally sialylated Angptl4). It should be noted that the high pI form of Angptl4 is secreted in large amounts from podocytes in MCD. Release of LDH was assessed as a marker of cell injury. Control cells without hydrogen peroxide injury were given a relative score of 1. High pI Angptl4 increased GEnC injury, whereas neutral pI Angptl4 (which comprises most of circulating Angptl4) was significantly protective at all measured time points. (n=3 readings/condition).

Upregulation of Angptl4 in wild type rats on PAN Day 6 was exclusively glomerular, whereas upregulation in adipose tissue was noted on Day 10 when proteinuria and glomerular Angptl4 expression are on the decline (n=3 rats/sample) (FIG. 2F). Therefore, increases in circulating Angptl4 levels are coincident with the protective effect of circulating Angptl4 in nephrotic syndrome and reduction of proteinuria. The effects of circulating Angptl4 are likely to be relevant to both human and experimental MCD, since adipose tissue upregulation of Angptl4 is noted in later stages of PAN when proteinuria is on the decline. Furthermore, increased circulating Angptl4 levels at baseline and after induction of PAN in aP2-Angptl4 TG rats resulted in increased plasma triglyceride levels (FIG. 2G) and reduced post-heparin lipoprotein lipase activity (FIG. 2H) as compared to wild type rat.

In order to demonstrate the effectiveness of the therapeutic delivery of Angptl4 into the circulation, wild type Angptl4 or a control protein was administered to Buffalo/Mna rats, a model of FSGS, or to Wistar rats in which Thy1.1 nephritis, a short term model of mesangial injury, was induced (FIGS. 4A and B). Wild-type recombinant Angptl4 polypeptide was generated by harvesting of recombinant protein. Angptl4-HEK293 stable or pcDNA3.1-HEK293 control stable cell lines were grown to confluence in 15 cm dishes, washed twice with warm PBS, and incubated with serum free DMEM without Phenol Red, with or without 25 mM ManNAc, for 48 hours. Cells were harvested and the supernatant concentrated. Concentrated supernatant from one 15 cm dish was used at each injection time point.

Buffalo/Mna rats spontaneously develop lesions mimicking human FSGS at around age 2 months, including focal and segmental lesions on light microscopy, effacement of podocyte foot processes on electron microscopy, and proteinuria. The rats develop progressive increase in proteinuria as they age. The rats used in the above studies were male and 5 months old. Anti-Thy1.1 nephritis was induced by injection of 150 µg of anti-Thy1.1 (Ox-7 hybridoma) or control IgG IV into different groups of male Wistar rats (100-125 gm, n 4 rats/group).

In the Buffalo/Mna rat model, assessment of baseline proteinuria was made on Day 0. Angptl4 or control protein were injected intra-peritoneally on two consecutive days (Days 1 & 2, arrows) into Buffalo Mna rats (n=4 rats/group). Proteinuria was assessed on alternate days, and expressed as a percentage of baseline values. Significant reduction in proteinuria was noted in recombinant Angptl4 treated rats.

In the Thy1.1 nephritis model, proteinuria confirmed on Day 1. Rats were injected intravenously with either recombinant Angptl4 or control protein on two consecutive days (Days 1 & 2, arrows). Proteinuria was then assessed. As shown in FIG. 4B, proteinuria was lower in Angptl4 treated rats throughout, and was statistically significant on Day 5.

These results show that therapeutic delivery of Angptl4 into the circulation are an effective treatment for nephrotic syndrome, such as but not limited to minimal change disease, focal segmental glomerulosclerosis, membranous nephropathy/membranous glomerulonephritis, membranoproliferative glomerulonephritis or a diabetic condition, such as, but not limited to, diabetic nephropathy, diabetes mellitus, lupus nephritis or primary glomerular disease. Furthermore, these results show that therapeutic delivery of Angptl4 into the circulation are an effective treatment for and conditions related to nephrotic syndrome, such as but not limited to, proteinuria, hypercholesterolemia, hypertriglyceridemia and edema. In one embodiment, the Angptl4 polypeptide is a derivative with decreased LPL inhibitory activity, resistance to cleavage or a derivative described herein. Administration of such a derivative would retain the beneficial effects of Angptl4 treatment without the negative effects associated with inhibition of LPL activity, such as increased plasma triglyceride levels.

Methods for Examples 1.3

Cloning of Full Length Rat Angptl4, and Generation of Antibody Against Full Length Recombinant Angptl4

The full length rat Angptl4 open reading frame of 1218 bp from our previous experiments (7), excluding the stop codon, was cloned into pcDNA3.1/V5-HisB for eukaryotic expression, and into pET28a for prokaryotic expression. The *E. Coli* expressed purified full length protein was used to generate a polyclonal antibody in rabbits (Proteintech group, Inc. Chicago Ill. USA) that was tested by ELISA and Western blot. Antibody reactive bands were excised from GelCode blue stained gels, trypsin digested and presence of Angptl4 peptide sequences confirmed by MALDI-TOF/TOF. Part of the antiserum was affinity purified to the antigen. Unless otherwise specified, all studies described used this antibody. An additional polyclonal antibody against the N-terminal part of rat Angptl4 (amino acids 7-86 excluding signal peptide) was similarly raised in rabbits.

Induction of Proteinuria in Animal Models of Human Glomerular Disease

All animal studies were approved by the institutional IACUC. Induction of animal models of proteinuria (n=4 rats/group) in WT rats are described in previous publications in parenthesis: PAN (7), PHN (7), PAN with glucocorticoids (20), non-HIV collapsing glomerulopathy (18), nephrotoxic serum induced heterologous phase proteinuria (7). Anti-Thy1.1 nephritis was induced by injection of 200 mcg of anti-Thy1.1 (Ox-7 hybridoma) or control IgG IV into different groups of male Wistar rats (100-125 gm, n=4 rats/group), and rats euthanized after 24 and 72 hours.

The following techniques are described in prior publications: Taqman real time PCR (26), confocal imaging (7), in situ hybridization (27), immunogold EM (26), glomerular extraction and processing for Western blot (26), assessment of charge by PEI method (28). For alcian blue staining, the pH of the staining solution was adjusted to 2.5 using acetic acid, and 0.1% nuclear fast red solution was used as a counterstain. Densitometry of glomerular basement membrane alcian blue stain (20 glomeruli/rat, 3 rats/group) was assessed using Image-Pro software (Media Cybernetics, Inc., Bethesda Md., USA). Densitometry of 2D gel Western blots was assessed using Gel-Pro Analyzer software (Media Cybernetics, Inc.). Taqman real time PCR primers and probes are listed in FIG. 3. For in situ hybridization, the digoxigenin labeled probe for rat Angptl4 included by 1 to 548 of the ORF.

To obtain samples for post heparin LPL activity, rats were injected intravenously with 10 units/100 gm weight of porcine heparin 15 minutes prior to euthanasia, and activity measured using an assay from Roar Biomedical, Inc (New York N.Y.). Serum triglycerides were measured in the fasting state.

Injection of NTS into Angptl4−/− Mice

Angptl4−/− mice were provided to Sander Kersten as a kind gift from Eli Lily Corporation (Indianapolis Ind. USA). The study protocol was approved by the Animal Studies Committee at Wageningen University. Eleven week old male Angptl4−/− or +/+ mice (n=4 mice/group) were injected intravenously with 1.5 mg γ2-NTS or normal sheep serum (Sigma Aldrich St. Louis Mo. USA), spot urine samples collected at 48 hours, mice euthanized at 72 hours, plasma collected for biochemical measurements, and kidneys preserved for histological analysis. Urine albumin was assessed by ELISA (Bethyl laboratories, Montgomery Tex. USA) and urine creatinine measured by mass spectrometry. To assess for foot process effacement, the mean width of foot processes was first measured in control treated Angptl4+/+ mouse transmission electron micrographs (10 equally spaced readings/loop, 3 loops/glomerulus, 3 glomeruli/kidney, 3 kidneys/group). Effacement was described as an over 2.5 fold increase in mean width. Total and effaced foot processes were counted in NTS treated or control treated Angptl4−/− mice.

Studies with Archived Human Samples

Immunostaining of archived human kidney biopsies (n=5 biopsies per condition) was conducted on samples obtained via IRB approved protocols at the Instituto Nacional de Cardiologia, Mexico City. Control kidney biopsies used for these studies were sex and age matched protocol pre-transplant biopsies. Archival human sera for 2D gel electrophoresis and Western blot (n=4 samples/condition) were obtained from a previously published study (29).

Generation of Transgenic Rats aP2-Angptl4 TG rats (adipose tissue specific) construct was generated in the vector that contained the 5.4 Kb mouse aP2 promoter construct (30) (purchased from Addgene Inc. Cambridge Mass. USA) by cloning the rat Angptl4 cDNA (including the signal sequence) with a C-terminal V5 tag at the NotI site just upstream of the polyA tail.

Transgenic rats were generated by microinjection of the digested DNA constructs into fertilized Sprague Dawley eggs (conducted at University of Michigan), implantation into pseudopregnant host Sprague Dawley females, and the resulting offsprings were genotyped by routine PCR and TaqMan genomic DNA real time PCR strategy using construct specific and control genomic prolactin primer and probe combinations (FIG. 3). Three founder lines for adipose tissue specific expression were generated. Data from aP2-Angptl4 TG rat line 375 (3 copies), both stable over 4 generations, are presented. Urinary total protein was assessed using the Bradford method (Biorad laboratories, Hercules Calif. USA), and albuminuria by ELISA (Bethyl laboratories, Montgomery Tex. USA).

In Vitro Studies with GEnCs

For GEnC studies, cultured rat GEnCs (32) were grown to 75% confluence in 6 well plates (n=3 wells/condition), washed twice with warm PBS, serum free RPMI containing 200 μM H2O2, along with 600 μg/well of control stable cell line supernatant, or Angptl4-HEK293 stable cell line supernatant, or supernatant from ManNAc treated Angptl4-HEK293 cell line. Wells were sampled at 24, 36 and 48 hours. LDH release was measured using the cytotoxicity detection kit (Roche Diagnostics, Mannheim Germany). OD 492 values were expressed as a ratio of readings from wells in which no $H_2O_2$ or stable cell line supernatant was added.

Statistical Analysis

Analysis of difference in proteinuria or gene expression involving three or more groups was conducted by ANOVA with post analysis testing using GraphPad InStat software, Version 3.05. For comparison of two groups, the unpaired Students t test in Microsoft Excel 2003 was used.

4. Circulating Angiopoietin-Like-4 Links Proteinuria with Hypertriglyceridemia in Nephrotic Syndrome A molecular basis for the relationship between proteinuria and hyperlipidemia (hypertriglyceridemia and hypercholesterolemia) in nephrotic syndrome is not known. In this study, it is shown that increased plasma levels of the glycoprotein Angptl4 link proteinuria with hypertriglyceridemia in nephrotic syndrome due to membranous nephropathy (MN), focal and segmental glomerulosclerosis (FSGS), and minimal change disease (MCD). Circulating Angptl4 had a near neutral isoelectric point (pI), and was mostly secreted from skeletal muscle, adipose tissue and heart after the establishment of moderate to severe proteinuria. In MCD, additional early podocyte expression of high pI Angptl4, that induces proteinuria, and neutral pI Angptl4 were previously shown. Using adipose tissue overexpressing Angptl4 transgenic rats (aP2-Angptl4) and recombinant Angptl4, it was shown that circulating Angptl4 reduced proteinuria by binding to glomerular endothelial αvβ5 integrin, while also inducing hypertriglyceridemia by blocking lipoprotein lipase (LPL) mediated triglyceride uptake. Hypertriglyceridemia was absent in nephrotic Angptl4−/− mice. Nephrotic Angptl4 and Itgb5−/− mice, and nephrotic rats injected with an anti-135 integrin antibody had delayed recovery from peak proteinuria. Moreover, recombinant human Angptl4 with mutations at the LPL binding site could reduce proteinuria without affecting plasma triglyceride levels. In summary, circulating Angptl4 reduces proteinuria while also inducing hypertriglyceridemia, and is mostly produced from peripheral organs as a systemic response to nephrotic range proteinuria.

Background

Molecular pathways that link proteinuria with hyperlipidemia, two key hallmarks of nephrotic syndrome, are not known. Hyperlipidemia has two components, hypercholesterolemia and hypertriglyceridemial. In the past, hypercholesterolemia has been attributed to increased hepatic synthesis of lipoproteins in response to proteinuria and hypoalbuminemia (2). However, the precise molecular link between proteinuria and increased hepatic lipoprotein synthesis remains unknown. The development of hypertriglyceridemia has received much less attention. A major determinant of plasma triglyceride levels is the activity of endothelium bound lipoprotein lipase (LPL), that regulates tissue uptake of triglycerides from the circulation (3). Mice that lack LPL develop very high triglyceride levels and die soon after birth (4). Prior studies show that the activity and expression of LPL protein, but not mRNA, are reduced in nephrotic syndrome (5). The molecular basis of this reduction in LPL protein activity and expression, or its relationship to proteinuria in nephrotic syndrome has not been determined.

A recent study from our laboratory showed increased expression of Angptl4 in podocytes and in the circulation in minimal change disease (MCD) (6, 7). To study the biological role of podocyte-secreted Angptl4, two types of transgenic rat models were generated. NPHS2-Angptl4 transgenic rats, that selectively overexpress Angptl4 within the glomerulus from podocytes, develop massive albuminuria without increasing circulating Angptl4 levels. By contrast, aP2-Angptl4 transgenic rats, that selectively overproduce and secrete Angptl4 from adipose tissue, develop high circulating Angptl4 levels, but are not proteinuric. Further studies showed that podocytes secrete two distinct forms of Angptl4 in nephrotic syndrome: a high pI form that is hyposialylated, and neutral pI form that is sialylated. Treatment with the sialic acid precursor N-acetyl-D-mannosamine (ManNAc) converts high pI Angptl4 to neutral pI Angptl4 in vivo, and significantly reduces albuminuria/proteinuria. By contrast, circulating Angptl4 in normal and nephrotic rats and humans is comprised almost entirely of sialylated neutral pI Angptl4.

Angptl4 is believed to block LPL activity (8) by inactivating LPL, which reduces triglyceride update and results in hypertriglyceridemia (9). Population based sequencing studies of the human ANGPTL4 gene revealed low plasma triglyceride levels in about 3% of the European-American population that has an E40K variant (10). Subsequent studies showed that recombinant Angptl4 with the E40K variant is unable to inhibit LPL activity in vitro (11). Angptl4 in circulation tends to cleave into an N-terminal fragment (contains LPL inhibiting region and a coiled coil domain, forms oligomers) and a C-terminal fragment (contains fibrinogen-like domain, remains monomeric), and mutating the Angptl4 cleavage region between amino acids 161 and 164 improves the stability of the full length protein (11). We utilized these properties of Angptl4 to develop mutants of potential therapeutic significance.

In the present study, the biological role of circulating Angptl4 in nephrotic syndrome was investigated. We noted elevated levels of Angptl4 and triglycerides, and reduced LPL activity in MN, FSGS and MCD. In addition, Angptl4−/− mice with nephrotic syndrome did not develop hypertriglyceridemia. In rat models of nephrotic syndrome, elevated circulating Angptl4 originated primarily from skeletal muscle, adipose tissue and heart after severe proteinuria had developed. In experimental MCD, some circulating Angptl4 also originated from podocytes. Elevated circulating Angptl4, whether by transgenic expression or injection of recombinant protein, increased triglyceride levels and reduced LPL activity, but also reduced proteinuria in nephrotic rodents by binding to glomerular endothelial αvβ5 integrin. Absence of β5 integrin, or its in vivo blockage using specific antibodies, or absence of circulating Angptl4, all slowed recovery from peak proteinuria. Angptl4 is therefore the first direct molecular link between proteinuria and hypertriglyceridemia. It is likely that peripheral Angptl4 secretion is stimulated primarily to help reduce ongoing proteinuria in nephrotic syndrome, but also ends up binding to LPL and inducing hypertriglyceridemia.

Results

Figure 6J:
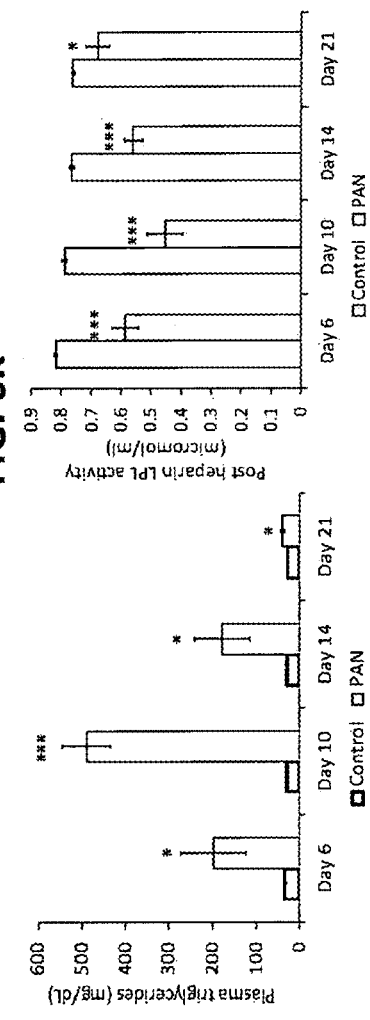
Figure 6L:
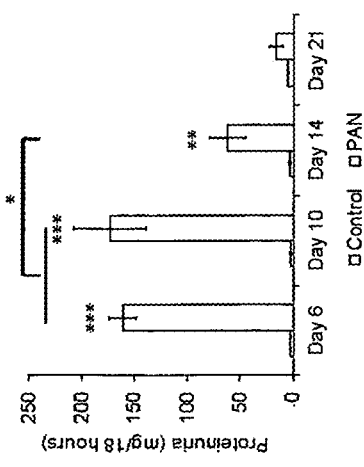
FIGS. 6L-6M show plasma triglyceride levels and LPL activity in adipose tissue specific Angptl4 overexpressing rats (aP2-Angptl4), that have elevated circulating Angptl4 levels, and 3 month old podocyte specific Angptl4 overexpressing rats (NPHS2-Angptl4), in which transgene expressed Angptl4 does not enter the circulation.
Figure 6K:
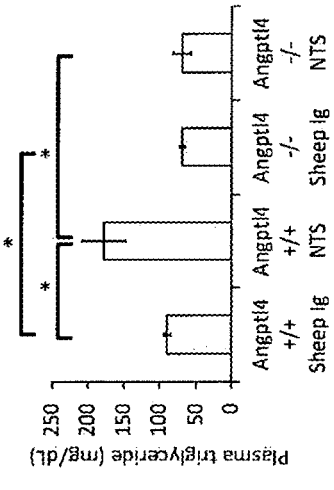
Figure 6M:
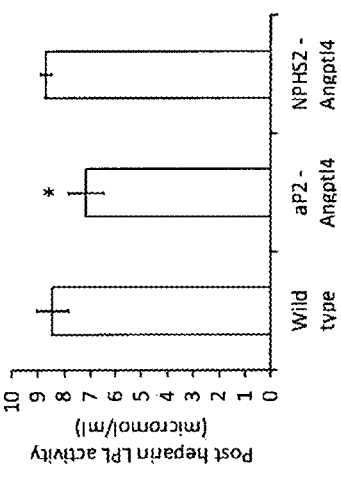
Figure 6N:
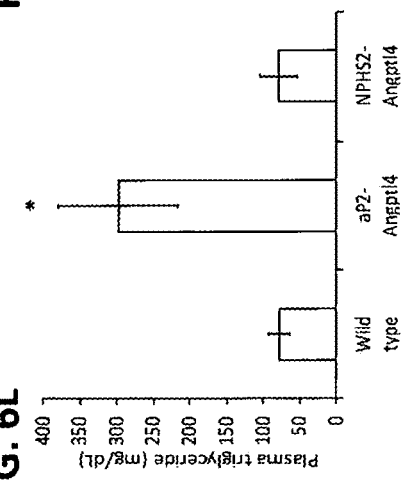
Figure 12A:
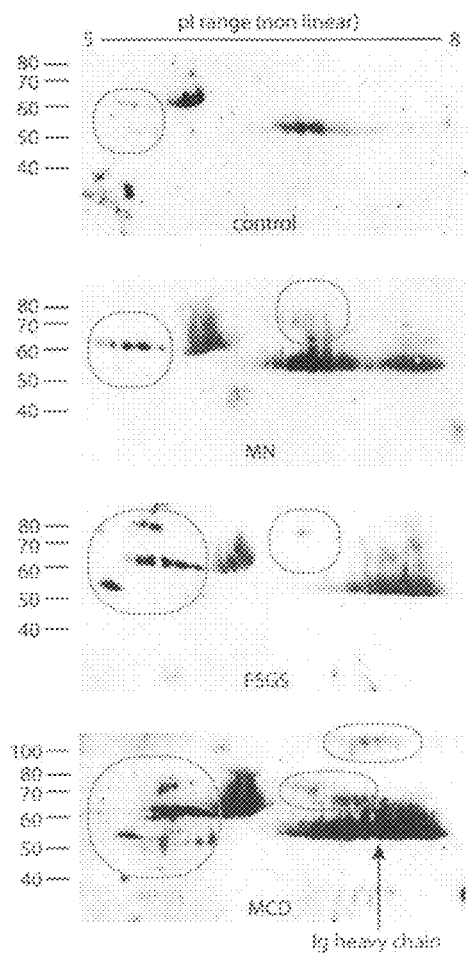
FIGS. 12A-12B show a two-dimensional gel electrophoresis of human plasma.
Figure 12B:
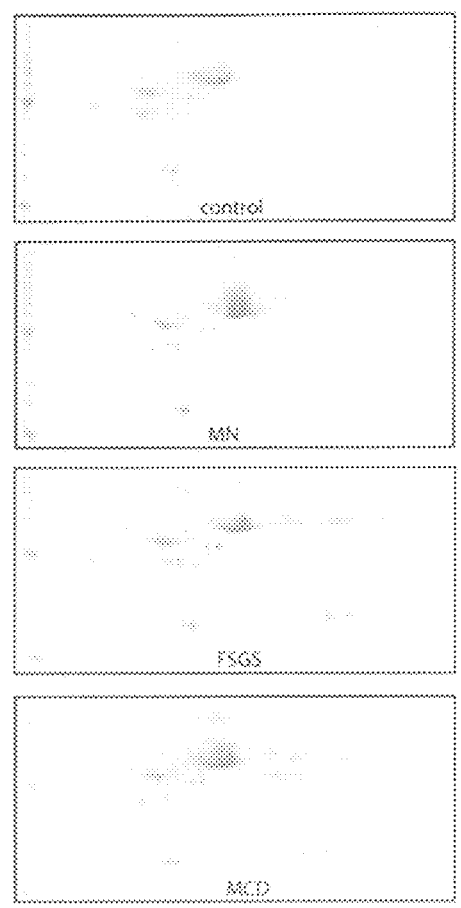
Figure 13A:
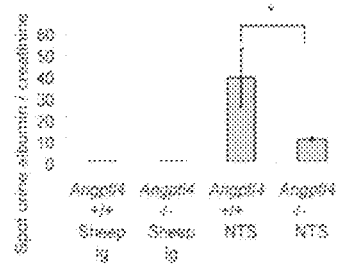
FIG. 13A shows albuminuria in Angptl4+/+ and Angptl4−/− mice 48 hours after injection of γ2-NTS, corresponds to FIG. 6N. Image is reproduced from the on line supplement of Reference 6 from Working Example 4. Similar results seen on Day 2 of study shown in FIG. 6(h)

Increased Circulating Angptl4 Levels Determine the Development of Hypertriglyceridemia in Nephrotic Syndrome:

When compared with normal healthy volunteers, significantly elevated fasting plasma Angptl4 levels were noted by ELISA in untreated patients with nephrotic syndrome due to MCD, focal and segmental glomerulosclerosis (FSGS), non-HIV collapsing glomerulopathy (CG), and membranous nephropathy (MN) (FIG. 6(a), FIG. 12). To determine whether elevated plasma Angptl4 levels can be correlated with hypertriglyceridemia and LPL activity in nephrotic syndrome, we studied plasma Angptl4, triglycerides and post-heparin LPL activity in passive Heymann nephritis (PHN, a model of MN) (12, 13), Buffalo Mna rats, that spontaneously develop FSGS (14,15), and puromycin aminonucleoside nephrosis (PAN, a model of MCD)(12) (FIG. 6(b)). Fasting plasma Angptl4 were elevated in these models after, but not before, they developed moderate to severe proteinuria. In PHN and Buffalo Mna rats, significant hypertriglyceridemia was noted when plasma Angptl4 levels were elevated and plasma LPL activity was reduced (FIG. 6(c)-(h)), In PAN, hypertriglyceridemia was present throughout proteinuria, persisted after proteinuria had normalized, and correlated well with decline in LPL activity (FIG. 6(i)-(k)). Overexpression of Angptl4 from adipose tissue in aP2-Angptl4 transgenic rats, that develop increased circulating Angptl4 levels but no proteinuria[6], also induced hypertriglyceridemia and reduced LPL activity (FIGS. 6(l) and (m)). By contrast, 3 month old NPHS2-Angptl4 transgenic rats, in which Angptl4 overexpressed from podocytes causes proteinuria but no leakage into the circulation, did not develop elevated triglyceride levels or reduced LPL activity. These overexpression studies suggest that entry of Angptl4 into the circulation is required for the development of hypertriglyceridemia. To study the relative importance of Angptl4 in the development of hypertriglyceridemia in nephrotic syndrome, severe heterologous phase complement- and leukocyte-independent proteinuria was induced in Angptl4−/− and +/+ mice using γ2-nephrotoxic serum (NTS) (FIG. 6(n)). When compared with Angptl4+/+ mice, hypertriglyceridemia was absent in Angptl4−/− mice injected with NTS, despite these mice having significant proteinuria (FIG. 13(a)). These studies show that circulating Angptl4 is a critical mediator of hypertriglyceridemia in nephrotic syndrome.

Origin of Elevated Circulating Angptl4 in Nephrotic Syndrome

Figure 7A:
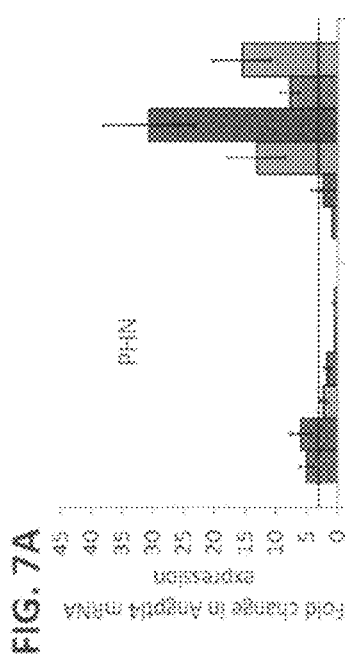
Figure 7B:
Figure 7C:
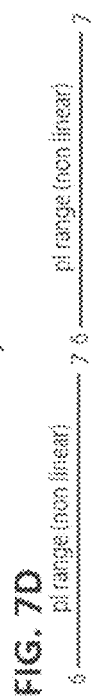
Figure 7D:
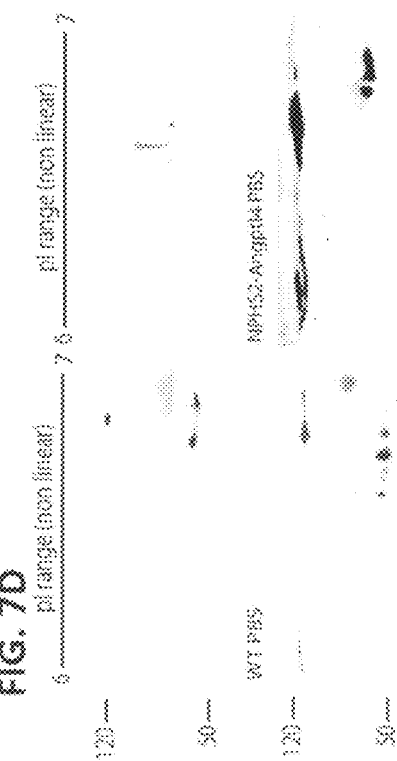
Figure 13B:
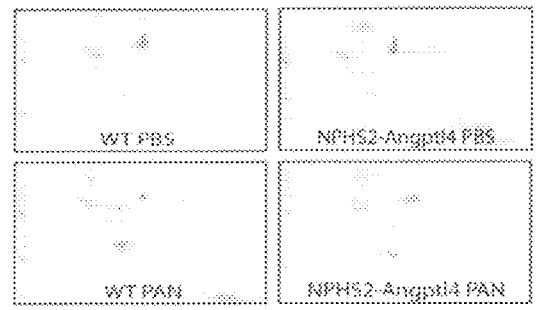
FIG. 13B shows ponceau red stained images of nitrocellulose membranes used for Western blot in FIG. 2d.

To determine the origin of increased circulating Angptl4, we conducted multi-organ Angptl4 mRNA expression profiles in rat models of nephrotic syndrome. On PHN Day 9 (FIG. 7(a)), corresponding with elevated circulating Angptl4 levels (FIG. 6(b)) and heavy proteinuria (FIG. 6(c)), prominent upregulation was noted in skeletal muscle, white adipose tissue (WAT), brown adipose tissue (BAT), and heart. Transient mild upregulation noted in glomeruli and liver earlier on Day 5 had subsided. In 4.5 month old Buffalo Mna rats (FIG. 7(b)) with elevated Angptl4 levels (FIG. 6(b)) and moderate to severe proteinuria (FIG. 6(f)), prominent upregulation was noted in the heart. Glomerular upregulation of Angptl4 is not seen in this model. In PAN, a self-limiting acute model of nephrotic syndrome, elevated circulating Angptl4 levels occur throughout disease (FIG. 6(b)). Prominent upregulation of glomerular/podocyte Angptl4 during the crescendo phase of proteinuria (Days 6 and 10) (FIG. 7(c)) was also previously described (6). This "glomerular" phase of Angptl4 upregulation (Day 6 and 10) was followed by a "peripheral" phase (Days 14 and 21) during which glomerular upregulation was absent, and prominent upregulation was noted in skeletal muscle, WAT and BAT. Since monogenic overexpression of Angptl4 from podocytes in NPHS2-Angptl4 transgenic rats does not increase circulating Angptl4 levels, 2-dimensional gel western blot studies of rat plasma were performed during the "glomerular" phase after mild PAN was induced in these rats (FIGS. 7(d), 7(e), 13(b)). Significantly higher circulating levels of Angptl4 were noted in NPHS2-Angptl4 transgenic PAN rats than wild type PAN rats. This circulating protein was reactive with the anti-V5 antibody (FIG. 7(f)), thereby confirming its podocyte origin, since the transgene expressed protein is V5-tagged at its C-terminal end. In keeping with increased circulating transgene overexpressed Angptl4, aP2-Angptl4 and NPHS2-Angptl4 transgenic rats with PAN had higher plasma triglycerides and lower LPL activity than wild type PAN rats (FIGS. 7(g) and (h)).

Urinary Loss of LPL and Angptl4 in Nephrotic Syndrome

Figure 8A:
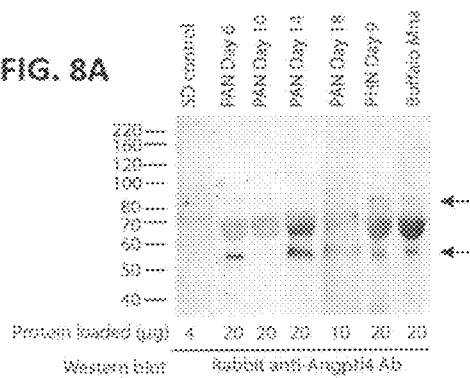
FIGS. 8A-8E show urinary loss of Angptl4 and LPL in nephrotic syndrome.
Figure 8B:
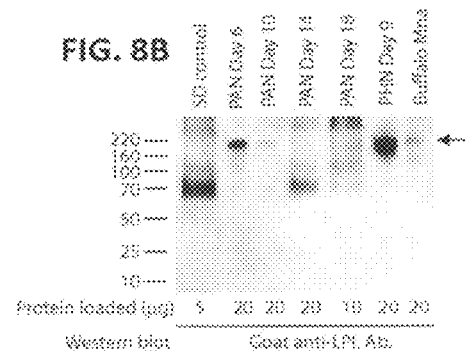
Figure 8C:
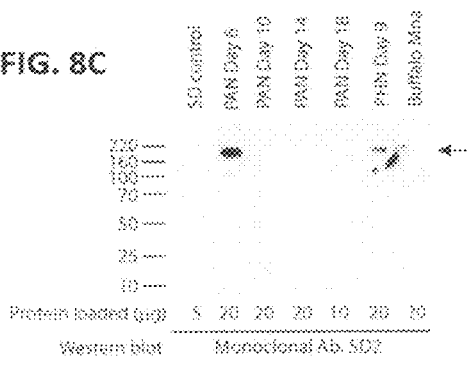
Figure 8D:
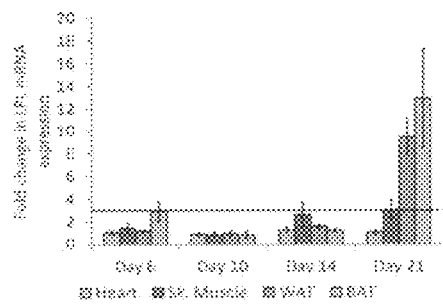
Figure 8E:
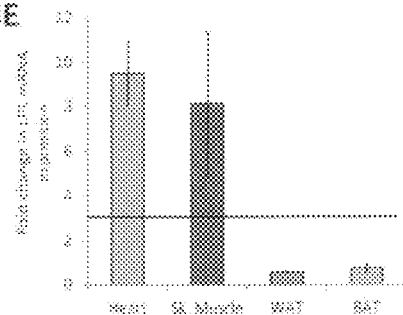
Figure 13C:
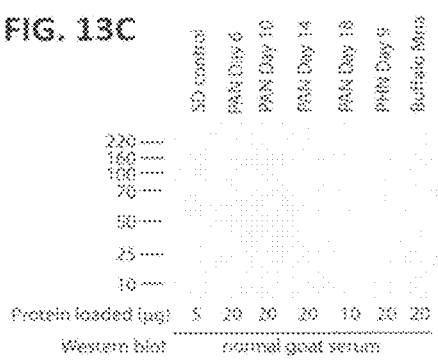
FIG. 13C shows overexposed Western blot of stripped membrane from FIG. 3b using normal goat serum.
Figure 13D:
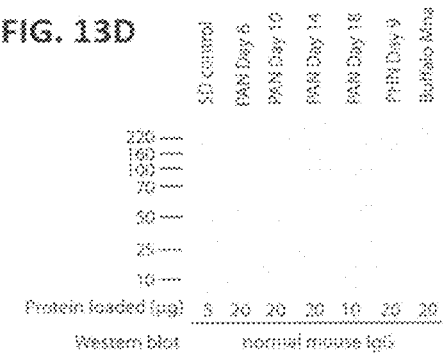
FIG. 13D shows overexposed Western blot of stripped membrane from FIG. 3c using normal mouse IgG.

Unlike normal Sprague Dawley rats, nephrotic rats lost Angptl4 in the urine (FIG. 8(a)), thereby suggesting that circulating Angptl4 levels underestimate total Angptl4 production in nephrotic states. Whereas normal rats degrade Angptl4 released LPL by hepatic uptake from the circulation (16), additional loss was noted in the urine in nephrotic syndrome (FIG. 8(b), control serum blot in FIG. 13(c)). Reactivity with 5D2 (FIG. 8(c), control serum blot in Supplementary FIG. 7(d)), a monoclonal antibody that selectively binds active LPL, suggests that active LPL is also lost in urine during heavy proteinuria. Also, nephrotic PAN rats were unable to increase LPL mRNA expression until proteinuria was greatly diminished (FIG. 8(d)). By comparison, non-proteinuric aP2-Angptl4 transgenic rats could upregulate LPL expression in skeletal muscle and heart in response to elevated Angptl4 levels (FIG. 8(e)). These factors may contribute towards the maintenance of Angptl4-mediated hypertriglyceridemia in nephrotic syndrome.

Increased Circulating Angptl4 Reduces Proteinuria

Figure 9A:
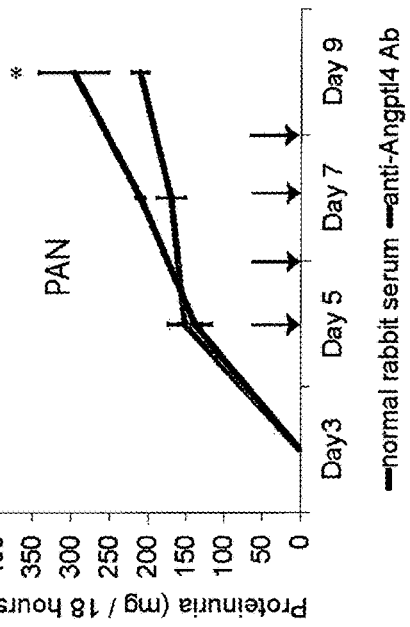
FIGS. 9A-9D show effect of circulating Angptl4 on proteinuria. Red arrows indicate time points when an antibody or recombinant protein, as appropriate, were injected.
Figure 9B:
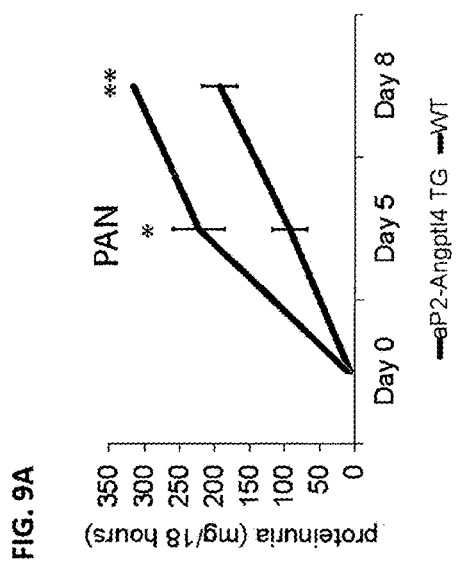
Figure 9C:
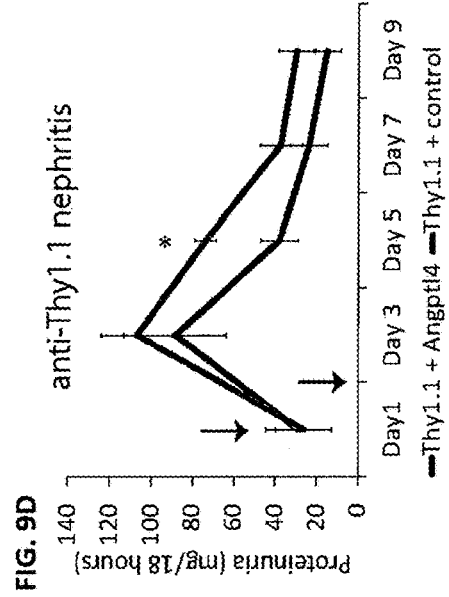
Figure 9D:
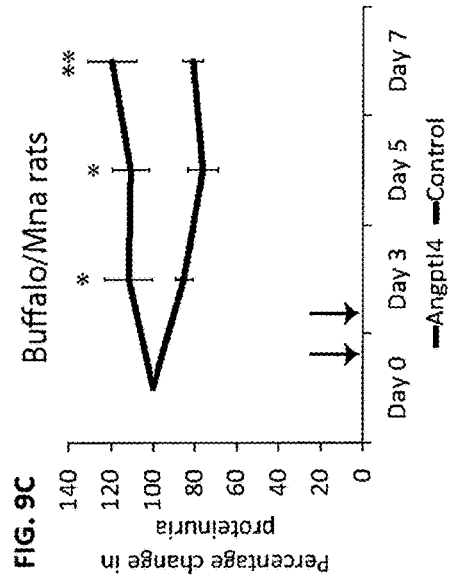

Induction of PAN in aP2-Angptl4 transgenic and wild type Sprague Dawley rats revealed significantly lower proteinuria in transgenic rats (FIG. 9(a)), suggesting that circulating Angptl4 has an anti-proteinuric effect. To test whether this anti-proteinuric effect was specifically induced by circulating Angptl4, previously characterized rabbit anti-rat Angptl4 antibodies (6) were injected into wild type PAN rats after the onset of proteinuria to partially deplete circulating Angptl4 levels, and noted increased proteinuria (FIG. 9(b)). Next, recombinant sialylated rat Angptl4 was injected intravenously into Buffalo Mna rats (FIG. 9(c)), and rats with anti-Thy1.1 nephritis, a model of mesangial injury (FIG. 9(d)). In both cases, significant reduction of proteinuria was noted.

Human Angptl4 Mutants with Reduced LPL Inactivation Reduce Proteinuria

In order to dissociate the LPL mediated effects of Angptl4 on triglyceride uptake from its effects on proteinuria, pcDNA3.1 V5 His B constructs of human Angptl4 with mutations at two sites were generated (FIG. 10(a)). One set of mutations were made at or near a site known to be important for binding to LPL (amino acids 40 or 39). Another set of mutations were made in a region known to be involved in the cleavage of full length Angptl4 (amino acids 161 to 164).

Figure 13E:
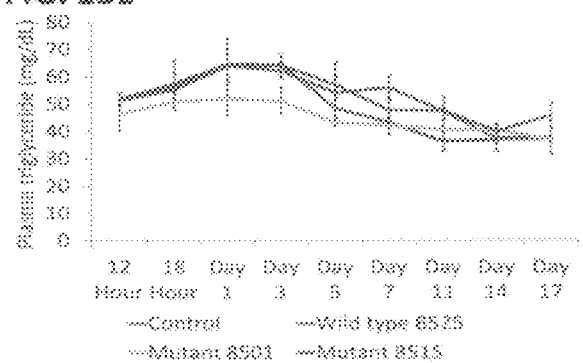
FIG. 13E shows fasting plasma triglyceride levels in Buffalo Mna rats from 12 hours to 17 days after injection of recombinant human wild type Angptl4, human mutant Angptl4, and control protein. * $P<0.05$

Next, HEK 293 based stable cell lines were developed for these mutant and wild type plasmids, and recombinant protein containing supernatant harvested in serum free conditions. To ensure adequate sialylation of Angptl4, ManNAc (N-acetyl-D-mannosamine) was added to the culture media. Wild type and recombinant Angptl4 were then assessed by Western blot using anti-V5 antibody, and migration of the mutant proteins at the appropriate size and reduced cleavage were noted (FIG. 10(b)). After single intravenous injection of equal amounts of human recombinant Angptl4 into proteinuric Buffalo Mna rats, higher peak levels were noted for the mutant proteins (FIG. 10(c)). Significant reduction of proteinuria was noted for 2 weeks after a single injection in wild type and mutant proteins (mean±SE of nadir as a percentage of baseline: wild type 8525, 53.8±6.3; mutant 8501, 35.9±12.1; mutant 8515, 41.2+7.2) (FIG. 10(d)). Plasma triglyceride levels were significantly higher compared to baseline in wild type, but not in mutant, Angptl4 injected rats at 3 and 6 hours after injection (FIG. 10(e)). Triglyceride levels were significantly lower in mutant protein than in wild type protein injected rats at 6 hours. Fasting triglyceride levels between 12 hours and Day 17 were indistinguishable between wild type and mutant Angptl4 injected rats, and were similar to controls (FIG. 13(e)).

Circulating Angptl4 Reduces Proteinuria by Binding to Glomerular Endothelial αvβ5 Integrin:

Confocal imaging of aP2-Angptl4 TG rat kidney using anti-V5 antibodies showed that adipose tissue secreted Angptl4-V5 colocalized with the glomerular endothelium (FIG. 11(a)). Using immunogold EM, this Angptl4-V5 was noted on the glomerular endothelial surface, mostly in the region of the endothelial cell-glomerular basement membrane interface (FIG. 11(b)). Using recombinant rat Angptl4 secreted from stable cell lines, we showed that sialylated Angptl4 protein, which mimics circulating Angptl4 in nephrotic states, protected cultured rat glomerular endothelial cells (GEnCs) from oxidative injury, whereas hyposialylated Angptl4, a pro-proteinuric form that comprises about half of podocyte-secreted Angptl4 in PAN and NPHS2-Angptl4 TG rats, increases the effects of oxidative injury (FIG. 11(c)).

Figure 14A:
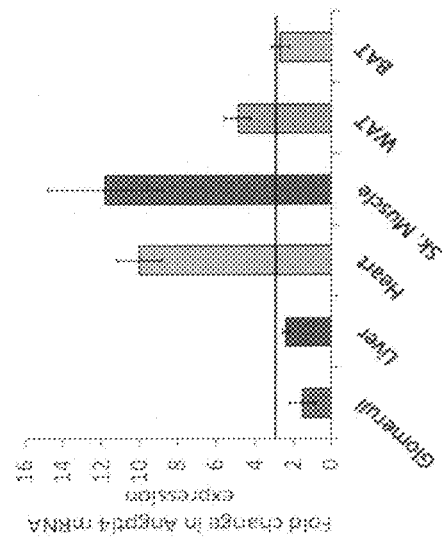
FIG. 14A shows elevated plasma Angptl4 levels during the peripheral phase of Angptl4 expression (Days 5 and 7) in γ2-NTS injected Itgb+/+ and −/− mice shown in FIG. 11E.
Figure 14B:
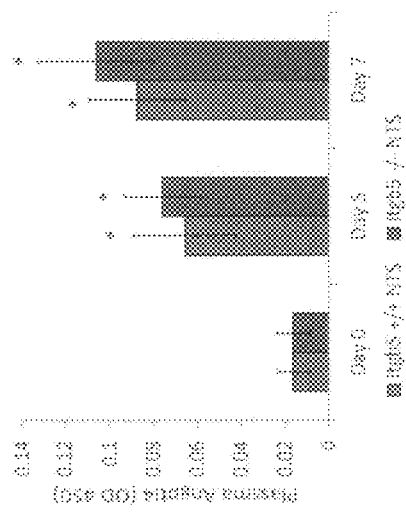
FIG. 14B shows multiorgan mRNA expression profile for Angptl4 in Itgb+/+ mice shown in FIG. 11E, 7 days after injection of γ2-NTS.
Figure 14C:
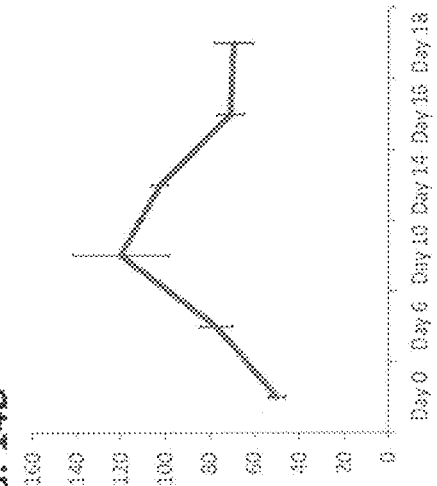
FIG. 14C shows plasma Angptl4 levels in Sprague Dawley PAN rats shown in FIG. 11F.
Figure 14D:
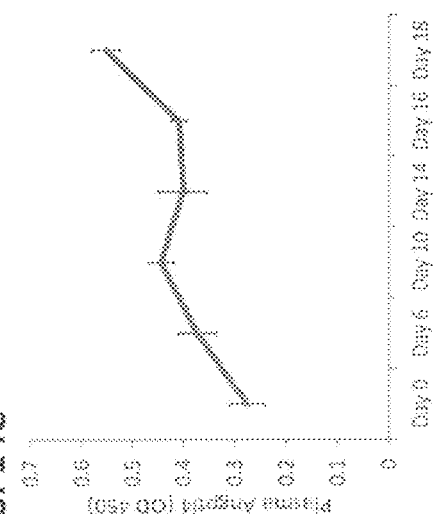
FIG. 14D shows plasma triglyceride levels in Sprague Dawley PAN rats shown in FIG. 11F. All comparisons in panels A, C and D were made with Day 0 values. * $P<0.05$

Since Angptl4 was recently shown to bind β5 integrin (17), it was determined whether the protective effects of circulating Angptl4 on proteinuria were mediated via binding to αvβ5 integrin present in glomerular endothelium. This protein:protein interaction was confirmed using recombinant rat Angptl4 and plates coated with purified human αvβ5 integrin, and noted strong dose dependent binding ($R^2$ 0.996) (FIG. 11(d)). Induction of nephrotic syndrome using □2-NTS in 135 integrin knockout (Itgb5-/-) and wild type (Itgb5+/+) mice revealed much higher levels of proteinuria in the knockout mice during the recovery phase (Days 5 and 7) (FIG. 11(e)), which corresponds with the peripheral phase of circulating Angptl4 production from skeletal muscle and adipose tissue in this model (Supplementary FIGS. 14(a) and (b)). This suggests the decline from peak proteinuria (beyond Day 3) was influenced by the presence of circulating proteins like Angptl4 that exert anti-proteinuric effects by binding αvβ5 integrin. To block the αvβ5 integrin-Angptl4 interaction, an antibody against the extracellular part of β5 integrin (anti-β5 integrin antibodies) or preimmune serum was injected into wild type (Sprague Dawley) rats (FIG. 11(f), Supplementary FIGS. 14(c) and (d)) and aP2-Angptl4 transgenic rats (FIG. 11(g)) during recovery from peak proteinuria (beyond Day 10, corresponds to peripheral phase of circulating Angptl4 production) in PAN. A significant delay in recovery was noted in both models. Finally, nephrotic syndrome was induced in Angptl4+1+ and Angptl4-/- mice and noted a significant delay in recovery from peak proteinuria (Day 7) during the peripheral phase of circulating Angptl4 production, which is absent in Angptl4−/− mice (FIG. 11(*h*)). The lower level of proteinuria in Angptl4−/− mice during the glomerular phase is consistent with our previously published description of podocyte secreted hyposialylated Angptl4 (6) as being one of several causes of proteinuria in this model.

Additional Mutants

Figure 18:
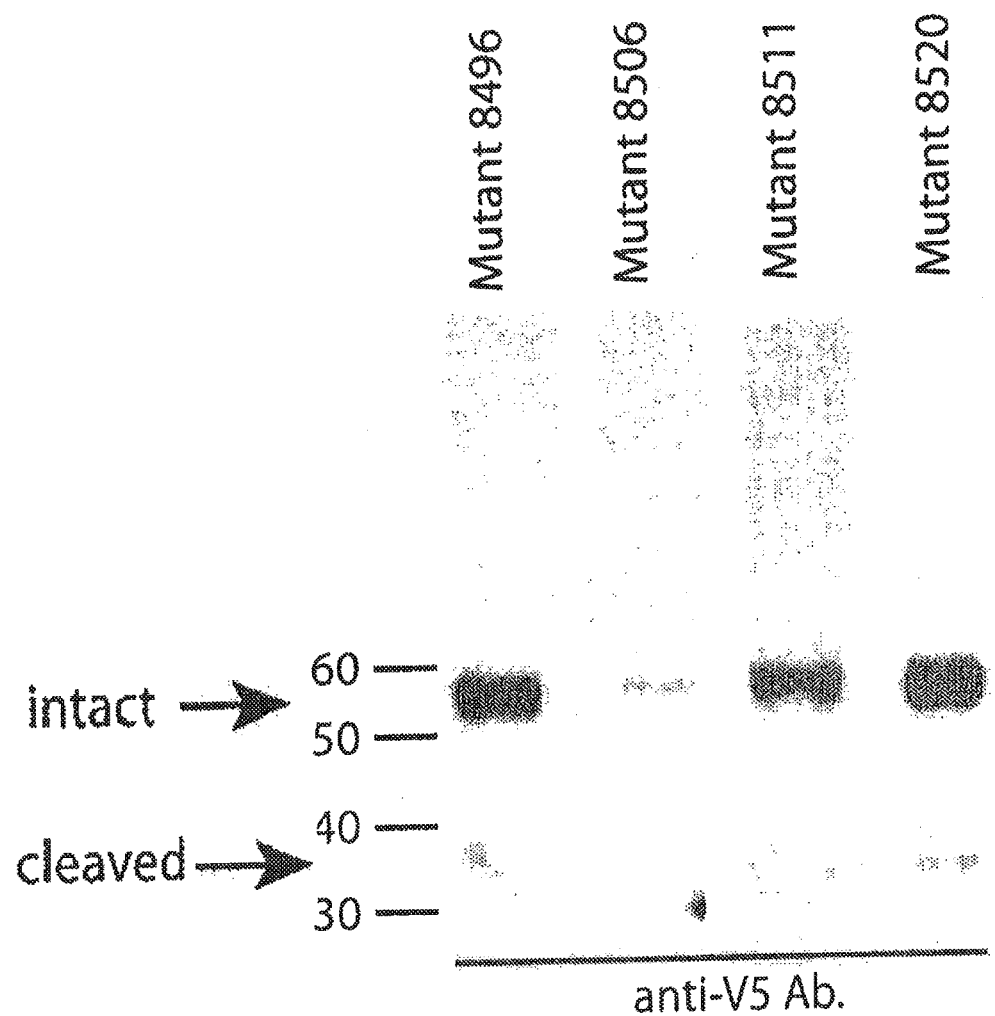
FIG. 18 shows a Western blot of recombinant proteins shown in FIG. 17 tagged using mouse anti-V5 antibody and control mouse IgG to demonstrate the expected size of the intact protein and reduced cleavage in the mutant proteins (arrows).
Figure 19:
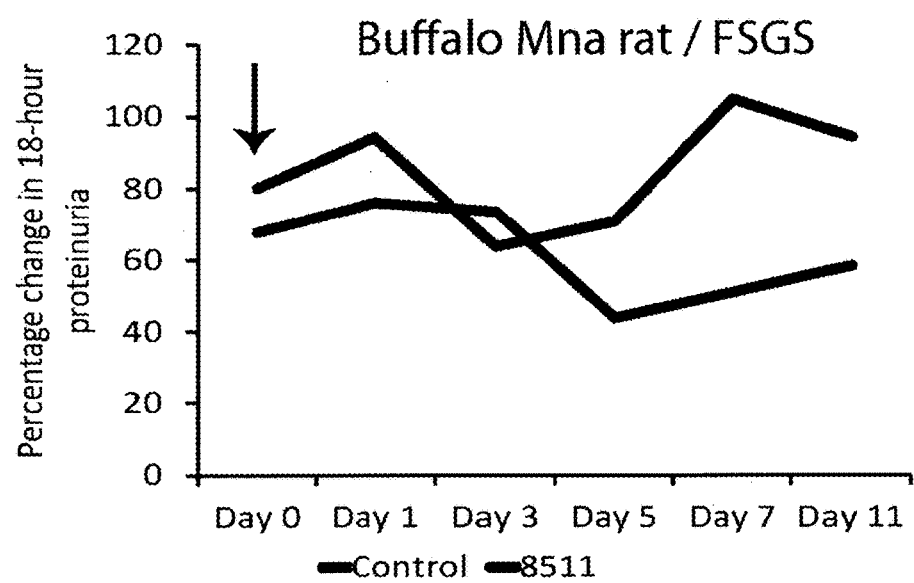
FIG. 19 shows peak levels for the mutant 8511 of change in proteinuria after a single intravenous injection into proteinuric Buffalo Mna rats.
Figure 20:
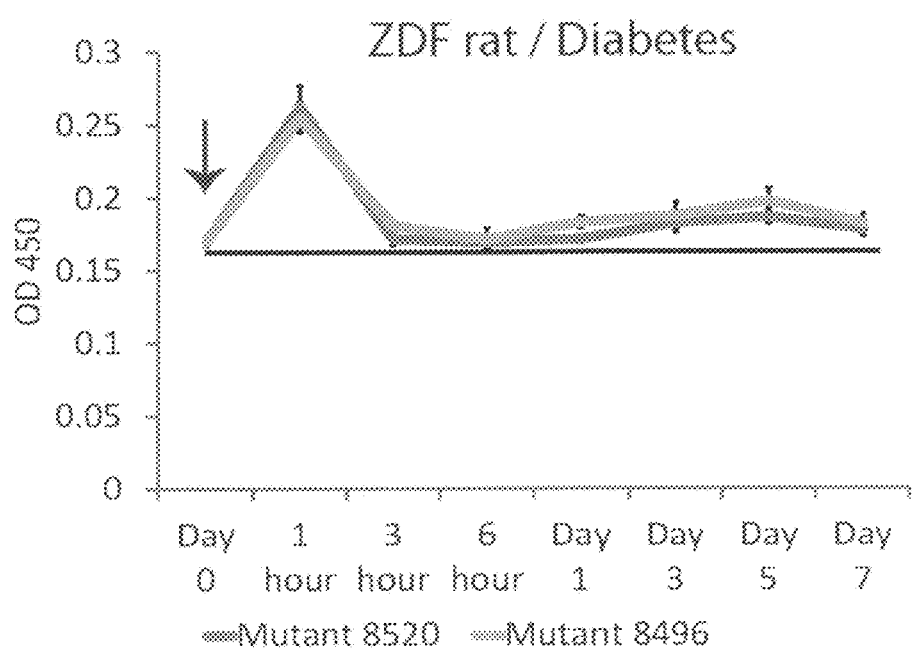
FIG. 20 shows decline in proteinuria after injection of 2 mutant human Angptl4 proteins (15 μg) into Zucker Diabetic Fatty rats, a model of diabetic nephropathy and diabetic kidney disease.
Figure 21:
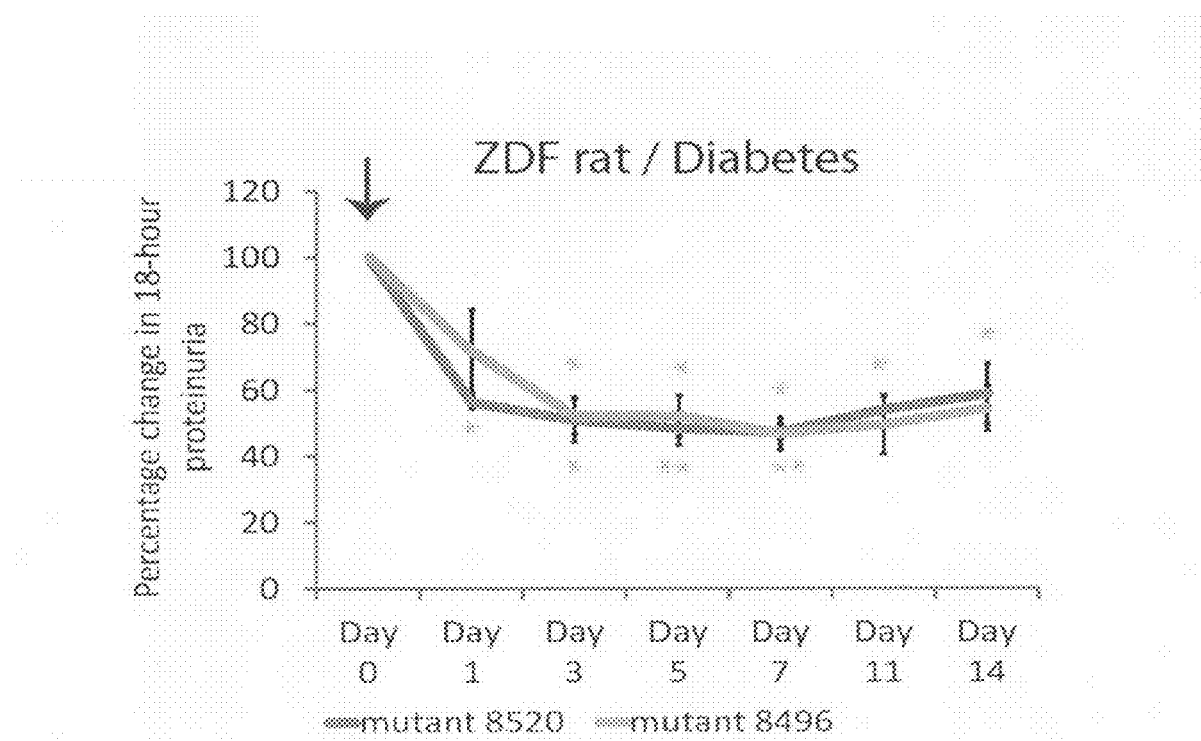
FIG. 21 shows levels of proteinuria of two mutant human Angptl4 proteins after injection (15 μg) into Zucker Diabetic Fatty rats. All * values are relative to baseline Day 0 values.
Figure 22:
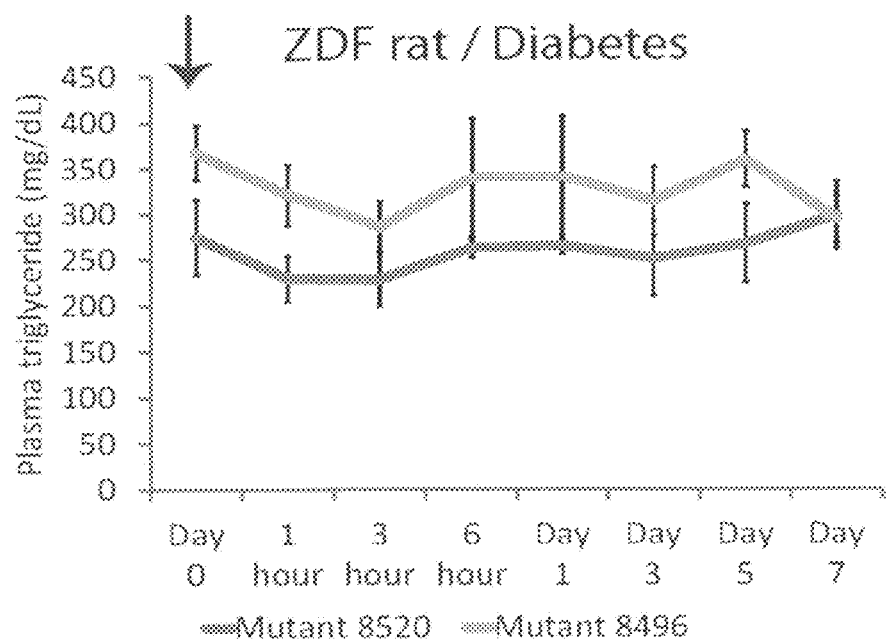
FIG. 22 shows no increase in plasma triglyceride levels after injection of 2 mutant forms of human Angptl4 protein (15 μg) in Zucker Diabetic Fatty rats. For FIGS. 20-22: * $P<0.05$, ** $P<0.01$. # $P<0.05$.

Four addition mutant proteins were studied: 8496, 8506, 8511, and 8520. Each has at least one amino acid substitution at positions 39, 40, or 161-164 as shown in FIG. 17. HEK 293 based stable cell lines were developed and cultured as described above to express mutant protein. All four mutant proteins were tagged with V5, with anti-V5 antibody, then assessed by Western blot using anti-V5 antibody, and migration of the mutant proteins at the appropriate size and reduced cleavage were noted. Results show that the amount of cleaved protein is significantly reduced in the mutants compared to the wild type via Western blot (FIG. 18). After single intravenous injection of equal amounts of mutant 8511 protein into proteinuric Buffalo Mna rats, higher peak levels were noted for the mutant 8511 (FIG. 19). Red arrows indicate single time point when recombinant protein was injected. Two mutant human Angptl4 proteins (15 μg) were injected into Zucker Diabetic Fatty rats (a model of diabetic nephropathy and diabetic kidney disease, n=4 rats/group), after which increased circulating levels of the mutant proteins (FIG. 20) were noted, along with reduction in proteinuria (FIG. 21), but without significant increase in plasma triglyceride levels (FIG. 22). * P<0.05, ** P<0.01. # P<0.05. All * values are relative to baseline Day 0 values.

Discussion

Figure 15:
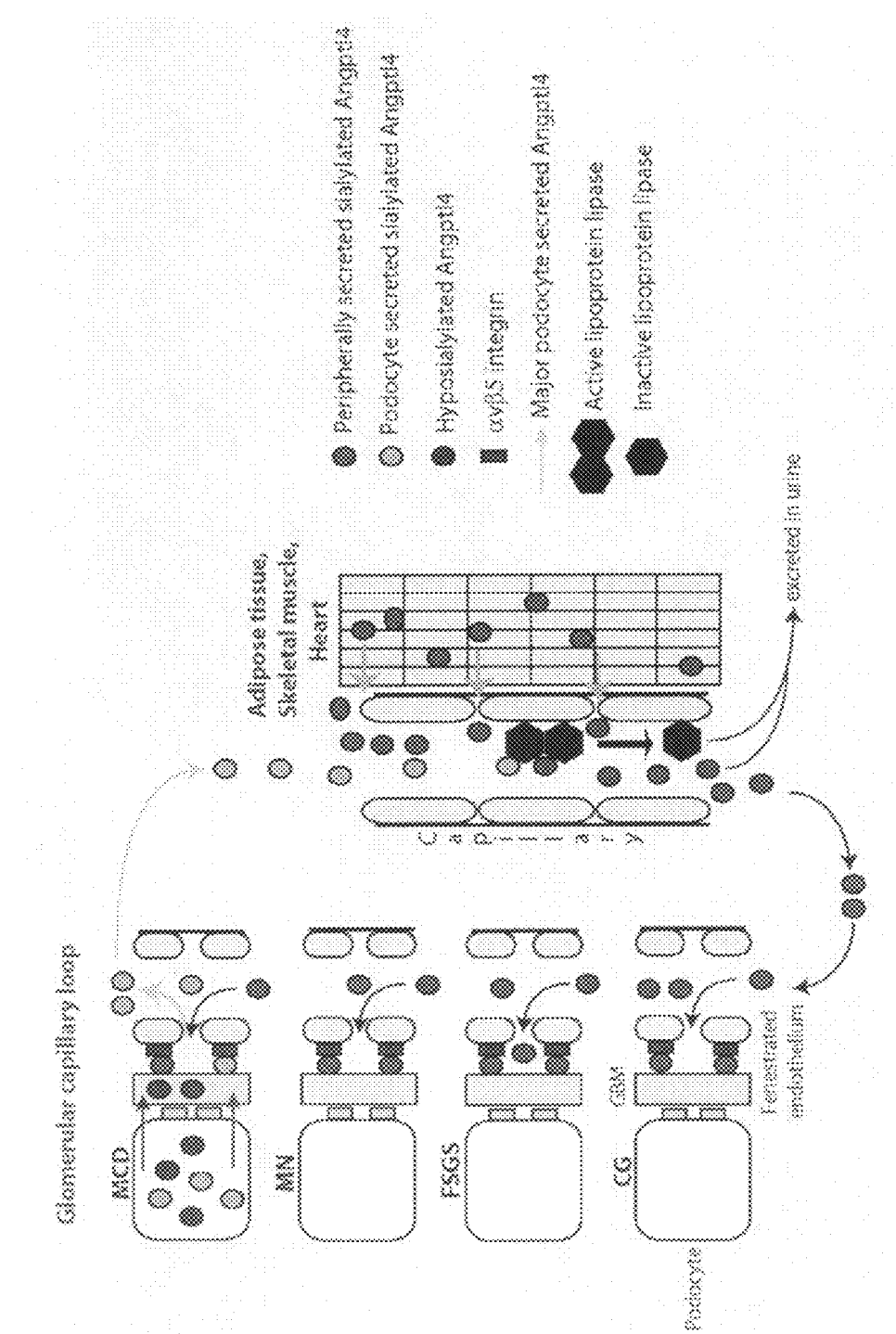
FIG. 15 shows a schematic representation of the origin and biological effects of circulating Angptl4 in nephrotic syndrome. Following the establishment of moderate to severe proteinuria, skeletal muscle, adipose tissue and heart upregulate and secrete Angptl4 into the circulation. Some of this Angptl4 binds to αvβ5 integrin on the glomerular endothelial surface and reduces proteinuria, while some binds to, and converts active lipoprotein lipase (LPL) into inactive LPL, that are lost in urine. Reduced LPL mediated triglyceride uptake results in hypertriglyceridemia. Some circulating Angptl4 is also lost in the urine. In minimal change disease (MCD), podocyte secreted hyposialylated Angptl4 exerts local pro-proteinuric effects within the glomerulus, whereas podocyte secreted sialylated protein binds the glomerular endothelium and leaks into the circulation to induce hypertriglyceridemia. In membranous nephropathy (MN), focal and segmental glomerulosclerosis (FSGS) and non-HIV collapsing glomerulopathy (CG), podocytes do not contribute significant amounts of Angptl4 to the circulation.
Figure 16A:
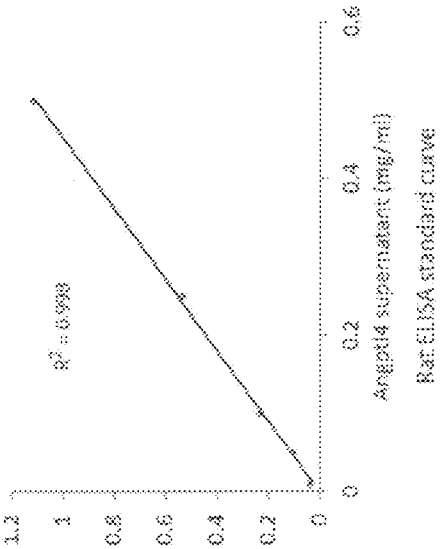
FIG. 16A shows a standard curve for human Angptl4 ELISA.
Figure 16B:
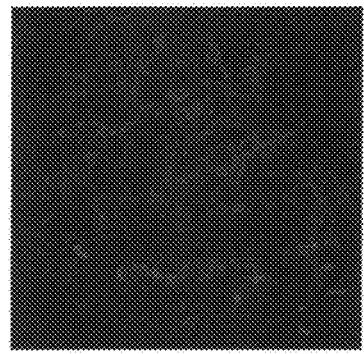
FIG. 16B shows a standard curve for rodent Angptl4 ELISA.
Figure 16C:
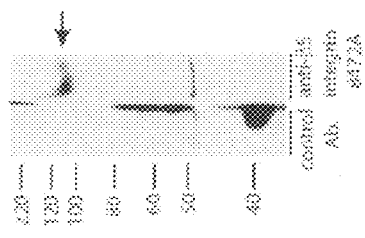
FIG. 16C shows the characterization of anti-β5 integrin antibody 8472A by Western blot.
Figure 16D:
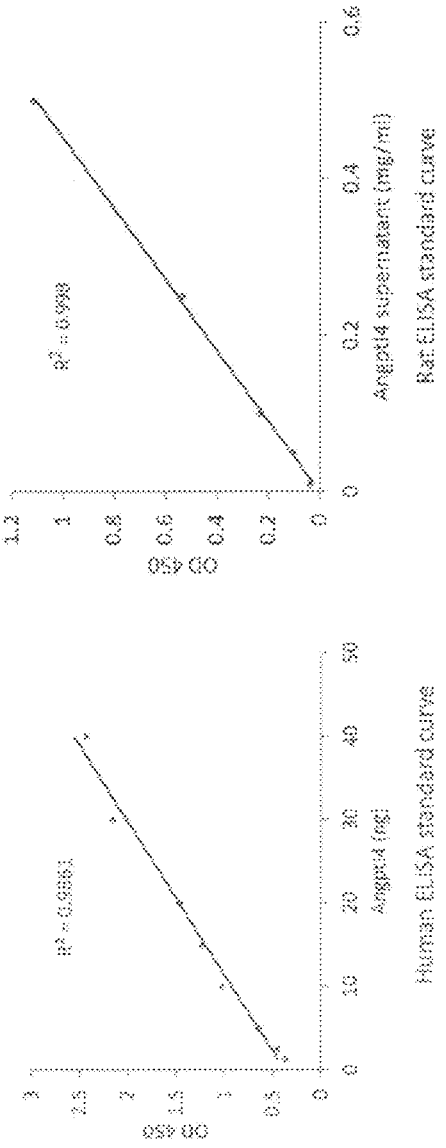
FIG. 16D shows a confocal image of a rat glomerulus that shows binding of anti-β5 integrin antibody (red, detected using donkey anti rabbit IgG) to glomerular endothelium (blue, labeled with mouse anti-PECAM1 antibody) six hours after intravenous injection, resulting in a magenta overlap pattern.

Without wishing to be bound by any given hypothetical model, this study shows that circulating Angptl4 is a key molecular mediator in nephrotic syndrome (FIG. 15). It describes, for the first time, how two key components of this syndrome, proteinuria and hypertriglyceridemia, are linked at a molecular level. The glomerulus is central to the development of proteinuria by mechanisms that vary among different diseases. Using animal models of MN and FSGS, two conditions commonly associated with sub-acute onset of proteinuria and edema, it was demonstrated that peripheral organs, especially skeletal muscle, adipose tissue and heart, respond to increasing proteinuria by upregulating Angptl4 expression. Circulating Angptl4, derived at this stage exclusively from these peripheral organs, has two potent effects. First, it binds to $\alpha v \beta 5$ integrin in the glomerular endothelium and reduces proteinuria, thereby suggesting that the primary purpose of increasing circulating Angptl4 is an attempt to reduce proteinuria. Second, and perhaps an unintended consequence of increasing circulating Angptl4 levels, is its binding to LPL (its physiological function), reduced triglyceride uptake, and hypertriglyceridemia. It is important to clarify that the link between proteinuria and hypertriglyceridemia discussed here does not relate to the primary pathogenesis of proteinuria, but to its reduction/modification by circulating Angptl4. The lag between the onset of proteinuria and the development of hypertriglyceridemia in human nephrotic syndrome is also explained by peripheral production of Angptl4, since it requires moderate to severe proteinuria (at least 3.5 grams/24 hours in humans) to develop this response. Early, mild proteinuria in these two animal models was not associated with a peripheral organ Angptl4 response, elevated plasma Angptl4 or increased triglyceride levels. Since increased Angptl4 secretion from peripheral tissues is also a physiological response to fasting (18), it is possible that increased peripheral production of Angptl4 is part of a fasting-like response being used by the body to curb excessive urinary protein loss in nephrotic syndrome.

Additional interesting lessons are learnt from PAN rats, a model of MCD, in which onset of edema and proteinuria is acute. Prior studies (6) show that podocytes in MCD produce two distinct forms of Angptl4: a high pI, hyposialylated form that induces proteinuria, and a neutral pI sialylated form identical to circulating Angptl4. Among other factors, inadequate sialic acid substrate plays a major role in the production of high pI Angptl4 by podocytes in MCD, and conversion of high pI Angptl4 to neutral pI Angptl4 in vivo using the sialic acid precursor N-acetyl-D-mannosamine reduces proteinuria. Unlike FSGS and MN, glomerular upregulation of hyposialylated Angptl4 plays a key role in the development of proteinuria in this disease. Circulating sialylated Angptl4 remains elevated throughout the duration of the PAN model, with the source being the glomerulus in the initial part (i.e. glomerular phase), and skeletal muscle and adipose tissue (i.e. peripheral phase) in the later stages. An in vitro study in this paper show that high pI Angptl4 increases, and neutral pI Angptl4 reduces endothelial injury in the setting of oxidative stress. Further studies on high pI Angptl4 are beyond the scope of this paper. All recombinant Angptl4 used for in vivo studies in this paper was the neutral pI sialylated form. As with rat models of MN and FSGS, PAN rats also develop a peripheral phase of Angptl4 upregulation that contributes significantly to the decline of proteinuria after Day 10.

A significant mediator to reduction in proteinuria in all models is the Angptl4-$\alpha v \beta 5$ integrin interaction in glomerular endothelium, since absence of $\beta 5$ integrin or Angptl4 in knockout mice, or blockage of this interaction using antibodies directed against the extracellular part of $\beta 5$ integrin reduces the rate of decline of proteinuria. Another effect of the peripheral phase of Angptl4 production in PAN is the persistence of mild hypertriglyceridemia (Day 21) even after proteinuria has subsided. Similar residual hypertriglyceridemia has been previously documented in children with MCD after they go into remission (19). It is possible that circulating Angptl4 may interact with other glomerular cell surface molecules as well to exert its protective effects. There were two reasons for pursuing binding of Angptl4 to glomerular endothelial $\alpha v \beta 5$ integrin. First, confocal imaging and immunogold electron microscopy showed that Angptl4-V5 secreted from adipose tissue in aP2-Angptl4 transgenic rats binds specifically to endothelial cells in the glomerulus. Second, $\alpha v \beta 5$ is the only integrin expressed on glomerular endothelial cells in vivo shown to interact with Angptl4. The other major glomerular endothelial integrin, $\alpha v \beta 3$, does not interact with Angptl4 (17) (confirmed by us, data not shown). The precise mechanism by which Angptl4 binding to endothelial $\alpha v \beta 5$ integrin reduces proteinuria will be explored in the future. It is possible that putative endothelial-podocyte feedback loops are affected.

Another interesting observation is that entry of Angptl4 into the circulation after monogenic overexpression is organ dependent. Similar to a heart specific Angptl4 overexpressing transgenic mouse developed in the past (20), monogenic over expression of Angptl4 in podocytes in NPHS2-Angptl4 rats does not automatically allow entry into the circulation. By contrast, overexpression in adipose tissue (aP2-Angptl4 transgenic rats (6), aP2-Angptl4 transgenic mice (18)) reliably increases circulating Angptl4 levels. The entry of podocyte secreted Angptl4 into the circulation, as noted in the Sprague Dawley rat PAN glomerular phase and in NPHS2-Angptl4 transgenic rats with PAN, likely requires the activity of other as yet unidentified proteins produced in the glomerulus. This also fits in well with human glomerular disease, in which expression of multiple genes and proteins is simultaneously affected. Therefore, the systemic availability and effects of circulating Angptl4 is likely to be affected by other genes/proteins altered in multiple organs as part of the disease process, and also by urinary loss of Angptl4 and LPL in the nephrotic state.

The anti-proteinuric effects of circulating Angptl4 may already play a partial role in the efficacy of glucocorticoids used to treat many different forms of glomerular disease. The effects of glucocorticoids on Angptl4 expression are organ dependent. Whereas they reduce Angptl4 expression in podocytes in MCD (6), they have been shown to increase adipose tissue expression of Angptl4 in mice (21). Future studies could explore whether glucocorticoids induce secretion of sufficient amounts of Angptl4 from adipose tissue into the circulation, whether this effect is dose dependent in vivo, and whether this also happens in nephrotic syndrome.

Other soluble proteins have been implicated in the pathogenesis of human glomerular disease. Vascular endothelial growth factor, secreted from podocytes and also present in the circulation, is shown to be involved in the development of human thrombotic microangiopathy, and exerts its biological effects via specific receptors expressed on the endothelial and podocyte surface (22). Soluble fms-like tyrosine kinase 1 (23) and soluble endoglin (24), secreted in excessive amounts from the placenta in pre-ecclampsia, are involved in the pathogenesis of glomeruloendotheliosis. These proteins, however, are implicated in disease pathogenesis and are not a systemic response to disease. The soluble urokinase receptor suPAR was recently shown to have pro-proteinuric effects exerted primarily by binding to podocyte $\alpha v \beta 3$ integrin (25). A common denominator between anti-proteinuric Angptl4 and pro-proteinuric suPAR is the interaction of both circulating proteins with glomerular integrins. A follow up study by the same group shows that suPAR levels are also increased in FSGS patients with mutations in the NPHS2 gene (26). This would suggest that in these patients with NPHS2 mutations, the elevation of suPAR is a systemic response to glomerular disease. In such cases, SuPAR joins a class of circulating proteins exemplified by Angptl4 that are increased in response to glomerular injury or proteinuria, and have potent effects that influence the course of the underlying glomerular disease. This list will grow in the near future once putative circulating proteins that influence the pathogenesis of non-HIV collapsing glomerulopathy (27, 28) are identified.

Lastly, mutant forms of human Angptl4 are able to reduce proteinuria very significantly (mean peak reduction around 60%) without significantly affecting plasma triglyceride levels, and are effective for at least two weeks after a single intravenous injection. These recombinant proteins hold promise for further development as therapeutic agents for human glomerular disease. In summary, circulating Angptl4 is an important biological mediator of nephrotic syndrome, and represents a critical link between proteinuria and hypertriglyceridemia.

Methods for Working Example 4

ELISA for Human and Rodent Angptl4

A sandwich ELISA to measure human Angptl4 from patient and control plasma samples was purchased from R&D Systems (Minneapolis Minn., USA). The standard curve was calibrated between 1.25 ng/ml and 40 ng/ml, and had a $R^2$ value of 0.98. (Supplementary FIG. 16($a$))

To measure rat and mouse Angptl4 in plasma, a new ELISA assay was developed. A sheep anti-rat Angptl4 antibody (5006B) was raised against amino acids 22 to 101, and characterized for specificity by Western blot using a previously published rabbit anti-rat Angptl4 antibody (6) as positive control. Activity was also absorbed out using recombinant Angptl4 and loss of reactivity by Western blot and immunofluorescence was documented. The assay was standardized using concentrated supernatant from a previously published HEK293 based stable cell line that secretes recombinant rat Angptl4. Wells were coated with between 0.1 and 0.5 mg of concentrated supernatant. After blocking and washes, 10 µg of sheep anti-rat Angptl4 antibody was added, followed by washes, 16 ng/well of donkey anti sheep Ig HRP (Jackson laboratories), washes, and TMB system reagents, and measurement at OD 450 nm on an ELISA plate reader. A standard curve with a linear relationship with a $R^2$ of 0.998 was obtained (FIG. 16($b$)). For analysis of rodent plasma, wells were coated with 50 µl of plasma in duplicate, followed by steps as detailed above. Readings from blank control wells, that contained all reagents minus the study sample, were obtained and subtracted from readings of the study samples. A minimum of 4 samples were measured for each time point.

Human plasma samples used for ELISA assay were obtained from IRB approved studies conducted at UAB (PI Chugh), Instituto Nacional De Cardiologia, Mexico City (PI Avila-Casado), and from previously published studies (6).

Animal Studies

The generation and characterization of NPHS2-Angptl4 and aP2-Angptl4 transgenic rats was previously published (6). Buffalo Mna rats were obtained via MTA from Dr. Masao Mitsuyama at Kyoto University, Kyoto Japan. Unless otherwise stated, all comparisons for Buffalo Mna rats were made with age and sex matched Sprague Dawley and Wistar rats. Since results were similar, only data from comparisons with Sprague Dawley rats is presented. Itgb5–/– and control 129S1/SvlmJ mice were purchased from Jackson Laboratories (Bar Harbor Me. USA). Angptl4–/– mice were provided to Sander Kersten by Eli Lilly Corporation. All studies with Angptl4–/– mice were approved by the Animal Ethics Committee at Wageningen University. All other animal studies were approved by the Institutional Animal Care and Use Committee at the University of Alabama at Birmingham.

Induction of single intravenous dose PAN (n=4 rats/group), PHN (n=4 rats/group) and anti-Thy1.1 nephritis (n=4 rats/group) was previously described (12, 13). For full dose PAN, puromycin aminonucleoside (Sigma Chemical Company, St. Louis Mo. USA) 15 mg/100 gram was used. For mild PAN, dose was reduced to 7.5 mg/100 grams. Induction of complement- and leukocyte-independent nephrotic syndrome (n=4 mice/group) using the γ2 fraction of sheep anti-rat nephrotoxic serum (NTS, kind gift from David Salant, Boston Medical Center) was previously described (29). For animal studies in which rabbit anti-rat Angptl4 antibody (6) as injected into PAN rats (n=3 rats/group), 500 µl of antibody or preimmune serum was injected in each dose. Depletion of circulating Angptl4 by the antibody was confirmed by western blot. The volume of anti-135 integrin antibodies or pre-immune serum injected per dose in rat PAN studies was as follows: Sprague Dawley rat PAN (250 µl); aP2-Angptl4 transgenic rat PAN (500 µl).

For multiorgan gene expression studies, organ samples were snap frozen in liquid nitrogen immediately after euthanasia (3 rats or mice/organ sample, pooled). White adipose tissue was obtained from the abdomen, brown adipose tissue from the interscapular area, skeletal muscle from the thigh, liver frozen intact or samples from both left and right lobe, heart frozen intact, and rat kidneys frozen and used subsequently for glomerular isolation. In mouse experiments, kidneys were perfused through the heart immediately after euthanasia using dynabeads, and then used for glomerular isolation. Twelve cDNA templates were generated from each pooled organ, and gene expression assessed by Taqman real time PCR.

Injection of Recombinant Rat and Human Angptl4

Harvesting of sialylated rat Angptl4 from a HEK293 cell based stable cell line was previously described (6). Concentrated HEK293 Angptl4 or empty pcDNA 3.1 V5 His vector stable cell line supernatant (1.8 mg, derived from approximately 200 ml of media) containing rat Angptl4 was injected per dose in the Buffalo Mna rat (n=4 rats/group) and the Thy1.1 rat (n=4 rats/group) studies. For studies in which recombinant human wild type Angptl4, mutant Angptl4 and control protein were injected into Buffalo Mna rats (n=3 rats/group), 55 μg of recombinant protein (quantified by ELISA) in concentrated supernatant, or equal amounts of control stable cell line supernatant (equalized by protein assay) was used per dose.

Post Heparin LPL Activity

Rats were injected intravenously with 10 units/100 g weight of porcine heparin 15 minutes prior to euthanasia, and activity measured using an assay from Roar Biomedical, Inc (New York N.Y. USA) (30). Serum triglycerides were measured in the fasting state using an autoanalyzer (some studies) or a kit from Cayman Chemical Company (Ann Arbor Mich. USA).

The following techniques have been previously described: 18 hour urine collection in metabolic cages, measurement of proteinuria, mouse urine albumin and creatinine, 2D gel electrophoresis and Western blot, confocal imaging, immunogold electron microscopy, extraction of total RNA, generation of cDNA templates (2 μg total RNA/template), real time PCR (6, 12, 13, 31). In real time PCR studies, a three-fold change is mRNA expression was taken as significant and has been validated by us in prior publications (13, 31). Western blot for LPL was conducted using goat anti-LPL antibody (Santa Cruz Biotechnology, Santa Cruz Calif. USA), and a 5D2 monoclonal antibody (gift from John Brunzell, University of Washington) that specifically identifies active dimeric LPL (32). Densitometry of 2D gel Western blots was conducted using Image Quant TL 7.0 software (GE Healthcare, Waukesha Wis. USA). Mouse anti-PECAM1 antibody was purchased from BD Pharmingen (San Diego Calif. USA). All secondary antibodies used were purchased from Jackson ImmunoResearch laboratories (West Grove Pa. USA), and had minimal background reactivity to non-target species.

Development of Human Angptl4 Mutant Constructs and Stable Cell Lines

A human Angptl4 clone was mutated using PCR based mutagenesis. Wild type and mutant human Angptl4 clones in pcDNA 3.1 V5 His vector were used to develop HEK 293 based stable cell lines as previously described (6). When used for harvesting protein, the serum free DMEM included 25 mM N-acetyl-D-mannosamine (ManNAc), a precursor of sialic acid, to ensure adequate sialylation of recombinant proteins secreted into the media. Proteins were harvested and supernatant concentrated as previously described (6). Recombinant human Angptl4 was quantified using ELISA.

Endothelial Cell Study

Cultured rat GEnCs grown in serum free conditions for 24 hours were subjected to $H_2O_2$ (200 NM) induced stress, and co-incubated with equal amounts of concentrated supernatant from Angptl4-HEK293 or control-HEK293 stable cell lines. LDH levels were measured at 24, 48, and 72 hours in the supernatant as a measure of cell injury using a cytotoxicity kit (Roche Applied Science Indianapolis Ind. USA).

αvβ5 Integrin Plate Assay 96 well plates were coated with 5 ng human purified αvβ5 integrin/well, blocked with TBST with 1% BSA, followed by incubation with increasing amounts of concentrated supernatant from stable cell lines that secrete rat Angptl4-V5. The V5 tag was detected using an anti-V5 HRP antibody (Life Technologies, Grand Island N.Y. USA, 1:2500), the reaction developed using the TMB peroxidase substrate and solution (KPL, Inc., Gaithersburg Md. USA), and read on a Labsystems Multiscan MCC340 (Thermo Fisher Scientific, Waltham Mass. USA) at 450 nm.

Generation and Characterization of Anti-β5 Integrin Antibodies

Fusion proteins were generated against parts of the extracellular segment of human β5 integrin to generate two polyclonal antibodies in rabbits (antibody 8472A, amino acids 35-460, includes integrin beta domain; antibody 8472B, amino acids 461 to 719, includes integrin beta tail). Both antibodies were tested for specificity by Western blot before and after absorbing out reactivity to recombinant human β5 integrin. Pilot studies were conducted by inducing PAN in Sprague Dawley rats (n=3 rats/group), and injecting two doses each antibody intravenously during the recovery phase to assess for in vivo blockage of β5 integrin (i. e. slower recovery of proteinuria). Since the efficacy of 8472A was several times higher than 8472B, 8472A (FIG. 16(c)) was used for further studies (n=4 rats/group). Injection of this antibody intravenously, followed by confocal imaging of glomeruli, showed localization to the endothelium in glomeruli (FIG. 16(d)).

Statistical Analysis

Analysis of difference between two groups was conducted using the unpaired Students t-test in Microsoft Excel 2010. For three or more groups, ANOVA with post analysis testing using GraphPad InStat software, Version 3.10 was used.

REFERENCES (EXCEPT FOR WORKING EXAMPLE 4)

1. Falk R, Jennette C, Nachman P H. Primary glomerular disease. In The Kidney, Brenner B M, editor, 6th edition, 1263-1349 (2000).
2. Gutman, A. & Shafrir, E. Adipose tissue in experimental nephrotic syndrome. *Am. J. Physiol.* 205, 702-706 (1963).
3. Vaziri, N. D. Molecular mechanisms of lipid disorders in nephrotic syndrome. *Kidney Int.* 63, 1964-1976 (2003).
4. Shearer, G. C. & Kaysen G A. Endothelial bound lipoprotein lipase (LpL) depletion in hypoalbuminemia results from decreased endothelial binding, not decreased secretion. *Kidney Int.* 70, 647-653 (2006).
5. Reaven, E. P., Kolterman, O. G. & Reaven, G. M. Ultrastructural and physiological evidence for corticosteroid-induced alterations in hepatic production of very low density lipoprotein particles. *J. Lipid Res.* 15, 74-83 (1974).
6. Tsukamoto, Y., Kokubo, T., Horii, A., Moriya, R. & Kobayashi, Y. Lipoprotein derangement during steroid treatment in minimal-change nephrotic syndrome. *Nephron* 73, 606-612 (1996).
7. Liu, G., Clement, L., Kanwar, Y. S., Avila-Casado, C. & Chugh, S. S. ZHX proteins regulate podocyte gene expression during the development of nephrotic syndrome. *J. Biol. Chem.* 281, 39681-39692 (2006).
8. Yoon, J. C. et al. Peroxisome proliferator-activated receptor gamma target gene encoding a novel angiopoietin-related protein associated with adipose differentiation. *Mol. Cell. Biol.* 20, 5343-5349 (2000).
9. Kersten, S. et al. Characterization of the fasting-induced adipose factor FIAF, a novel peroxisome proliferator-activated receptor target gene. *J. Biol. Chem.* 275, 28488-28493 (2000).
10. Kim, I. et al. Hepatic expression, synthesis and secretion of a novel fibrinogen/angiopoietin-related protein that prevents endothelial-cell apoptosis. *Biochem. J.* 346, 603-610 (2000).
11. Yoshida, K., Shimizugawa, T., Ono, M. & Furukawa, H. Angiopoietin-like protein 4 is a potent hyperlipidemia-inducing factor in mice and inhibitor of lipoprotein lipase. *J. Lipid Res.* 43, 1770-1772 (2002).
12. Ge, H. et al. Oligomerization and regulated proteolytic processing of angiopoietin-like protein 4. *J. Biol. Chem.* 279, 2038-2045 (2004).
13. Ge, H., Yang, G., Yu, X., Pourbahrami, T. & Li, C. Oligomerization state-dependent hyperlipidemic effect of angiopoietin-like protein 4. *J. Lipid Res.* 45, 2071-2079 (2004).
14. Romeo, S., et al. Population-based resequencing of ANGPTL4 uncovers variations that reduce triglycerides and increase HDL. *Nat. Genet.* 39, 513-516 (2007).
15. Romeo, S. et al. Rare loss-of-function mutations in ANGPTL family members contribute to plasma triglyceride levels in humans. *J. Clin. Invest.* 119:70-79 (2009).
16. Eremina, V., et al. VEGF inhibition and renal thrombotic microangiopathy. *N. Engl. J. Med.* 358, 1129-1136 (2008).
17. Davis, B., et al. Podocyte-specific expression of angiopoietin-2 causes proteinuria and apoptosis of glomerular endothelia. *J. Am. Soc. Nephrol.* 18, 2320-2329 (2007).
18. Avila-Casado, C., et al. Proteinuria in rats induced by serum from patients with collapsing glomerulopathy. *Kidney Int.* 66, 133-143 (2004).
19. Mandard, S., et al. The fasting-induced adipose factor/angiopoietin-like protein 4 is physically associated with lipoproteins and governs plasma lipid levels and adiposity. *J. Biol. Chem.* 281:934-944 (2006).
20. Clement, L., et al. Early changes in gene expression that influence the course of primary glomerular disease. *Kidney Int.* 72, 337-347 (2007).
21. Cazes, A. et al. Extracellular matrix-bound angiopoietin-like 4 inhibits endothelial cell adhesion, migration, and sprouting and alters actin cytoskeleton. *Circ. Res.* 99, 1207-1215 (2006).
22. Malicdan, M. C., Noguchi, S., Hayashi, Y. K., Nonaka, I. & Nishino, I. Prophylactic treatment with sialic acid metabolites precludes the development of the myopathic phenotype in the DMRV-hIBM mouse model. *Nat. Med.* 15, 690-695 (2009).
23. Galeano, B. et al. Mutation in the key enzyme of sialic acid biosynthesis causes severe glomerular proteinuria and is rescued by N-acetylmannosamine. *J. Clin. Invest.* 117, 1585-1594 (2007).
24. Ruge, T. et al. Lipoprotein lipase in the kidney: activity varies widely among animal species. *Am. J. Physiol. Renal Physiol.* 287, F1131-F1139 (2004).
25. Koliwad, S. K. et al. Angiopoietin-like 4 (ANGPTL4/FIAF) is a direct glucocorticoid receptor target and participates in glucocorticoid-regulated triglyceride metabolism. *J. Biol. Chem.* 284, 25593-25601 (2009).
26. Liu, G. at al. Neph1 and nephrin interaction in the slit diaphragm is an important determinant of glomerular permeability. *J. Clin. Invest.* 112, 209-221 (2003).
27. Dijkman, H. B. P. M., Mentzel, S., de Jong, A. S. & Assmann, K. J. M. RNA in situ hybridization using digoxigenin-labeled cRNA probes. *Biochemica* 2, 23-27 (1995).
28. Isogai, S., Mogami, K., Shiina N. & Yoshino, G. Initial ultrastructural changes in pore size and anionic sites of the glomerular basement membrane in streptozotocin-induced diabetic rats and their prevention by insulin treatment. *Nephron.* 83, 53-58 (1999).
29. Bakker, W. W. et al. Altered activity of plasma hemopexin in patients with minimal change disease in relapse. *Pediatr. Nephrol.* 20, 1410-1415 (2005).
30. Graves, R. A., Tontonoz, P., Platt, K. A., Ross, S. R. & Spiegelman, B. M. Identification of a fat cell enhancer: analysis of requirements for adipose tissue-specific gene expression. *J. Cell Biochem.* 49, 219-224 (1992).
31. Yoshida, K., Ono, M., Koishi, R. & Furukawa, H. Characterization of the 5' regulatory region of the mouse angiopoietin-like protein 4. *Vet. Res. Commun.* 28, 299-305 (2004).
32. Zeng, L. et al. HMG CoA reductase inhibition modulates VEGF-induced endothelial cell hyperpermeability by preventing RhoA activation and myosin regulatory light chain phosphorylation. *FASEB J.* 19, 1845-1847 (2005).
33. Romeo, S. et al. Population-based resequencing of ANGPTL4 uncovers variations that reduce triglyceride and increase HDL. Nature Genetics, 39, 513-517 (2007).
34. Yin, Wu et al. Genetic variation in Angptl4 provides insight into protein processing and function, J. Biol. Chem., 284, 13213-13222 (2009).

REFERENCES (WORKING EXAMPLE 4)

1. Nachman, P. H, Jennette, J. C. & Falk, R. Primary glomerular disease. in *The Kidney*, 8$^{th}$ edn. (ed. Brenner, B. M.) 987-1066 (Elsevier, Philadelphia, 2008).
2. Marsh, J. B. & Drabkin, D. L. Experimental reconstruction of metabolic pattern of lipid nephrosis: key role of hepatic protein synthesis in hyperlipemia. *Metabolism* 9, 946-955 (1960).
3. Vaziri N. D. Molecular mechanisms of lipid disorders in nephrotic syndrome. *Kidney Int.* 63, 1964-1976 (2003).
4. Weinstock, P. H. et al. Severe hypertriglyceridemia, reduced high density lipoprotein, and neonatal death in lipoprotein lipase knockout mice. Mild hypertriglyceridemia with impaired very low density lipoprotein clearance in heterozygotes. *J. Clin. Invest.* 96, 2555-2568 (1995).
5. Shearer, G. C. & Kaysen, G. A. Endothelial bound lipoprotein lipase (LpL) depletion in hypoalbuminemia results from decreased endothelial binding, not decreased secretion. *Kidney Int.* 70, 647-653 (2006)
6. Clement, L. C. et al. Podocyte—secreted Angiopoietin-like-4 mediates proteinuria in glucocorticoid-sensitive nephrotic syndrome. *Nat Med.* 17, 117-122 (2011).
7. Chugh, S. S., Clement, L. C. & Macé, C. New insights into human minimal change disease: Lessons from animal models. *Am. J. Kid. Dis.* 59, 284-292 (2012).
8. Yoshida, K., Shimizugawa, T., Ono, M. & Furukawa, H. Angiopoietin-like protein 4 is a potent hyperlipidemia-inducing factor in mice and inhibitor of lipoprotein lipase. *J. Lipid Res.* 43, 1770-1772 (2002).

9. Sukonina, V., Lookene, A., Olivecrona, T. & Olivecrona, G. Angiopoietin-like protein 4 converts lipoprotein lipase to inactive monomers and modulates lipase activity in adipose tissue. *Proc. Natl. Acad. Sci. USA* 103, 17450-17455 (2006).
10. Romeo, S. et al. Population-based resequencing of ANGPTL4 uncovers variations that reduce triglycerides and increase HDL. *Nat. Genet.* 39, 513-516 (2007).
11. Yin, W. et al. Genetic variation in ANGPTL4 provides insights into protein processing and function. *J. Biol. Chem.* 284, 13213-13222 (2009).
12. Clement L. et al. Early changes in gene expression that influence the course of primary glomerular disease. *Kidney Int.* 72, 337-347 (2007).
13. Liu, G., Clement, L., Kanwar, Y. S., Avila-Casado, C. & Chugh, S. S. ZHX proteins regulate podocyte gene expression during the development of nephrotic syndrome. *J. Biol. Chem.* 281, 39681-39692 (2006),
14. Nakamura, T. et al. Sclerotic lesions in the glomeruli of Buffalo/Mna rats. *Nephron* 43, 50-55 (1986).
15. Le Berre, L. et al. Extrarenal effects on the pathogenesis and relapse of idiopathic nephrotic syndrome in Buffalo/Mna rats. *J. Clin. Invest.* 109, 491-498 (2002).
16. Neuger, L. et al. Effects of heparin on the uptake of lipoprotein lipase in rat liver. *BMC Physiol.* 4, 13 (2004).
17. Zhu, P. et al. Angiopoietin-like 4 protein elevates the prosurvival intracellular O2(-):H2O2 ratio and confers anoikis resistance to tumors. *Cancer Cell* 19, 401-415 (2011).
18. Mandard, S. et al. The fasting-induced adipose factor/angiopoietin-like protein 4 is physically associated with lipoproteins and governs plasma lipid levels and adiposity. *J. Biol. Chem.* 281, 934-944 (2006).
19. Zilleruelo, G., Hsia, S. L., Freundlich, M., Gorman, H. M. & Strauss, J. Persistence of serum lipid abnormalities in children with idiopathic nephrotic syndrome. *J. Pediatr.* 104, 61-64 (1984).
20. Yu, X. et al. Inhibition of cardiac lipoprotein utilization by transgenic overexpression of Angptl4 in the heart. *Proc. Natl. Acad. Sci. USA.* 102, 1767-1772 (2005).
21. Koliwad, S. K. et al. Angiopoietin-like 4 (ANGPTL4, fasting-induced adipose factor) is a direct glucocorticoid receptor target and participates in glucocorticoid-regulated triglyceride metabolism. *J. Biol. Chem.* 284, 25593-25601 (2009).
22. Eremina, V. et al. VEGF inhibition and renal thrombotic microangiopathy. *N. Engl. J. Med.* 358, 1129-1136 (2008).
23. Maynard, S. E., et al. Excess placental soluble fms-like tyrosine kinase 1 (sFlt1) may contribute to endothelial dysfunction, hypertension, and proteinuria in preeclampsia. *J Clin. Invest.* 111, 649-658 (2003).
24. Venkatesha, S. et al. Soluble endoglin contributes to the pathogenesis of preeclampsia. *Nat. Med.* 12, 642-649 (2006).
25. Wei, C. et al. Circulating urokinase receptor as a cause of focal segmental glomerulosclerosis. *Nat. Med.* 17, 952-960 (2011).
26. Wei, C. et al. Circulating suPAR in Two Cohorts of Primary FSGS. *J. Am. Soc. Nephrol.* 23, 2051-2059 (2012).
27. Avila-Casado, C. et al. Proteinuria in rats induced by serum from patients with collapsing glomerulopathy. *Kidney Int.* 66, 133-143 (2004).
28. Chugh, S. S., & Clement, L. C. Telomerase at the center of collapsing glomerulopathy. *Nat. Med.* 18, 26-27 (2012).
29. Chugh, S. et al. Aminopeptidase A: A nephritogenic target antigen of nephrotoxic serum. *Kidney Int.* 59, 601-613 (2001).
30. Imamura, S. et al. A novel method for measuring human lipoprotein lipase and hepatic lipase activities in postheparin plasma. *J. Lipid Res.* 49, 1431-1437 (2008).
31. Liu, G., et al. Neph1 and nephrin interaction in the slit diaphragm is an important determinant of glomerular permeability. *J. Clin. Invest.* 112, 209-221 (2003).
32. Chang, S. F., Reich, B., Brunzell, J. D. & Will, H. Detailed characterization of the binding site of the lipoprotein lipase-specific monoclonal antibody 5D2. *J. Lipid Res.* 39, 2350-2359 (1998).

TABLE 4

LEGEND TO THE SEQUENCE LISTING

| | |
|---|---|
| SEQ ID NO: 1 | Variant 1 of human Angptl4 polypeptide |
| SEQ ID NO: 2 | cDNA sequence of variant 1 of human Angptl4 |
| SEQ ID NO: 3 | Variant 2 of human Angptl4 polypeptide |
| SEQ ID NO: 4 | cDNA sequence of variant 2 of human Angptl4 |
| SEQ ID NO: 5 | Rat Angptl4 polypeptide |
| SEQ ID NO: 6 | cDNA sequence of rat Angptl4 polypeptide |
| SEQ ID NO: 7 | Mouse Angptl4 polypeptide |
| SEQ ID NO: 8 | cDNA sequence of mouse Angptl4 polypeptide |
| SEQ ID NO: 9 | Variant 1 of human Angptl4 polypeptide with substitutions |
| SEQ ID NO: 10 | Variant 2 of human Angptl4 polypeptide with substitutions |
| SEQ ID NOS: 11-22 | PCR primers and probes (see text) |
| SEQ ID NO: 23 | N-terminal multispecies consensus sequence with substitutions |
| SEQ ID NO: 24 | Central multispecies consensus sequence with substitutions |
| SEQ ID NO: 25 | C-terminal multispecies consensus sequence with substitutions |
| SEQ ID NO: 26 | N-terminal human consensus sequence with substitutions |
| SEQ ID NO: 27 | C-terminal human consensus sequence with substitutions |
| SEQ ID NO: 28 | Mutant variant of human Angptl4 polypeptide DKMNVLAHGLLQLGQGL |
| SEQ ID NOS: 29-90 | Sequences from Table 2 |
| SEQ ID NO: 91 | Reverse primer for amplification of aP2-Angptl4 construct |
| SEQ ID NO: 92 | Probe for identification of aP2-Angptl4 construct |
| SEQ ID NO: 93 | cDNA encoding peptide of SEQ ID NO: 80 |
| SEQ ID NO: 94 | cDNA encoding the peptide of SEQ ID NO: 87 |

What is claimed:

1. A mutant Angptl4 polypeptide comprising the following structure:

A-B-C wherein
   A has at least 95% identity with SEQ ID NO: 26, wherein: the residue at position 39 is a positively charged residue or a neutral residue; position 40 is K, A, or E; and positions 161-164 are not RRKR (SEQ ID NO: 95);
   B is an oligopeptide of 0-38 residues; and
   C has at least 95% identity with SEQ ID NO: 27.

2. The mutant Angptl4 polypeptide of claim 1, wherein position 39 of SEQ ID NO: 26 is A.

3. The mutant Angptl4 polypeptide of claim 1, wherein the sequence at positions 39 and 40 of SEQ ID NO: 26 is AE.

4. The mutant Angptl4 polypeptide of claim 1, wherein all of positions 161-164 of SEQ ID NO: 26 are independently selected from the group consisting of D, R, K, G, A, S, and V.

5. The mutant Angptl4 polypeptide of claim 1, wherein all of positions 161-164 of SEQ ID NO: 26 are independently selected from the group consisting of G, A, and V.

6. The mutant Angptl4 polypeptide of claim 1, wherein of the sequence at positions 161-164 of SEQ ID NO: 26 is selected from the group consisting of: SEQ ID NOS: 29-90.

7. The mutant Angptl4 polypeptide of claim 1, wherein of the sequence at positions 161-164 of SEQ ID NO: 26 is selected from GAAG (SEQ ID NO: 29), AAVV (SEQ ID NO: 78), GVVA (SEQ ID NO: 49), SGGG (SEQ ID NO: 87), and VAVA (SEQ ID NO: 90).

8. The mutant Angptl4 polypeptide of claim 1, wherein the mutant Angptl4 polypeptide has at least 95% sequence identity with SEQ ID NO: 9, and wherein position 39 of SEQ ID NO: 9 is selected from A or K.

9. The mutant Angptl4 polypeptide of claim 1, wherein the mutant Angptl4 polypeptide has at least 95% sequence identity with SEQ ID NO: 10, wherein position 39 of SEQ ID NO: 10 is selected from A or K.

10. The mutant Angptl4 polypeptide of claim 1, wherein the sequence at positions 39-40 of SEQ ID NO: 26 is AE and the sequence at positions 161-164 of SEQ ID NO: 26 is VAVA (SEQ ID NO: 90).

11. The mutant Angptl4 polypeptide of claim 1, wherein the polypeptide is sialylated.

12. An isolated polynucleotide encoding the mutant Angptl4 polypeptide of claim 1.

13. A genetically modified organism comprising the polynucleotide of claim 12.

14. An in vitro expression system comprising the polynucleotide of claim 12.

15. A pharmaceutical composition comprising a therapeutically effective amount of the mutant Angptl4 polypeptide of claim 1 in combination with a pharmaceutically acceptable carrier.

16. The pharmaceutical composition of claim 15, comprising about 0.035-1100 mg of the mutant Angptl4 polypeptide.

17. The pharmaceutical composition of claim 15, formulated for intravenous delivery or transdermal delivery.

18. A mutant Angptl4 polypeptide comprising the following structure:

A-B-C wherein
- A has at least 95% identity with SEQ ID NO: 26, wherein: the sequence at positions 39-55 is not DEMNVLAHGLLQLGQGL (SEQ ID NO: 96); position 40 is K, A, or E; and positions 161-164 are independently selected from the group consisting of SEQ ID NOS: 29-79 AND 81-90;
- B is an oligopeptide of 0-38 residues; and
- C has at least 95% identity with SEQ ID NO: 27.

19. The mutant Angptl4 polypeptide of claim 18, wherein position 39 of SEQ ID NO: 26 is a positively charged residue or a neutral residue.

20. The mutant Angptl4 polypeptide of claim 18, wherein position 39 of SEQ ID NO: 26 is A.

21. The mutant Angptl4 polypeptide of claim 18, wherein the sequence at positions 39 and 40 of SEQ ID NO: 26 is selected from the group consisting of: DK, DA, and AE.

22. The mutant Angptl4 polypeptide of claim 18, wherein all of positions 161-164 of SEQ ID NO: 26 are independently selected from the group consisting of G, A, and V.

23. The mutant Angptl4 polypeptide of claim 18, wherein of the sequence at positions 161-164 of SEQ ID NO: 26 is selected from GAAG (SEQ ID NO: 29), AAVV (SEQ ID NO: 78), GVVA (SEQ ID NO: 49), SGGG (SEQ ID NO: 87), and VAVA (SEQ ID NO: 90).

24. The mutant Angptl4 polypeptide of claim 18, wherein the sequence at positions 39-40 is DA or AE.

25. The mutant Angptl4 polypeptide of claim 18, wherein the mutant Angptl4 polypeptide has at least 95% sequence identity with SEQ ID NO: 9, wherein position 40 of SEQ ID NO: 9 is K, A, or E; and wherein positions 161-164 of SEQ ID NO: 9 are independently selected from the group consisting of SEQ ID NOS: 29-79 AND 81-90.

26. The mutant Angptl4 polypeptide of claim 18, wherein the mutant Angptl4 polypeptide has at least 95% sequence identity with SEQ ID NO: 10, wherein position 40 of SEQ ID NO: 10 is K, A, or E; and wherein positions 161-164 of SEQ ID NO: 10 are independently selected from the group consisting of SEQ ID NOS: 29-79 and 81-90.

27. The mutant Angptl4 polypeptide of claim 18, wherein the sequence at positions 39-40 of SEQ ID NO: 23 26 is DA and the sequence at positions 161-164 of SEQ ID NO: 26 is GVVA (SEQ ID NO: 49).

28. The mutant Angptl4 polypeptide of claim 18, wherein the sequence at positions 39-40 of SEQ ID NO: 26 is DK and the sequence at positions 161-164 of SEQ ID NO: 26 is GAAG (SEQ ID NO: 29).

29. The mutant Angptl4 polypeptide of claim 18, wherein the sequence at positions 39-40 of SEQ ID NO: 26 is DK and the sequence at positions 161-164 of SEQ ID NO: 26 is AAVV (SEQ ID NO: 78).

30. The mutant Angptl4 polypeptide of claim 18, wherein the sequence at positions 39-40 of SEQ ID NO: 26 is AE and the sequence at positions 161-164 of SEQ ID NO: 26 is VAVA (SEQ ID NO: 90).

31. The mutant Angptl4 polypeptide of claim 18, wherein the polypeptide is sialylated.

32. An isolated polynucleotide encoding the mutant Angptl4 polypeptide of claim 18.

33. A genetically modified organism comprising the polynucleotide of claim 32.

34. An in vitro expression system comprising the polynucleotide of claim 32.

35. A pharmaceutical composition comprising a therapeutically effective amount of the mutant Angptl4 polypeptide of claim 18 in combination with a pharmaceutically acceptable carrier.

* * * * *